US007344830B2

(12) United States Patent
Philpott et al.

(10) Patent No.: US 7,344,830 B2
(45) Date of Patent: *Mar. 18, 2008

(54) HETERODUPLEX TRACKING ASSAY

(75) Inventors: Sean Philpott, Defreestville, NY (US);
Barbara Weiser, East Greenbush, NY (US); Harold Burger, East Greenbush, NY (US)

(73) Assignee: Health Research Inc., Rensselaer, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/333,073

(22) Filed: Jan. 17, 2006

(65) Prior Publication Data
US 2006/0194227 A1    Aug. 31, 2006

Related U.S. Application Data

(60) Continuation-in-part of application No. 10/695,846, filed on Oct. 29, 2003, which is a division of application No. 09/963,064, filed on Sep. 25, 2001, now Pat. No. 6,727,060.

(60) Provisional application No. 60/282,354, filed on Apr. 6, 2001, provisional application No. 60/235,671, filed on Sep. 26, 2000.

(51) Int. Cl.
G01N 33/569    (2006.01)
C12Q 1/70    (2006.01)

(52) U.S. Cl. .................. 435/5; 435/235.1; 435/325; 435/372; 435/372.3; 435/41

(58) Field of Classification Search .................. None
See application file for complete search history.

(56) References Cited

U.S. PATENT DOCUMENTS 5,837,464 A    11/1998    Capon et al.
5,851,759 A    12/1998    Weiner (Continued)

FOREIGN PATENT DOCUMENTS

| WO | WO 99/14378 A | 3/1999 |
| WO | 99/67429 | 12/1999 |
| WO | WO 00/65356 | 11/2000 |

OTHER PUBLICATIONS

Nelson, et al. Evolutionary Variants of the Human Immunodeficiency Virus Type 1 V# Region Characterized by Using a Heteroduplex Tracking Assay. J Virology 1997 71(11):8750-5758.*

Primary Examiner—Mary Mosher
Assistant Examiner—Stuart W Snyder
(74) Attorney, Agent, or Firm—Thomas J. Kowalski; Frommer Lawrence & Haug LLP

(57) ABSTRACT

A change in viral tropism occurs in many HIV positive individuals over time and may be indicated by a shift in coreceptor use from CCR5 to CXCR4. The shift in coreceptor use to CXCR4 has been shown to correlate with increased disease progression. In patients undergoing HAART, the predominant populations of virus may be shifted back to CCR5-mediated entry after the CXCR4-specific strains have emerged. The present invention relates to a diagnostic method to monitor coreceptor use in the treatment and clinical management of human immunodeficiency virus (HIV) infection. The present invention further relates to a diagnostic method applied to HIV-positive individuals undergoing HAART to monitor the suppression of CCR5- or CXCR4-specific strains. The diagnostic methods may be used to assist in selecting antiretroviral therapy and to improve predictions of disease prognosis over time. The methods of the invention include cell-based methods, including cell fusion assays, and molecular-based methods, including heteroduplex tracking assay, to both quantitatively and qualitatively analyze patient-derived HIV for coreceptor usage.

28 Claims, 6 Drawing Sheets

U.S. PATENT DOCUMENTS

| | | | |
|---|---|---|---|
| 5,994,515 | A | 11/1999 | Hoxie |
| 6,107,019 | A | 8/2000 | Allaway et al. |
| 6,727,060 | B2* | 4/2004 | Philpott et al. ............ 435/5 |
| 7,097,970 | B2 | 8/2006 | Petropoulos et al. |
| 7,169,551 | B2 | 1/2007 | Petropoulos et al. |
| 2003/0180717 | A1 | 9/2003 | Esteban et al. |
| 2005/0214743 | A1 | 9/2005 | Richman et al. |
| 2006/0183110 | A1 | 8/2006 | Petropoulos et al. |
| 2006/0194227 | A1* | 8/2006 | Philpott et al. ............ 435/6 |
| 2006/0223107 | A1 | 10/2006 | Chenna et al. |

OTHER PUBLICATIONS

Zhang et al. Selection for Specific Sequences in the External Envelope Protein in Human Immunodeficiency Virus Type I upon Primary Ingection J Virology 1993 67(6):3345-3356.*

Philpott S. et al. "Preferential suppression of CXCR4-specific strains of HIV-1 by antiviral therapy." J. Clin. Invest., vol. 107(4), Feb. 2001, p. 431-438.

Moore JP. Et al. "Co-receptors for HIV-1 entry." Cur. Opin. Immunol., vol. 9, 1997, pp. 551-562.

Callaway DS. Et al. "Virus phenotype switching and disease progression in HIV-1 infection." Proc. R. Soc. Lond., vol. 266, 1999, pp. 2523-2530.

Wodarz D. et al. "Defining CTL-induced pathology: implications for HIV." Virology, vol. 274, Aug. 2000, pp. 94-104.

Clerici et al. (2000) "Different immunologic profiles characterize HIV infection in highly active antiretroviral therapy-treated and antiretroviral-naïve patients with undetectable viraemia. The Master Group".AIDS 14(2): 109-116.

Conner et al. "Change in coreceptor use correlates with disease progression in HIV-1-infected individuals" J. Exp. Med. vol. 185(4), Feb. 17, 1997, pp. 621-628.

Bjorndal et al., "Coreceptor usage of primary human immunodeficiency virus type 1 isolates varies according to biological phenotype" Journal of Virology, Oct. 1997, pp. 7478-7487.

Burger and Weiser, (1997) "Biology of HIV-1 in women and men" Obstetrics and Gynecology Clinics of North America, vol. 24, No. 4, pp. 731-742.

Pierson et al. (2000) "Characterization of chemokine receptor utilization of viruses in the latent reservoir for human immunodeficiency virus type 1". J. Virol. 74(17):7824-33.

Mosier (2000) "Virus and target cell evolution in human immunodeficiency virus type 1 infection", Immunologic Research, vol. 21, No. 2-3, pp. 253-258.

Verrier et al. (1999) "Role of the HIV type 1 glycoprotein 120 V3 loop in determining coreceptor usage" AIDS Research and Human Retroviruses, vol. 15, No. 9, 1999, pp. 731-743.

Chan et al. (1999) "V3 recombinants indicate a central role for CCR5 as a coreceptor in tissue infection by human immunodeficiency virus type 1" Journal of Virology, Mar. 1999, pp. 2350-2358.

Anderson et al. (1998) "Early reduction of immune activation in lymphoid tissue following highly active HIV therapy" AIDS 12:F123-9.

Berger et al. (1999) "Chemokine receptors as HIV-1-coreceptors: roles in viral entry, tropism, and disease." Annu. Rev. Immunol 17:657-700.

Berkowitz et al. (2000) "Casual relationships between HIV-1 coreceptor utilization, tropism, and pathogenesis in human thymus." J. AIDS Hum. Retro. 16(11):1039-45.

Cammack N. (1999) "Human immunodeficiency virus type 1 entry and chemokine receptors: a new therapeutic target." Antivir. Chem Chemother. 10(2):53-62.

Cecilia et al. (2000) "Absence of coreceptor switch with disease progression in human immunodeficiency virus infections in India" Virology 271(2):253-8.

Dreyer et al. (1999) "Primary isolate neutralization by HIV type 1-infected patient sera in the era of highly active antiretroviral therapy." AIDS Res. Hum. Retrovir 15(17):1563-1571.

Equils et al. (2000) "Recovery of replication-competent virus from CD4 T cell reservoirs and change in coreceptor use in human immunodeficiency virus type 1-infected children responding to highly active antiretroviral therapy." J. Inf. Dis. 182:751-757.

Este et al. (1999) "Shift of clinical human immunodeficiency virus type 1 isolates from X4 to R5 and prevention of emergence of the syncytium-inducing phenotype by blockade of CXCR4". J. Virol. 73:5577-85.

Fang et al. (1996) "Molecular cloning of full-length HIV-1 genomes directly from plasma viral RNA". J. Acquir. Immune Defic. Syndr. Hum. Retrovirol. 12(4):352-7.

Giovannetti et al. (1999) "CCR5 and CXCR4 chemokine receptor expression and beta-chemokine production during early T cell repopulation induced by highly active antiretroviral therapy". Clin. Exp. Immunol. 118(1):87-94.

Glushakova et al. (2000) "Preferential coreceptor utilization and cytopathicity by dual-topic HIV-1 in human lymphoid tissue ex vivo". J. Clin. Invest. 104:R7-R11.

Hotkamp et al. (2000) "Unexpected corecptor usage of primary human immunodeficiency virus type 1 isolates from virermic patients under highly active antiretroviral therapy." J. Inf. Dis. 181(2):513-21.

Kokkotou et al. (2000) "In vitro correlates of HIV-2-mediated HIV-1 protection." Proc. Natl. Acad. Sci. USA 97(12):6797-8002.

Kusunoki et al. (1999) "Antisense oligodeoxynulceotide complementary to CXCR4 mRNA block replication of HIV-1 in COS cells." Nucleosides Nucleotides 18(6-7):1705-8.

Lee et al. (1999) "Quantification of CD4, CCR5, and CXCR4 levels on lymphocyte subsets, dendritic cells, and differentially conditioned monocyte-derived macrophages" Proc. Natl. Acad. Sci. USA 96(9):5215-20.

Lew et al. (1998) "Determinations of levels of human immunodeficiency virus type 1 RNA in plasma: reassessment of parameters affecting assay outcome. TUBE Meeting Workshop Attendees. Technology Utilization for HIV-1 Blood Evaluation and Standardization in Pediatrics." J. Clin. Microbiology (36)6:1471-9.

Martinon et al. (1999) "Persistent alterations in T-cell repertoire, cytokine and chemokine receptor gene expression after 1 year of highly active antiretroviral therapy." AIDS. 13(2):185-94.

Michael et a. (1999) "Viral phenotype and CCR5 genotype", Nat. Med. 5(12):1330.

Philpott et al. (1999) "Antiviral therapy may preferentially eliminate CXCR4-specific strains of HIV-1" Interscience Conference on Antimicrobial Agents and Chemotherapy (ICAAC) Moscone Center San Francisco, CA, USA Sep. 26-29, 1999 Abstract 1836 p. 513.

Samson et al. (1996) "Resistance to HIV-1 infection in Caucasian individuals bearing mutant alleles of the CCR-5 chemokine receptor gene", Nature 382:722-5.

Schramm et al. (2000) "Viral entry through CXCR4 is a pathogenic factor and therapeutic target in human immunodeficiency virus type 1 disease", J. Virol. 74(1):184-92.

Shankarappa et al. (1999) "Consistent viral evolutionary changes associated with the progression of human immunodeficiency virus type 1 infection", J. Virol. 73(12):10489-502.

Trkola et al. (1999) "A cell line-based neutralization assay for primary human immunodeficiency virus type 1 isolates that use either the CCR5 or the CXCR4 coreceptor", J. Virol. 73(11):8966-8974.

Vicenzi et al. (1999) "Envelope-dependent restriction of human immunodeficiency virus type 1 spreading in CDS(+) T lymphocytes: R5 but not X4 viruses replicate in the absence of T-cell receptor restimulation", J. Virol 73(9):7515-23.

Wang et al. (2000) "Molecular and biological interactions between two HIV-1 strains from a coinfected patient reveal the first evidence in favor of viral synergism" Virology 274(1):105-119.

Zhang et al. (1999) "Will multiple coreceptors need to be targeted by inhibitors of human immunodeficiency virus type 1 entry", J. Virol. 73(4):3443-8.

Penn et al., "CXCR4 utilization is sufficient to trigger CD4+ T cell depletion in HIV-1-infected human lymphoid tissue", Proceedings of the National Academy of Sciences of the United States of America, vol. 96, No. 2(Jan. 19, 1999), pp. 663-8.

Overbaugh et al., "Distinct but related human immunodeficiency virus type 1 variant populations in genital secretions and blood", AIDS Research and Human Retroviruses. vol. 12, No. 2(Jan. 20, 1996), pp. 107-15. Abstract Only.

Shang CAO et al., "Study on transient infection of T cell lines by M tropic HIV-1 strains", Chinese Journal of Experimental and Clinical Virology, vol. 13, No. 2, Jun. 1999, pp. 163-169.

Shan Li et al., "Persistent CCR5 Utilization and Enhanced Macrophage Tropism by Primary Blood Human Immunodeficiency Virus Type 1 Isolates from Advanced Stages of Disease and Comparison to Tissue-Derived Isolates", Journal of Virology, Dec. 1999, vo. 73, No. 12, pp. 9741-9755.

Julie A. E. Nelson et al., "Patterns of Changes in Human Immunodeficiency Virus Type 1 V3 Sequence Populations Late in Infection", Journal of Virology, Sep. 2000, vol. 74, No. 18, pp. 8494-8501.

Timothy J. Wilkin et al., "HIV Type 1 Chemokine Coreceptor Use among Antiretroviral-Experienced Patients Screened for a Clinical Trial of a CCR5 Inhibitor: AIDS Clinical Trial Group A5211", Clinical Infectious Diseases, Feb. 15, 2007, vol. 44, No. 4, pp. 591-595.

Charlotte Tscherning-Casper et al., "Coreceptor Usage of HIV-1 Isolates Representing Different Genetic Subtypes Obtained From Pregnant Cameroonian Women", Journal of Acquired Immune Deficiency Syndromes, vol 24, No. 1 May 1, 2000, pp. 1-9.

Dalma Vodros et al., "Quantitative Evaluation of HIV-1 Coreceptor Usin in the GHOST (3) Cell Assay", Virology, vol. 291, No. 1, Dec. 5, 2001, pp. 1-11.

Paul R. Gorry et al., "Macrophage Tropism of Human Immunodeficiency Virus Type 1 Isolates from Brain and Lymphoid Tissues Predicts Neurotropism Independent of Coreceptor Specificity", Journal of Virology, Nov. 2001, vol. 75, No. 21, pp. 10073-10089.

Tracking HIV evolution from birth to death by Mike Nagle, Oct. 17, 2007; http://drugresearcher.com/news/ng.asp?id=80640.

* cited by examiner

US 7,344,830 B2

HETERODUPLEX TRACKING ASSAY

RELATED APPLICATIONS/PATENTS & INCORPORATION BY REFERENCE

This application is a continuation-in-part of U.S. application Ser. No. 10/695,846, filed Oct. 29, 2003, which is a divisional application of U.S. application Ser. No. 09/963,064, filed Sep. 25, 2001 and issued as U.S. Pat. No. 6,727,060 on Apr. 27, 2004, and which claims priority to U.S. Provisional Application Ser. No. 60/282,354, filed Apr. 6, 2001 and U.S. Provisional Application Ser. No. 60/235,671, filed Sep. 26, 2000.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

This work was supported by the government, in part, by Grant U01AI35004 from the National Institute for Allergy and Infectious Diseases and a National Research Service Award (1F32HD08478-01) from the National Institute of Child Health and Human Development. The government may have certain rights to this invention.

FIELD OF THE INVENTION

The present invention relates to a diagnostic method to monitor coreceptor use in treatment of human immunodeficiency virus (HIV, or "an AIDS virus") infection. This method may assist in selecting antiretroviral therapy and to improve predictions of disease prognosis. Moreover, the present invention relates to qualitative and quantitative methods for evaluating patient-derived HIV samples for coreceptor use, e.g. the presence and/or absence of CCR5 and CXCR4-specific strains or shifts in coreceptor use with respect to disease progression or treatment. The qualitative and quantitative methods of the invention may relate to cell-based systems, such as a cell-fusion assay, and molecular-based systems, such as a heteroduplex tracking assay, to monitor, measure, evaluate, detect, etc. the coreceptor use of patient-derived HIV. The present invention further relates to a diagnostic method to monitor the suppression of CXCR4-specific strains in HIV infected individuals undergoing anti-retroviral therapy.

BACKGROUND OF THE INVENTION

HIV uses a receptor-mediated pathway in the infection of host cells. HIV-1 requires contact with two cell-surface receptors to gain entry into cells and initiate infection; CD4 is the primary receptor. CXCR4 and CCR5, members of the chemokine receptor family of proteins, serve as secondary coreceptors for HIV-1 isolates that are tropic for T-cell lines or macrophages, respectively. Deng et al. (1996) Nature 381:661-6; Doranz et al. (1996) Cell 86:1149-59; and Berger et al. (1998) Nature 391:240. CXCR4 or CCR5, in conjunction with CD4, form a functional cellular receptor for entry of certain strains of HIV into cells. Recent reports indicated that the viral envelope glycoprotein gp120 interacts directly with chemokine receptors generally at a step following CD4 binding. Lapham et al. (1996) Science 274:602-605; Moore (1997) Science 276:51; Wu et al. (1996) Nature 384:179-183; and Hesselgesser et al. (1997) Current Biology 7:112-121. Envelope variants selectively interact with either CXCR4 or CCR5.

Coreceptor use plays a critical role in viral tropism, pathogenesis, and disease progression. HIV-1 strains transmitted in vivo generally use CCR5 (CCR5 viruses), whether by sexual, parenteral, or mother-to-child transmission. Fenyo et al. (1998) Nature 391:240; Samson et al. (1996) Nature 382:722-5; Shankarappa et al. (1999) J. Virol. 73:10489-502; and Scarlatti et al. (1997) Nature Med. 3:1259-65. These viruses typically infect macrophages and primary CD4+ lymphocytes, and do not form syncytia in vitro. Björndal et al. (1997) J. Virol. 71:7478-87. These viruses are said to be macrophage tropic (M-tropic). After primary HIV-1 infection, viral populations are usually characterized by molecular heterogeneity. Shankarappa et al. (1999); and Glushakova et al. (1999) J. Clin. Invest. 104:R7-R11.

Years after chronic infection is established, strains using CXCR4 emerge in ~50% of infected individuals. Berger et al. (1998); Scarlatti et al. (1997); Koot et al. (1993); and Connor et al. (1997) J. Exp. Med. 185:621-8. In many cases, the CXCR4 and CCR5 strains coexist to some extent in the viral swarm or population. CXCR4 strains not only infect primary T-lymphocytes but also replicate in T-cell lines and induce syncytia. Björndal et al. (1997). These viruses are said to be T-cell tropic (T-tropic). This difference in cell tropism correlates with disease progression. During HIV infection, strains isolated from individuals early in the course of their infection are usually M-tropic, while viruses isolated from approximately 50% of individuals with advanced immunodeficiency also include viruses that are T-tropic.

The finding that change from M- to T-tropic viruses over time in infected individuals correlates with disease progression suggested that the ability of the viral envelope to interact with CXCR4 represents an important feature in the pathogenesis of immunodeficiency and the development of full blown Acquired Immunodeficiency Syndrome (AIDS). CXCR4 strains have now been shown to have a striking influence on HIV-1 disease progression. Cytopathicity toward the general CD4+ T cell population in lymphoid tissue is associated with the use of CXCR4. Glushakova et al. (1999). The emergence of CXCR4 virus is predictive of rapid depletion of CD4+ cells and acceleration of HIV-1 disease progression. Berger et al. (1998); Scarlatti et al. (1997); Koot et al. (1993); and Connor et al. (1997). A recent analysis of HIV-1 coreceptor use in infected individuals suggested that the rapid CD4+ cell decline is related to the ability of CXCR4 viruses to infect an expanded spectrum of crucial target cells as compared to CCR5 strains. Blaak et al. (2000) Proc. Natl. Acad. Sci. USA 97:1269-74. In vitro results suggest that selective blockade of CXCR4 receptors may prevent the switch from the less pathogenic CCR5 strains to the more pathogenic CXCR4 strains. Este et al. (1999) J. Virol. 73:5577-85.

All of the known genetic determinates of coreceptor usage are found in the envelope gene (env), with the key determinates being found in the region of the env gene encoding the third variable (V3) domain of the gp120 glycoprotein. Previously, HIV-1 coreceptor utilization had been predicted according to the sequence of the V3 portion of the env gene. Hung C S et al. (1999); and Briggs D R et al. (2000). For example, an accumulation of positively charged amino acid located in the V3 domain, for example at positions 11 and 25 of the V3 domain and is a common feature of CXCR4-specific viruses. Fouchier R A et al. (1992); Milich L. et al. (1997). The V3 region of CXCR4-specific viruses also can exhibit greater sequence variation than their CCR5-specific counterparts, in particular respect with common laboratory HIV isolates at HTLV-IIIB/LAV and JR-CSF. Milich L. et al. (1997).

Accordingly, diagnostic methods for use in detecting CXCR4 isolates and/or monitoring shifts in coreceptor use (e.g. shifts from CXCR4-specific HIV to CCR5-specific HIV and vice versa) would be beneficial for predicting disease progression over time or in response to treatment. Moreover, cell-based and molecular-based methods to monitor, measure, evaluate, detect, etc. HIV coreceptor use which are reliable, accurate, and easy to use as well as being qualitative and/or quantitative in their approach would be a welcomed advance to the art.

In particular, diagnostic methods, e.g. cell-based and/or molecular-based methods, for measuring, monitoring, evaluating, detecting, etc. patient-derived HIV samples for coreceptor usage would be beneficial for evaluating HIV disease progression in the face of various anti-HIV treatment and therapies. For example, treatment of infected individuals with highly active antiretroviral therapy (HAART) has led to a dramatic decline in both HIV-1-related illness and death. Palella et al. (1998) N. Engl. J. Med. 338:853-60. Early clinical trials demonstrated a reduction of plasma HIV-1 RNA loads to undetectable levels in the majority of treated individuals. Hammer et al. (1997) N. Engl. J. Med. 337: 725-33; and Autran et al. (1997) Science 277:112-6. Subsequent studies, however, showed more limited success in achieving and maintaining viral suppression. Deeks et al. (2000) J. Inf. Dis. 181:946-53; and Mezzaroma et al. (1999) Clin. Inf. Dis. 29:1423-30. Yet many patients experienced immunologic and clinical responses to HAART without sustained suppression of plasma viremia. Deeks et al. (2000); and Mezzaroma et al. (1999).

In comparison to pretherapy determinations, expression of CXCR4 was significantly increased, and CCR5 decreased, following three months of an anti-viral regimen. Giovannetti et al. (1999) Clin. Exp. Immunol. 118:87-94. Changes in coreceptor expression occurred in association with a decrease in viral load and T cell activation, and an increase in naive and memory T cells, suggesting peripheral redistribution of T cell compartments. In a separate study, HAART was reported to reduce the expression of CXCR4 and CCR5 in lymphoid tissue. Andersson et al. (1998) AIDS 12:F123-9. These studies did not address coreceptor usage in patients undergoing HAART. The effects of HAART on coreceptor usage by viral populations were heretofore unknown.

The citation or identification of any document in this application is not an admission that such document is available as prior art.

OBJECTS AND SUMMARY OF THE INVENTION

The present invention provides diagnostic methods and components therefore for use in monitoring, measuring, evaluating, detecting, etc. viral coreceptor usage of patient-derived HIV during disease progression or during, before, or after administering HIV-related treatments and/or therapies.

In patients undergoing highly active antiretroviral therapy (HAART), the predominant populations of virus shift back to CCR5-mediated entry after the CXCR4-specific strains emerge. HAART may affect either the expression of CCR5 over CXCR4 or, alternatively, it may be influencing the kind of viral variant that predominates, such as CCR5-specific versus CXCR4-specific viruses. There is a correlation between the emergence of CXCR4-specific strains and rapid HIV disease progression to accurately predict disease prognosis over time and in response to treatment, a diagnostic method would be useful to monitor the presence (or absence) of CXCR4-specific strains and/or CCR5-specific strains and shifts in coreceptor use over time. The diagnostic methods (e.g. cell-based and/or molecular-based methods) of the invention permits both qualitative and quantitative studies of the effects of antiretroviral therapies, such as HAART, on coreceptor use by populations of virus. Thus, a diagnostic method for use in monitoring shifts in coreceptor use may be beneficial for measuring the therapeutic efficacy of various HIV treatment regimes, such as HAART.

The correlation between CXCR4-specific strains and rapid disease progression indicates that a diagnostic method would be useful to monitor the presence of CXCR4-specific strains and shifts in coreceptor use associated with HIV disease progression. Application of the diagnostic method allows more accurate predictions of disease prognosis over time.

The effect of HAART on coreceptor use by populations of virus has not heretofore been quantitatively studied. Herein, it is shown that in patients undergoing combination antiretroviral therapy, including HAART, the predominant populations of virus can shift back to CCR5-mediated entry once the CXCR4-specific strains have emerged.

Therefore, a diagnostic method is also useful to monitor the presence of CXCR4-specific strains and shifts in coreceptor use in patients undergoing antiretroviral therapy. Application of the diagnostic method allows for the close monitoring of the effectiveness of antiretroviral therapy.

The present invention relates to a diagnostic method to determine whether CXCR4 or CCR5 isolates are present in a patient which may comprise assaying for coreceptor use.

The present invention further relates to a diagnostic method to determine whether CXCR4 or CCR5 strains are present in a patient which may comprise transforming cells with an HIV envelope gene variant cloned from an infected patient, selectively fusing the cells with an indicator cell line expressing an HIV envelope-compatible coreceptor, and assaying for fusion.

The present invention also relates to a diagnostic method to determine whether CXCR4 or CCR5 strains are present in a patient which may comprise obtaining patient-derived virus and assaying the isolates for coreceptor use.

The present invention further relates to a diagnostic method to monitor shifts in coreceptor use associated with changes in HIV disease progression.

The present invention also relates to a diagnostic method to monitor shifts in coreceptor use associated with changes in HIV disease progression which may comprise transforming cells with an HIV envelope gene variant cloned from an infected patient, selectively fusing the cells with an indicator cell line expressing an HIV envelope-compatible coreceptor, and assaying for fusion.

The present invention further relates to a diagnostic method to monitor shifts in coreceptor use associated with changes in HIV disease progression which may comprise transforming cells which may contain an HIV Tat-activatable reporter gene construct with an HIV envelope gene variant cloned from an infected patient, selectively fusing the cells with an indicator cell line containing a constitutively active that gene and an HIV envelope-compatible coreceptor, and assaying for fusion by detection of reporter gene expression.

The present invention also relates to a diagnostic method to monitor shifts in coreceptor use associated with changes in HIV disease progression which may comprise determining CXCR4 coreceptor use, CCR5 coreceptor use, and a ratio of HIV using the CXCR4 coreceptor compared to HIV using the CCR5 coreceptor.

The present invention also relates to a diagnostic method to monitor shifts in coreceptor use associated with changes in HIV disease progression by obtaining patient-derived virus and deriving biological clones therefrom, assaying the clones for coreceptor use, and applying a method of quantitating the proportion of virus that uses each coreceptor.

The present invention also relates to a diagnostic method to determine whether CXCR4 or CCR5 strains are present in patients infected with HIV undergoing antiretroviral therapy.

The present invention further relates to a diagnostic method to determine whether CXCR4 or CCR5 strains are present in patients infected with HIV undergoing antiretroviral therapy which may comprise transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention also relates to a diagnostic method to determine whether CXCR4 or CCR5 strains are present in patients infected with HIV undergoing antiretroviral therapy which may comprise transforming cells which may contain an HIV Tat-activatable reporter gene construct with an HIV envelope gene variant cloned from an infected patient, selectively fusing the cells with an indicator cell line containing a constitutively active that gene and an HIV envelope-compatible coreceptor, and assaying for fusion by detection of reporter gene expression before and/or after initiating antiretroviral therapy.

The present invention further relates to a diagnostic method to determine whether CXCR4 or CCR5 strains are present in patients infected with HIV undergoing antiretroviral therapy which may comprise obtaining patient-derived virus and assaying the virus for coreceptor use before and/or after initiating antiretroviral therapy.

The present invention also relates to a diagnostic method to monitor the suppression of CXCR4-specific strains in patients infected with HIV undergoing antiretroviral therapy.

The present invention further relates to a diagnostic method to monitor the suppression of CXCR4-specific strains in patients infected with HIV undergoing antiretroviral therapy which may comprise transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention also relates to a diagnostic method to monitor the suppression of CXCR4-specific strains in patients infected with HIV undergoing antiretroviral therapy which may comprise transforming cells containing an HIV Tat-activatable reporter gene construct with an HIV envelope gene variant cloned from an infected patient, selectively fusing the cells with an indicator cell line which may contain a constitutively active that gene and an HIV envelope-compatible coreceptor, and assaying for fusion by detection of reporter gene expression before and/or after initiating antiretroviral therapy.

The present invention further relates to a diagnostic method to monitor the suppression of CXCR4-specific strains in patients infected with HIV undergoing antiretroviral therapy which may comprise obtaining patient-derived virus and assaying the virus for coreceptor use before and/or after initiating antiretroviral therapy.

The present invention further relates to a diagnostic method to monitor the suppression of CXCR4-specific strains in patients infected with HIV undergoing antiretroviral therapy which may comprise determining CXCR4 coreceptor use, CCR5 coreceptor use, and a ratio of HIV using the CXCR4 coreceptor compared to HIV using the CCR5 coreceptor before and/or after initiating antiretroviral therapy.

The present invention also relates to a diagnostic method to monitor the suppression of CXCR4-specific strains in patients infected with HIV undergoing antiretroviral therapy which may comprise obtaining primary viral isolates and deriving biological clones therefrom, assaying the clones for coreceptor use, and applying a method for quantitating the proportion of virus in a primary isolate that uses each coreceptor before and/or after initiating antiretroviral therapy.

The present invention further relates to a diagnostic method to monitor the suppression of CXCR4-specific strains in patients infected with HIV undergoing antiretroviral therapy which may comprise determining the sequence of HIV envelope gene before and/or after initiating antiretroviral therapy.

Another aspect of the present invention relates to molecular-based methods of monitoring, measuring, evaluating, detecting, etc. viral coreceptor usage of patient-derived HIV during disease progression or during, before, or after administering retroviral treatments and/or therapies, such as HAART.

In one embodiment, the present invention relates to a molecular-based system to quantitatively determine the proportion of patient-derived HIV utilizing each coreceptor, i.e. the proportion of HIV in the patient-derived HIV population using the CCR5 coreceptor compared to the proportion of HIV specific for the CXCR4 coreceptor. This ratio can be thought of as a continuous, nonlinear variable between one (1) and zero (0) and can be viewed as representing the proportion of virus using CCR5. For example, depending on the particular molecular-based system used, a nonlinear ratio variable of near one (1) can describe a population of HIV comprising more or mostly CCR5-specific viruses. Conversely, a nonlinear ratio variable of near zero (0) can indicate a virus population comprising more or mostly CXCR4-specific viruses.

In another embodiment, the invention relates to a molecular-based system to qualitatively evaluate a patient-derived HIV sample to determine whether the viral sample contains CXCR4-using viruses.

The molecular-based systems of the present invention relate to a heteroduplex tracking assay to analyze a portion of the HIV-1 genome encompassing determinates of coreceptor utilization. All of the genetic determinates of HIV-1 coreceptor utilization may be found in the envelope gene (env), with key determinates being found in the third variable (V3) domain of the gp120 glycoprotein.

The heteroduplex tracking assay of the invention may be carried out generally, while not being limited thereto, according to the basic steps of: (a) obtaining HIV viral RNA from the patient, (b) amplifying, e.g. by PCR and/or reverse transcription, a portion of the viral genome containing the main genetic determinates of coreceptor usage, e.g. a genomic portion comprising the V3 domain of the gp120 envelope glycoprotein, (c) forming heteroduplexes and/or homoduplexes with labeled nucleic acid-based probes prepared from a corresponding genomic region of a HIV strain with known coreceptor usage, e.g. the same genomic portion comprising the V3 domain of gp120, and (d) subjecting the heteroduplexes and homoduplexes to a separation system, e.g. electrophoresis through non-denaturing polyacrylamide gels, wherein the heteroduplexes and homoduplexes have differing and distinguishable mobilities to provide a characteristic mobility pattern, e.g. a electrophoretic pattern, such that the coreceptor usage can be determined. For example, the presence of an electrophoretic pattern comprising slow-moving heteroduplexes is indicative of the presence of CXCR4-specific viruses in the HIV sample. The heteroduplex tracking assay may be performed at any point during disease progression or during, before, or after administering antiretroviral therapy. Further, the heteroduplex tracking assay may be carried out either to attain qualitative results or quantitative results.

Accordingly, an aspect of the present invention may be directed to a heteroduplex tracking assay (HTA)-based diagnostic method for monitoring the efficacy of antiretroviral therapy in a patient, or a sample isolate from the patient, which may comprise quantitating usage of the CXCR4 and/or CCR5 coreceptor in HIV derived from a patient isolate, and determining whether there has been a change in coreceptor usage.

The present invention further relates to a method of determining CXCR4 and/or CCR5 coreceptor usage in a patient before initiating antiretroviral therapy which may comprise the steps of: (a) obtaining HIV from patient-derived samples; (b) deriving molecular clones of HIV from patient-derived samples; (c) and assaying the molecular clones using a heteroduplex tracking assay to quantitate CXCR4 and/or CCR5 coreceptor usage in the patient.

Another aspect of the present invention relates to a method of monitoring the efficacy of antiretroviral therapy in a patient which may comprise the steps of: (a) obtaining HIV from a patient-derived sample before, during or after antiretroviral therapy; (b) deriving molecular clones of HIV from the patient-derived samples, and using an HTA to quantitate CXCR4 and/or CCR5 coreceptor usage in the patient.

Still another aspect of the present invention further relates to a method of quantitating CXCR4 and/or CCR5 coreceptor usage by HIV derived from a patient sample which may comprise deriving molecular clones of HIV from a patient, using an HTA to determine coreceptor usage of each clone, and determining the ratio of HIV strain using the CCR5 coreceptor in comparison to that using the CXCR4 coreceptor.

The present invention also relates to a method of determining the ratio of CCR5 to CXCR4 coreceptor usage in a patient-derived HIV sample before initiating antiretroviral therapy which may comprise deriving multiple molecular clones of HIV from a patient sample, using an HTA to determine coreceptor usage by HIV clones, and determining the ratio of HIV strain using the CCR5 coreceptor in comparison to that using the CXCR4 coreceptor before, during, or after antiretroviral therapy whereby the ratio of CCR5 to CXCR4 co-receptor usage is used to help make therapeutic clinical decisions.

The present invention further relates to a method of monitoring the efficacy of antiretroviral therapy in a patient which involves measuring CCR5 and CXCR4 coreceptor usage by a molecular clone or clones of HIV obtained from patient-derived samples comprised of using an HTA to determine the ratio of HIV using the CCR5 coreceptor compared to virus using the CXCR4 coreceptor before, during or after antiretroviral therapy whereby efficacy of the antiretroviral therapy is related to a decrease of CXCR4-using strains of HIV during or after therapy.

Another aspect of the present invention relates to a method of detecting a change in coreceptor usage in a patient which may comprise deriving molecular clones of HIV from a patient at two different time points, using an HTA to determine coreceptor usage in the molecular clones at each time point, quantitating CXCR4 and/or CCR5 coreceptor usage at each time point, and comparing the ratios of coreceptor usage to determine whether there has been a change in coreceptor usage over time.

The present invention further relates to a method of measuring in a patient-derived biological sample the proportion of HIV using the CCR5 coreceptor compared to the proportion of HIV using the CXCR4 coreceptor which may comprise using an HTA to screen individual molecular clones of patient-derived HIV to determine the coreceptor usage of each individual clone and then comparing the number of molecular clones using either of each coreceptor to determine the proportion of HIV using the CCR5 coreceptor versus the CXCR4 coreceptor.

Still another aspect of the instent invention relates to a method of measuring in a patient-derived biological sample the proportion of HIV using the CCR5 coreceptor compared to the proportion of HIV using the CXCR4 coreceptor which may comprise using an HTA to screen individual molecular clones of HIV from a patient sample to determine the coreceptor usage of each individual molecular clone, the HTA producing either a first or second result, and further comprising comparing the number of molecular clones using either of each coreceptor to determine the proportion of HIV using the CCR5 coreceptor versus the CXCR4 coreceptor wherein the first result indicates HIV using the CCR5 coreceptor and the second result indicates HIV using the CXCR4 coreceptor.

In one embodiment of the invention, the biological sample may contain a bodily fluid, such as blood, plasma, and spinal fluid.

In a further embodiment of the invention, the individual molecular clones may each comprise a DNA sequence corresponding to a portion of the HIV genome may further comprise at least a portion of the genetic determinates of coreceptor usage. The individual molecular clones may each comprise a DNA sequence corresponding to a portion of the HIV genome which may comprise at least a portion of the genetic determinates of coreceptor usage wherein the genetic determinates are derived from the env gene.

Another embodiment relates to molecular clones which may be derived from RNA of the patient-derived HIV and which may correspond to the HIV genome or a portion thereof and which may comprise the genetic determinates of coreceptor usage or a portion thereof. Such molecular clones may be prepared by PCR of the RNA of the patient-derived HIV and at least one set of oligonucleotide primers, which may consist of HTA 6816F (SEQ ID NO: 26) and HTA7359R (SEQ ID NO: 27). In another embodiment of the invention, one set of oligonucleotide primers may consist of V3-7092F (SEQ ID NO: 28) and V3-7232R (SEQ ID NO: 29).

In another embodiment, the number of individual molecular clones is at least 20, preferably 25, which the Strong Law of Large Numbers predicts will produce a variance of <5% from the true value. The number of individual molecular clones may still further preferably be 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200.

In another embodiment, the heteroduplex tracking assay may comprise the steps of: (a) amplifying the individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means: and (d) detecting the presence or absence of heteroduplex molecules; wherein the presence or absence of heteroduplex molecules reveals coreceptor usage. In one embodiment, the labeled probe may be derived from a known HIV-1 CCR5 clone. In another embodiment, the labeled probe may be derived from a known HIV-1 CXCR4 clone. The labeled probe may comprise a detectable moiety, a radioisotope, biotin, a fluorescent moiety, a fluorophore, a chemiluminescent moiety, or an enzymatic moiety.

The present invention further relates to a method of measuring in a patient-derived biological sample the proportion of HIV using the CCR5 coreceptor compared to the proportion of HIV using the CXCR4 coreceptor which may comprise using an HTA to screen individual molecular clones of patient-derived HIV to determine the coreceptor usage of each individual clone and then comparing the number of molecular clones using either of each coreceptor to determine the proportion of HIV using the CCR5 coreceptor versus the CXCR4 coreceptor, where the method is used (a) to assess or predict the degree of HIV progression, (b) to determine when to start or change antiretroviral treatment, or (c) to monitor the efficacy of antiretroviral treatment and wherein the HTA produces either a first or second result, and further comprising comparing the number of molecular clones using either of each coreceptor to determine the proportion of HIV using the CCR5 coreceptor versus the CXCR4 coreceptor wherein the first result indicates HIV using the CCR5 coreceptor and the second result indicates HIV using the CXCR4 coreceptor.

The present invention further relates to a method of determining CCR5 and/or CXCR4 coreceptor usage of patient-derived HIV, which may comprise analyzing a portion of the genome of the patient-derived HIV with an HTA to detect coreceptor usage under conditions sufficient to reveal coreceptor usage.

In one embodiment, the patient-derived HIV may be isolated from a bodily fluid, blood, plasma, or spinal fluid.

In a further embodiment, the portion of the genome of the HIV may comprise the genetic determinates of coreceptor usage or a portion thereof. Furthermore, the genetic determinates may be derived from the env gene. Moreover, the portion of the genome of the HIV may be prepared by PCR using at least one set of oligonucleotide primers, which may include HTA6816F (SEQ ID NO: 26) and HTA7359R (SEQ ID NO: 27). In a further embodiment, a method of determining CCR5 and/or CXCR4 coreceptor usage of patient-derived HIV, may comprise analyzing a portion of the genome of the patient-derived HIV, wherein the portion of the genome of the HIV may be prepared by PCR using at least one set of oligonucleotide primers which includes V3-7092F (SEQ ID NO: 28) and V3-7232R (SEQ ID NO: 29) as second set of oligonucleotide primers.

The method of determining CCR5 and/or CXCR4 coreceptor usage of patient-derived HIV, may comprise the steps of: (a) amplifying a portion of the genome of the patient-derived HIV by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means, and (d) detecting the presence or absence or both of heteroduplex molecules; wherein the presence or absence of heteroduplex molecules reveals coreceptor usage. In one embodiment the method may comprise using a labeled probe derived from a known HIV-1 CCR5 clone. In another embodiment, the labeled probed may be derived from a known HIV-1 CXCR4 clone. A further embodiment might utilize a labeled probe which comprises a detectable moiety, a radioisotope, biotin, a fluorescent moiety, a fluorophore, a chemiluminescent moiety, or an enzymatic moiety.

The present invention further relates to the method of determining CCR5 and/or CXCR4 coreceptor usage of patient-derived HIV, comprising analyzing a portion of the genome of the patient-derived HIV with an HTA to detect coreceptor usage under conditions sufficient to reveal coreceptor usage wherein the method may be used (a) to determine a suitable antiretroviral treatment regiment, (b) to monitor the efficacy of antiretroviral treatment, or (c) to detect a shift back in coreceptor usage.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

These and other objects and embodiments are described in or are obvious from and within the scope of the invention, from the following Detailed Description.

BRIEF DESCRIPTION OF THE FIGURES

The following Detailed Description, given by way of example, but not intended to limit the invention solely to the specific embodiments described, may be best understood in conjunction with the accompanying drawings, in which.

DETAILED DESCRIPTION

Figure 1A:
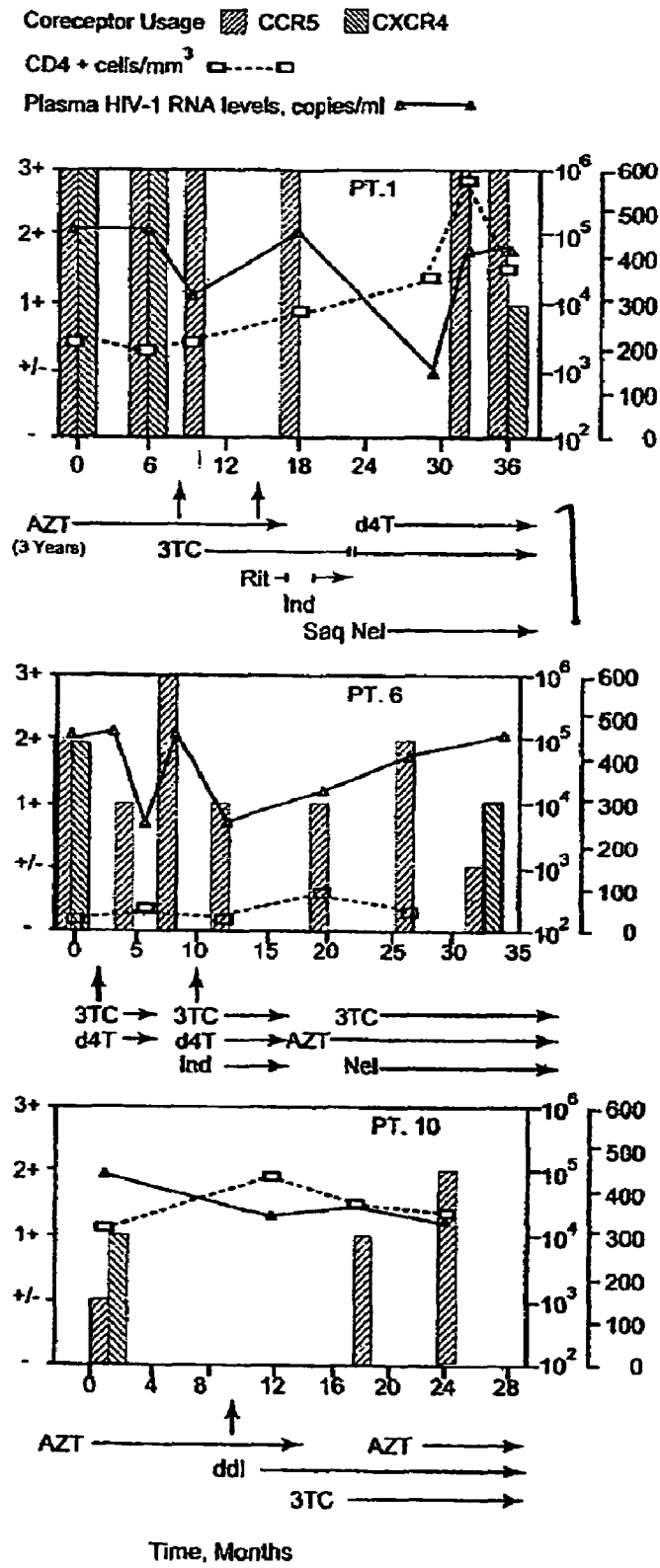
FIG. 1 depicts the effect of combination antiretroviral therapy on HIV-1 coreceptor use over time in representative study subjects. Patients 1, 2, 6, 8, and 10 received new, combination therapy and Patient 13 remained untreated. Arrows note the first time during the study period that a new combination of antiretroviral drugs was initiated. Two arrows appear if a patient received a two drug regimen first, then HAART. The duration of treatment with each agent is indicated. Drugs are abbreviated as follows: AZT, zidovudine; 3TC, lamivudine; Rit, ritonavir; Ind, indinavir; Saq, saquinavir; d4T, stavudine; Nel, nelfinavir; ddI, didanosine; ddC, zalcitabine; and Nev, nevirapine.
Figure 1B:
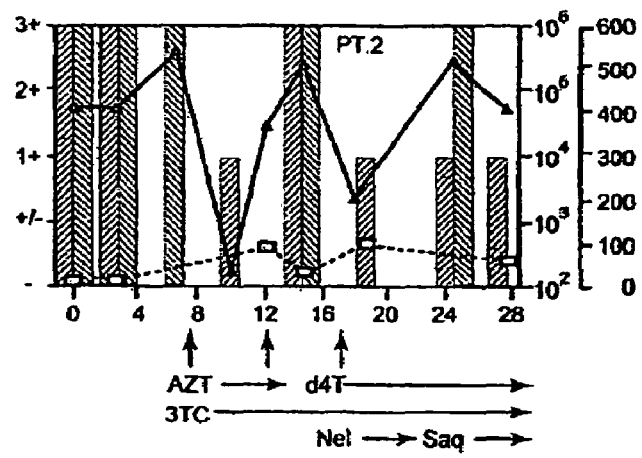
Figure 1B:
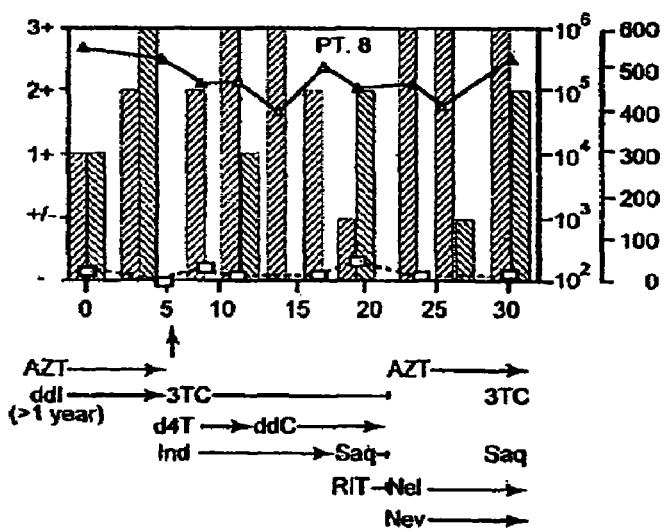
Figure 1B:
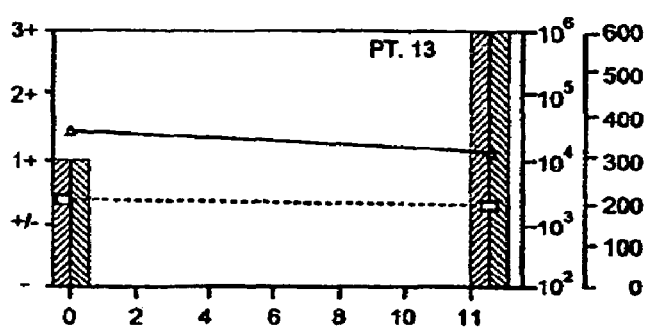

Evidence suggests that HIV coreceptor usage plays a critical role in viral tropism, pathogenesis, and disease progression. While CCR5-specific HIV are generally thought to be the transmitted form or genotype of HIV in vivo, the CXCR4-specific strains begin to emerge in a high percentage of patients once chronic infection is established. And, it is thought that CXCR4-specific strains are highly predictive of rapid depletion of CD4+ cells and an acceleration of HIV disease progression. The present inventors have unexpectedly discovered that in patients undergoing certain retroviral treatments for HIV infections, especially, HAART, the predominant populations of virus can be shifted back to the CCR5-specific HIV even after the emergence of the CXCR4-specific strains.

Thus, the present invention provides methods for detecting in an HIV-infected patient the coreceptor usage of the virus. This detection can be carried out at any point during disease progression, i.e. at an early period just after infection or at later periods including through the appearance of any AIDS related symptoms or close to the time of an AIDS-related death. The detection using the methods of the present invention can also be carried out during a retroviral treatment, such as during HAART, in order to monitor the disease progression and any responses to treatment in terms of the coreceptor usage of infectious population of HIV in the patient. The present invention provides methods, such as cell-based methods (e.g. cell fusion assays) and molecular-based methods (e.g. heteroduplex tracking assay) and any components therefor (e.g. indicator cell lines, cloning vectors, amplication tools such as DNA primers and PCR components), for monitoring, measuring, detecting, determining, and/or characterizing the coreceptor usage of the HIV population of an HIV-infected patient. These methods can be qualitative or quantitative. The quantitative methods of the invention, which can include the heteroduplex tracking assay, can provide an analysis of coreceptor usage for individual HIV clones from an HIV sample isolated from an infected patient to yield a quantitive, measured ratio of CCR5-specific to CXCR4-specific viruses. This ratio can also be expressed as "the QXR ratio", which is the ratio of the number of CCR5 clones identified compared to the total number of HIV clones analyzed.

One embodiment of the present invention relates to a diagnostic method to determine whether CXCR4 or CCR5 strains are present in a patient infected with HIV. The present invention further relates to a diagnostic method to determine whether CXCR4 or CCR5 strains are present in a patient comprising transforming cells with an HIV envelope gene (env) cloned from an infected patient, selectively fusing the cells with an indicator cell line expressing an HIV envelope-compatible coreceptor, and assaying for fusion. Cell surface envelope protein variants will selectively interact with either CCR5 or CXCR4. Fusion only occurs when an envelope protein interacts with a compatible coreceptor present on the surface of indicator cells. Cells expressing a particular envelope gene will fuse with either CCR5 or CXCR4 indicator cells, depending on the patient's envelope gene specificity. Therefore, whether fusion occurs with either CCR5 or CXCR4 indicator cells will indicate coreceptor usage. This method of the invention may be referred to in the present application as a "cell fusion assay," a "coreceptor cell-based assay," a "coreceptor assay," each of which are intended to be synonymous. Furthermore, the methods of the present invention relating to the use of indicator cell lines and cell fusion techniques can be referred hereinafter and throughout the application generally as "cell-based assays." Following the coreceptor assay, a "specificity assay" can be conducted to determine whether infection of the cell actually occurred. One suitable method to carry out the specificity assay can be, for example, to test the presumed infected cell line with anti-HIV antibodies, e.g. anti-HIV p24 antibodies (Kusunoki et al. (1999)), in comparison with a negative control, e.g. a cell line known not to be infected with HIV.

Other methods of the invention that rely on, inter alia, nucleic acid hybridization, can be referred to as "molecular-based assays," and include, for example, the heteroduplex binding assay of the invention.

The present invention may also include methods that combine both cell-based and molecular based methods and should not be construed to be limited to either one or the other approach.

A patient or subject can be any animal, preferably a mammal, and even more preferably a human, infected with HIV. The infectious AIDS virus can be, but is not limited to, HIV-1 and HIV-2.

An indicator cell line is a cell line comprising the CD4 receptor and a coreceptor or functional fragments thereof, suceptible to infection with HIV. Preferably the coreceptor is CXCR4 or CCR5. An indicator cell line can be, for example, HOS-CD4.CCR5 and HOS-CD4.CXCR4 (Deng et al. (1996); and Equils et al. (2000) J. Inf. Dis. 182:751-757), available from the AIDS Research and Reference Reagent Program Catalog. Other cell lines available from this catalog that are suitable for use as indicator cell lines include U373-MAGI (Fred Hutchinson Research Cancer Center); 3T3.T4, GHOST and U87.CD4 (New York University Medical Center). An indicator cell line can be any known in the art, such as described in Glushakova et al. (1999); and Dreyer et al. (1999). Although engineered primarily to screen HIV strains for drug sensitivity, the indicator cell lines described in WO 99/67429 are also also suitable for use as indicator cell lines.

An indicator cell line can be constructed by methods known in the art. Nucleic acids encoding HIV receptors or coreceptors, such as CD4, CXCR4 and/or CCR5, or functional fragments thereof capable of effecting receptor binding, can be cloned into recombinant vectors and introduced into cells of choice in vitro. HIV receptors and coreceptors or fragments thereof can be expressed by the recombinant vectors in cells of choice. Methods for generation and use of recombinant vectors in vitro are well known in the art. See Sambrook, Fritsch and Maniatis, Molecular Cloning, A Laboratory Manual, 2nd Ed., Cold Spring Harbor Laboratory Press, 1989 (e.g., procedures for isolating DNA, constructing recombinant vectors, transfecting and transforming cells and producing heterologous peptides).

The practice of the present invention will employ, unless otherwise indicated, conventional techniques of molecular biology, microbiology, recombinant DNA technology, genetic engineering, polypeptide and nucleic acid synthesis, nucleic acid sequencing, cloning technology, protein/DNA expression technology, and immunology, which are all within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I-IV (D. M. Weir and C. C. Blackwell eds 1986), each of which are incorporated herein by reference.

The term "or (a) fragment(s) thereof" as employed in the present invention and in context with polypeptides of the invention, comprises specific peptides, amino acid stretches of the polypeptides as disclosed herein. It is preferred that said "fragment(s) thereof" is/are functional fragment(s). The term "functional fragment" denotes a part of the above identified polypeptide of the invention which fullfils, at least in part, physiologically and/or structurally related activities of the polypeptide of the invention. It is also envisaged that the fragments, like the full-length polypeptides, can distinguish between HIV strains in effecting binding. The polypeptides of the present invention can be recombinant polypeptides expressed in eukaryotic cells, like mammalian cells.

Generally, recombinant DNA technology has enabled the expression of foreign (heterologous) proteins, such as HIV receptors or coreceptors, such as CD4, CXCR4 and/or CCR5, in cell lines of choice. In this process, a vector containing genetic material, e.g. nucleic acids encoding HIV receptors or coreceptors, directing a cell to produce a protein encoded by a portion of a heterologous DNA sequence is introduced into the host, and the transformed host cells can be fermented, cultured or otherwise subjected to conditions which facilitate the expression of the heterologous DNA, leading to the formation of large quantities of the desired protein. Plasmids are extensively used as vectors to clone DNA molecules. Most plasmid vectors are made by taking DNA from a variety of replicons (plasmids, bacteriophage chromosomes and bacterial chromosomes) and joining the DNA together (using restriction enzymes and DNA ligase) to form a plasmid that has an origin of replication, a selection marker (usually an antibiotic-resistance gene) and a promoter for expressing genes of interest in the required host cell. A vector can be, for example, as in U.S. Pat. Nos. 5,990,091 and 6,004,777, and as in PCT/US00/04203.

Furthermore, the recombinant vector can, in addition to the nucleic acid sequences of the invention (e.g. those encoding HIV receptors or coreceptors or functional fragments thereof), comprise expression control elements, allowing proper expression of the coding regions in suitable hosts. Such control elements are known in the art and can include a promoter, a splice cassette, translation initiation codon, translation and insertion site for introducing an insert into the vector. Preferably, the nucleic acid molecule is operatively linked to expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements can include transcriptional as well as translational enhancers, and/or naturally-associated or heterologous promoter regions. Possible regulatory elements permitting expression in for example mammalian cells comprise the CMV-HSV thymidine kinase promoter, SV40, RSV-promoter (Rous sarcoma virus), human elongation factor 1α-promoter, aPM-I promoter (Schaffer et al. (1999) Biochem. Biophys. Res. Commun. 260:416-425), or inducible promoter(s), like, metallothionein or tetracyclin, or enhancers, like CMV enhancer or SV40-enhancer. For the expression in prokaryotic cells, a multitude of promoters including, for example, the tac-lac-promoter or the trp promoter, has been described. Besides elements that are responsible for the initiation of transcription, such regulatory elements can also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-vitrogene), pSPORT1 (GIBCO BRL), Casper, Casper-HS43, pUAST, or prokaryotic expression vectors, such as lambda gt11.

Furthermore, depending on the expression system leader sequences capable of directing the polypeptide to a cellular compartment can be added to the coding sequence of the nucleic acid molecules of the invention and are well known in the art. The leader sequence(s) is assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusion protein including an C- or N-terminal identification peptide imparting desired characteristics, e.g., stabilization of expressed recombinant products. Once the vector has been incorporated into the appropriate cell line, the cells are maintained under conditions suitable for high level expression of the nucleotide sequences.

A cell can be transfected or transformed with a recombinant vector or plasmid. Methods of transformation and transfection are well known in the art. The transformed cells can be grown in fermentors and cultured according to techniques known in the art to achieve optimal cell growth. The resulting transformed or transfected cell lines are genetically modified with a nucleic acid molecule according to the invention or with a vector comprising such a nucleic acid molecule. The term "genetically modified" means that the cell comprises in addition to its natural genome a nucleic acid molecule or vector according to the invention which was introduced into the cell or host or into one of its predecessors/parents. The nucleic acid molecule or vector can be present in the genetically modified cell either as an independent molecule outside the genome, preferably as a molecule that is capable of replication, or it can be stably integrated into the genome of the cell.

The present invention can utilize any suitable prokaryotic or eukaryotic cell to construct an indicator cell line. Suitable prokaryotic cells are those generally used for cloning like *Escherichia coli* or *Bacillus subtilis*. Eukaryotic cells comprise, for example, fungal or animal cells, and are preferable for constructing an indicator cell line. Animal cells are preferably used for conducting the specificity assays of the invention. Suitable animal cells are, for instance, insect cells, vertebrate cells, preferably mammalian cells, such as e.g. GHOST, CHO, Hela, NIH3T3, MOLT-4, Jurkat, K562, HepG2, 3T3-L1 (and derivatives thereof), HIB-1B (Villena et al. (1998) Biochem. J. 331:121-127), HEK 293, PAZ6 (Strobel et al. (1999) Diabetologia 42:527-533). Further suitable cell lines known in the art are obtainable from cell line depositories, like the American Type Culture Collection (ATCC) and the AIDS Research and Reference Reagent Program Catalog. For example, HL3T1 and HeLa CD4+ (NIH) and HeLa T4+ (Columbia University) cell lines are available through the catalog and are easily adaptable for use in constructing an indicator cell line. Derivation of primary cells from an animal, preferably a mammal, and even more preferable a human, can also be undertaken for the purposes of establishing a suitable cell line.

Preferably, the cell line used in the present invention in the cell-based assays which are transformed with the receptor/coreceptor encoding vector of the invention is a blood cell, such as a macrophage or T cell, or an immortalized cell line derived therefrom.

Cloning strategies for isolating envelope genes of interest are well known in the art. See Sambrook, Fritsch and Maniatis, Molecular Cloning, A Laboratory Manual, 2nd Ed., Cold Spring Harbor Laboratory Press, 1989. Advantageously, envelope gene sequences can be obtained from a variety of patient tissues, including blood and mucosal tissues. High fidelity cloning of the samples above can be achieved by routine performance of multiple long RT-PCR reactions on limiting dilutions of RNA, followed by multiple PCR's on cDNAs obtained from each RT reaction. Performance of multiple PCR's on each cDNA preparation increases the likelihood of amplifying a different HIV-1 RNA species. These measures also decrease the chance of recombination.

The molecular-based methods of the present invention including, for example, the heteroduplex tracking assay, can include the step of preparing clones of HIV isolated from a patient, or more preferably clones of a portion of the HIV genome. The term "molecular clone" can refer to the cloning of a portion of the HIV genome, such as a gene or a portion of a gene, which can then be analyzed in accordance with the molecular-based methods of the invention, especially the heteroduplex tracking assay. For example, the invention relates to cloning a portion of the genome, i.e. preparing a molecular clone, containing genetic determinates of coreceptor usage, e.g. the env gene or a portion of the env gene, such as the third variable (V3) region of the env gene which corresponds or encodes the V3 domain of the gp120 glycoprotein. Technologies, components, and tools known to the ordinary skilled person can be used to clone such regions to be used in the molecular-based methods of the invention.

For example, using the heteroduplex tracking assay of the invention, it is possible to analyze individual cloned portions of the HIV genome, e.g. molecular clones of portions of the env gene containing genetic determinates for coreceptor usage, in order to quantitatively determine the proportion of HIV specific for the CCR5 coreceptor and those specific for the CXCR4 coreceptor. The ratio "QXR" is defined hereinafter and applies throughout the application as the number of clones identified as being specific to the CCR5 coreceptor compared to the total number of clones analyzed from a population of HIV contained in a sample of patient-derived HIV. It will be appreciated that during the course of disease progression that the pool of HIV in an infected individual can become a mixture of different strains which are different at the genetic level (i.e. have different "genotypes"). As alluded to earlier, it will be further understood by the skilled person that whether any particular HIV virus from a population of HIV in an infected individual is specific for CCR5 coreceptor or the CXCR4 coreceptor is dependent on the genetic determinates contained in that virus's genome, i.e. is reflected in that virus's genotype.

Clinical specimens comprising tissues and/or fluids from HIV-infected patients can be utilized for cloning envelope genes of interest, for example env, and portions thereof, especially portions containing genetic determinates of coreceptor usage. Advantageously, patient-derived virus can be obtained from sites in addition to peripheral blood, particularly those sites from which cultured virus cannot be obtained. For example, while circulating macrophages and CD4$^+$ T cells are the dominant reservoir of HIV-1, viral populations distinct from those in the peripheral blood exist in many tissue reservoirs, including the genital mucosa and lymphoid tissue.

Determination of cell fusion can be carried out using a variety of assays. The assay for cell fusion can be carried out, for example, with the use of an inducible reporter gene construct. Preferably, the inducible reporter gene construct is activated upon fusion with a cell containing a suitable transcriptional activator and/or transcription factor. A Tat-inducible reporter gene construct can be utilized, comprising a reporter gene linked to an HIV-1 LTR promoter. The reporter gene construct can encode a wide variety of colormetric, enzymatic and/or fluorescent reporter genes, such as the green fluorescent protein, placental alkaline phosphatase, firefly luciferase, β-galactosidase (encoded by the lacZ gene) and chloramphenicol acetyltransferase (encoded by the CAT gene). The assay for cell fusion can also be carried out using labeled antibodies, which specifically detect HIV envelope proteins, and CXCR4 or CCR5 coreceptors on or within a fused cell. This method can be combined with cell sorting techniques, to separate populations of fused cells.

The present invention further relates to a diagnostic method to determine whether CXCR4 or CCR5 strains are present in a patient comprising transforming cells containing an HIV Tat-activatable reporter gene construct with an HIV envelope gene variant cloned from an infected patient, selectively fusing the cells with an indicator cell line containing a constitutively active that gene and an HIV envelope-compatible coreceptor, and assaying for fusion by detection of reporter gene expression. Upon fusion of cells mediated by the envelope variant-coreceptor interaction, Tat inducible reporter gene expression will be activated.

The present invention further relates to a diagnostic method to determine whether CXCR4 or CCR5 strains are present comprising obtaining patient-derived virus and assaying the virus for coreceptor use (i.e. coreceptor assay).

Patient-derived virus includes, but is not limited to, primary viral isolates, biological clones, and molecular clones. Patient-derived viruses can be obtained from clinical specimens comprising any fluid or tissue obtained from an HIV infected individual, such as peripheral blood.

Patient-derived primary viral isolates can be obtained by methods known in the art. For instance, peripheral blood of HIV-infected individuals can be separated into plasma and cell components by methods known in the art. Fang et al. (1995) Proc. Natl. Acad. Sci. USA 92:12110-4. Primary viral isolates of HIV-1 can be obtained by co-culture with normal donor peripheral blood mononuclear cells (PBMCs). Fang et al. (1995). Titration of viral isolates in PBMCs can be carried out, for example, by using the methods previously described by Fang et al (1995).

Biological clones can be derived from primary isolates by methods known in the art, such as short-term limited dilution cloning. Connor et al. (1997). Quantitation of HIV-1 RNA in plasma can be carried out, for example, by using NucliSens (Organon Teknika Corp., Durham, N.C.). Quantitation methods can set a lower limit, preferably at $\leq 80$ copies/ml.

Biological clones are applicable for determining the proportion of virus using each receptor. It is desirable to quantitate the proportion of virus using each coreceptor when rigorously comparing coreceptor use over time.

Assaying for coreceptor use can comprise inoculating indicator cell lines with primary isolates and/or biological clones (i.e. coreceptor assay) followed by determining whether infection occurred (i.e. specificity assay).

For purposes of conducting the coreceptor assay, the indicator cells can be seeded, for example, onto 12-well plates and inoculated, preferably after 12-36 hours, such as 24 hours, with a standard quantity of titered virus, preferably $10^2$ TCID$_{50}$ of first passage primary viral isolates or biological clones.

For purposes of conducting the coreceptor assay CCR5— and CXCR4-specific positive control viruses can be employed, such as HIV JR-FL and LAV/HTLV-IIIB. Infection with CCR5- and CXCR4-specific positive control viruses can be carried out in parallel to infection with primary isolates and/or biological clones. The positive control virus strains preferably have a known genomic sequence and the genetic determinates for CXCR4-specificity are known. Uninoculated cells can be negative controls.

Prior to conducting the coreceptor assay, indicator cell lines can be tested by inoculation with duplicate primary and control isolates to eliminate the possibility of any artifacts resulting from infection via low levels of endogenous coreceptor expression.

Following the coreceptor assay, a specificity assay is conducted to determine whether infection occurred. A suitable method for determining infection of the indicator cell line can be measurement of a complex formation. The measurement of a complex formation is well known in the art and comprises, inter alia, heterogeneous and homogeneous assays. Homogeneous assays comprise assays wherein the binding partners remain in solution. Heterogeneous assays comprise assays like, inter alia, immuno assays, for example, ELISAs, RIAs, IRMAs, FIAs, CLIAs or ECLs. Such assays are, inter alia, disclosed in U.S. Pat. No. 5,854,003 or in U.S. Pat. No. 5,639,858. Specificity assays like ELISA are preferred. Any specificity or detection step of the present invention can be assisted by computer technology or other means of automation, including flow cytometry.

Another suitable method for determining whether infection of the indicator cell line occurred is contacting an epitope of HIV and identifying whether binding occurs, without binding to a control. In particular, the specificity assay of the invention can be carried out by employing antibodies directed against the HIV p24 antigen, as described by Kusunoki et al. (1999) Nucleosides Nucleo. 18:1705, or by using commercial ELISA assay kits, available, for example, from NEN Life Science Products, Boston, Mass. (USA).

Therefore, the coreceptor assay of the invention can be easily performed using the disclosure herein and methods known in the art such as described herein.

The present invention yet further relates to a diagnostic method to monitor shifts in coreceptor use associated with changes in HIV disease progression.

The present invention further relates to a diagnostic method to monitor shifts in coreceptor use associated with changes in HIV disease progression comprising transforming cells with an HIV envelope gene variant cloned from an infected patient, selectively fusing the cells with an indicator cell line expressing an HIV envelope-compatible coreceptor, and assaying for fusion.

The present invention further relates to a diagnostic method to monitor shifts in coreceptor use associated with changes in HIV disease progression comprising transforming cells containing an HIV Tat-activatable reporter gene construct with an HIV envelope gene variant cloned from an infected patient, selectively fusing the cells with an indicator cell line containing a constitutively active that gene and an HIV envelope-compatible coreceptor, and assaying for fusion by detection of reporter gene expression.

The present invention further relates to a diagnostic method to monitor shifts in coreceptor use associated with changes in HIV disease progression comprising determining CXCR4 coreceptor use, CCR5 coreceptor use, and a ratio of HIV using the CXCR4 coreceptor compared to HIV using the CCR5 coreceptor.

The present invention further relates to a diagnostic method to monitor shifts in coreceptor use associated with changes in HIV disease progression comprising obtaining patient-derived virus from a clinical specimen and deriving biological clones therefrom, assaying the clones for coreceptor use, and applying a method of quantitating the proportion of virus in the clinical specimen that uses each coreceptor.

In a preferred embodiment, the coreceptor assay includes quantifying the proportion of virus using each coreceptor. Quantitation with the coreceptor assay can be performed in a number of ways, including determining coreceptor specificity of multiple biologic clones, preferably at least 5; determining the viral sequence of portions of the HIV envelope gene, particularly the V3 region which predicts coreceptor use or any genetic region containing genetic determinates of coreceptor usage; or assaying a viral primary isolate using a semiquantitative method and applying a statistical method, for example, as described herein.

In an embodiment, determination of the proportion of CCR5 or CXCR4 virus using the cell-based assays of the invention can be carried out by determining coreceptor specificity of multiple biologic clones. A system devised for determining coreceptor specificity through the use of an indicator cell line is provided herein above. Biologic clones derived from the patients' primary viral isolates can be assayed for coreceptor use by employing an indicator cell line, such as the HOS-CD4+ cell line.

In another embodiment, determination of the proportion of CCR5 or CXCR4 virus can be carried out by determining the viral sequence of portions of the HIV envelope gene, particularly the V3 region which predicts coreceptor use or any region having genetic determinates of coreceptor usage. The envelope protein can be gp120, gp 160 or a portion thereof. Envelope sequences are predictive of coreceptor use on the basis of the overall charge of the V3 loop and the presence of basic or acidic residues at positions 275 and 287 of the env gene. Bhattacharya et al. (1996) AIDS Res. Hum. Retrovir. 12:83-90; and Hung et al. (1999) J. Virol. 73:8216-26. An example of a system devised for determining the viral sequence of portions of the HIV envelope gene is provided herein. Reverse transcriptase polymerase chain reaction can be used to amplify the V3 region of the env gene from plasma or other body fluid. Amplified products can be sub-cloned, verified by restriction digestion, and sequenced.

It is furthermore envisaged, that the diagnostic method involves the use of micro-chips comprising nucleic acid molecules encoding a envelope protein, or a fragment thereof, preferably a V3 region fragment, especially including genetic determinates of coreceptor usage, on "gene chips"; or an envelope protein, or a fragment thereof, preferably a V3 region fragment, on "protein-chips" (See U.S. Pat. Nos. 6,066,454; 6,045,996; 6,043,080; 6,040,193; 6,040,138; 6,033,860; 6,033,850; 6,025,601; 6,022,963; 6,013,440; 5,968,740; 5,925,525; 5,922,591; 5,919,523; 5,889,165; 5,885,837; 5,874,219; 5,858,659; 5,856,174; 5,856,101; 5,843,655; 5,837,832; 5,834,758; 5,831,070; 5,770,722; 5,770,456; 5,753,788; 5,744,305; 5,733,729; 5,710,000; 5,631,734; 5,599,695; 5,593,839; 5,578,832; and 5,556,752). Diagnostic gene chips can comprise a collection of polypeptides that specifically detect a envelope protein, or fragments thereof, preferably V3 region fragments; or nucleic acid molecules that specifically detect a nucleic acid molecule encoding a envelope protein, or fragments thereof, preferably V3 region fragments; all of which can be used for the purposes of determining coreceptor use. The envelope protein can be gp 160, gp120, or a portion thereof.

Determination of the proportion of CCR5 or CXCR4 strains from patient-derived virus can be carried out using a quantitative statistical method. An example of a system devised for quantitation of the proportion of CCR5 and CXCR4 strains in a clinical specimen is provided herein. In this system, QXR is a continuous, nonlinear variable between one and zero derived from the results of coreceptor use by biologically and molecularly cloned virus; it describes the mixed proportion of viruses using CCR5 and CXCR4. A QXR value near one describes a population of viruses that almost all use CCR5; a value near zero describes a population that almost all use CXCR4.

More in particular, this system comprises a variable, QXR, that is constructed as the proportion of strains using CCR5. QXR=1 represents an isolate in which all strains prefer the CCR5 coreceptor but QXR=O indicates that all prefer CXCR4. QXR values can be assessed by utilizing qualitative assay data derived from patient-derived virus and sequences of the V3 portion of the env gene in patient-derived virus. QXR values can be constructed by relating data derived from the same patient sample by using three different analyses: biologic cloning, V3 sequencing, and semiquantitative assays of primary isolates. To construct QXR values, the proportion of biologic and, if available, molecular clones using CCR5 at each time point is calculated, then the proportion is linked to the semiquantitative coreceptor use score (−to 3+) of primary isolates obtained simultaneously. The data are transformed to approximate a Poisson distribution. Poisson regression analysis can then be performed to determine the factors associated with changes in QXR values.

The Wilcoxon Rank Sum Test can be used to make comparisons between the magnitude of log viral level, CD4+ counts, and QXR values. Data for factors relating to changes in QXR values can be analyzed by multivariate Poisson regression. Variables can include log HIV-1 RNA levels, changes in viral levels, CD4+ cell counts, changes in CD4+ cell counts, and indicator variables for levels of antiretroviral therapy.

Application of the diagnostic methods to detect and/or monitor shifts in coreceptor use is useful for predicting disease prognosis over time.

The present invention also relates to a diagnostic method to determine whether CXCR4-specific strains are present in patients infected with HIV undergoing antiretroviral therapy.

The present invention further relates to a diagnostic method to determine whether CXCR4 or CCR5 strains are present in patients infected with HIV undergoing antiretroviral therapy comprising transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention further relates to a diagnostic method to determine whether CXCR4 or CCR5 strains are present in patients infected with HIV undergoing antiretroviral therapy comprising transforming cells containing an HIV Tat-activatable reporter gene construct with an HIV envelope gene variant cloned from an infected patient, selectively fusing the cells with an indicator cell line containing a constitutively active that gene and an HIV envelope-compatible coreceptor, and assaying for fusion by detection of reporter gene expression before and/or after initiating antiretroviral therapy.

The present invention also relates to a diagnostic method to determine whether CXCR4-specific strains are present in HIV-infected patients receiving antiretroviral therapy comprising obtaining patient-derived virus and assaying for coreceptor use before and/or after initiating antiretroviral therapy.

The present invention also relates to a diagnostic method to monitor the suppression of CXCR4-specific strains in HIV-infected patients receiving antiretroviral therapy.

The present invention further relates to a diagnostic method to monitor the suppression of CXCR4-specific strains in HIV-infected patients receiving antiretroviral therapy comprising transforming cells with an HIV envelope gene variant cloned from an infected patient, selectively fusing the cells with an indicator cell line expressing an HIV envelope-compatible coreceptor, and assaying for fusion before and/or after initiating antiretroviral therapy.

The present invention also relates to a diagnostic method to monitor the suppression of CXCR4-specific strains in HIV-infected patients receiving antiretroviral therapy comprising transforming cells containing an HIV Tat-activatable reporter gene construct with an HIV envelope gene variant cloned from an infected patient, selectively fusing the cells with an indicator cell line containing a constitutively active that gene and an HIV envelope-compatible coreceptor, and assaying for fusion by detection of reporter gene expression before and/or after initiating antiretroviral therapy.

The present invention further relates to a diagnostic method to monitor the suppression of CXCR4-specific strains in HIV-infected patients receiving antiretroviral therapy comprising determining CXCR4 coreceptor use, CCR5 coreceptor use, and a ratio of HIV using the CXCR4 coreceptor compared to HIV using the CCR5 coreceptor before and/or after initiating antiretroviral therapy.

The present invention also relates to a diagnostic method comprising obtaining patient-derived virus from a clinical specimen and deriving biological clones therefrom, assaying the clones for coreceptor use, and applying a method for quantitating the proportion of virus in the clinical specimen that uses each coreceptor before and/or after initiating antiretroviral therapy.

The present invention yet further relates to a diagnostic method to monitor the suppression of CXCR4-specific strains in HIV-infected patients receiving antiretroviral therapy comprising determining the sequence of HIV envelope gene before and/or after initiating antiretroviral therapy.

Application of the diagnostic method further provides a way to monitor the effectiveness of antiretroviral therapy. Aspects of antiretroviral therapy that can be monitored, for example, are development of drug resistance and/or sensitivity. The diagnostic methods of the invention can be applied before initiating antiretroviral therapy to determine a suitable antiretroviral treatment regimen. The diagnostic methods of the claimed invention can also be applied after initiating antiretroviral therapy to monitor efficacy of a viral treatment regimen and where efficacy of the treatment is directly related to decrease of CXCR4 coreceptor use. The diagnostic methods of the invention can also be used to determine whether a putative antiretroviral therapy or treatment is efficacious in decreasing CXCR4 coreceptor use.

Antiretroviral therapy can include, but is not limited to, HAART, protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including at least one protease inhibitor, or at least a reverse transcriptase inhibitor and a protease inhibitor; or at least two reverse transcriptase inhibitors with at least one protease inhibitor.

Typical reverse transcriptase inhibitors include nucleoside analogs, such as, but not limited to, AZT (Zidovudine), ddi (didanosine), ddc (zalcitabine), D4T (stavudine), 3TC (lamivudine), Ziagen (abacavir), combivir (mix of AZT and 3TC), and non-nucleoside analogs, e.g., viramune (nevirapine), rescriptor (delavirdine), sustiva (efavirenz). Protease inhibitors include invirase (saquinavir), norvir (ritonavir), crixivan (indinavir), viracept (nelfinavir), agenerase (amprenivir), kaletra (lopinavir and ritonavir) and fortovase (saquinavir in a soft gelatin form). Thus, HAART can also be "triple cocktail" therapy—a three drug regimen to combat HIV wherein one of the three drugs is usually a protease inhibitor (and the other two are usually reverse transcritase inhibitors).

One skilled in the art (e.g. a physician, preferably specializing in the treatment of infectious disease) would use appropriate judgment and discretion in determining how often to apply the diagnostic methods to a test subject (e.g. a patient). Frequency of application can vary, depending on, for example, the age, sex, type of antiretroviral therapy administered to, or stage of disease progression in, a test subject.

One skilled in the art further understands the results of the diagnostic method to provide additional information about the stage of disease progression or therapeutic efficacy, depending on the amount of CXCR4 specific strain specificity of a test subject.

Application of the diagnostic methods to detect and/or monitor shifts in coreceptor use is useful for assessing the effectiveness of antiretroviral therapy.

The present invention further relates to a composition that is a diagnostic composition which can be, for example in the form of a kit.

The diagnostic composition can comprise the components as defined herein above wherein said components are bound to/attached to and/or linked to a solid support. It is furthermore envisaged, that the diagnostic composition comprises nucleic acid sequences encoding a envelope protein, or a fragment thereof, preferably a V3 region fragment; or indicator cell lines of this invention; all of which can be contained on micro-chips identifiable with a suitable means for detection.

Solid supports are well known in the art and comprise, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. Suitable methods for fixing/immobilizing cells, nucleic acid sequences, or polypeptides of the invention are well known and include, but are not limited to ionic, hydrophobic, covalent interactions and the like.

The diagnostic composition of the present invention can be advantageously used as a kit, inter alia, for carrying out the method of the invention and could be employed in a variety of applications, e.g., as diagnostic kits, as research tools. Additionally, the kit of the invention can contain means for detection suitable for scientific, medical and/or diagnostic purposes. The manufacture of the kits follows preferably standard procedures that are known to the person skilled in the art. Kits can advantageously include instructions for use and/or admixture of ingredients.

In the present invention, it is additionally understood that HIV is a lentivirus, and the skilled artisan can readily understand that from the teachings herein, and the knowledge in the art, within the ambit of the invention are herein embodiments wherein the virus is a lentivirus other than HIV, including SIV and FIV, as in U.S. Pat. Nos. 5,863,542 and 5,766,598, and wherein the coreceptors are analogous (e.g. homologous) to CCR5 and CXCR4. As used herein, acquired immunodeficiency virus is interchangeable with HIV and encompasses other such viruses such as SIV and FIV. One skilled in the art can follow the teachings in the art to identify analogous coreceptors.

Another aspect of the present invention relates to the use of molecular-based methods to qualitatively and/or quantitatively evaluate patient-derived HIV for coreceptor utilization. In one embodiment, a heteroduplex tracking assay is used to qualitatively and/or quantitatively evaluate, e.g. monitor, measure, determine, detect, coreceptor usage of patient-derived HIV. It will be appreciated that the molecular-based methods may be employed at any point during disease progression, i.e. early or late HIV infection, concurrent with AIDS related symptoms, or close to the time of an AIDS-related death. The detection using the methods of the present invention can also be carried out during a retroviral treatment or therapy, such as during HAART, in order to monitor the disease progression and any responses to treatment in terms of the coreceptor usage of infectious population of HIV in the patient. Other retroviral treatments are known and have been mentioned previously. They include, but are not limited to, protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including at least one protease inhibitor, or at least a reverse transcriptase inhibitor and a protease inhibitor; or at least two reverse transcriptase inhibitors with at least one protease inhibitor.

The heteroduplex tracking assay of the invention can be carried out substantially in accordance with the guidance of Delwart et al. (J. Virol. (1994) 68:6672-6683), Delwart et al. (Science (1993) 262:1257-1261), Delwart et al. (PCR Methods and Applications 4:S202-S216 (19950 Cold Springs Harbor), and U.S. Pat. No. 5,851,759 (Weiner), each of which are incorporated in their entireties by reference.

The heteroduplex tracking assay can be used to analyze a portion of the HIV-1 genome encompassing determinates of coreceptor utilization to understand, determine, monitor, or detect coreceptor usage. Genetic determinates of HIV-1 coreceptor utilization can be found in the envelope gene (env), with key determinates being found in the third variable (V3) domain of the gp120 glycoprotein.

The heteroduplex tracking assay of the invention can be carried out generally, while not being limited thereto, according to the basic steps of: (a) obtaining HIV viral RNA from the patient, (b) amplifying, e.g. PCR and/or reverse transcription, a portion of the viral genome containing genetic determinates of coreceptor usage, e.g. a genomic portion comprising the V3 domain of the gp120 envelope glycoprotein, (c) forming heteroduplexes and/or homoduplexes with labeled nucleic acid-based probes prepared from a corresponding genomic region of a known HIV strain, e.g. the same genomic portion comprising the V3 domain of gp120, and (d) subjecting the heteroduplexes and homoduplexes to a separation system, e.g. electrophoresis through non-denaturing polyacrylamide gels, wherein the heteroduplexes and homoduplexes have differing and distinguishable mobilities that results in characteristic mobility patterns, e.g. a electrophoretic pattern, such that the coreceptor usage can be determined.

For example, the presence of an electrophoretic pattern characteristic of heteroduplexes can indicate the presence of CXCR4-specific viruses in the HIV sample. Alternately, the presence of an electrophoretic pattern characteristic of homoduplexes can indicate the presence of only CCR5-specific viruses. And, a pattern characteristic of both homoduplexes and heteroduplexes can indicate that the HIV sample contains a mixed population of CCR5-specific and CXCR4-specific viruses. The heteroduplex tracking assay can be performed at any point during disease progression or during, before, or after administering antiretroviral therapy. Further, the heteroduplex tracking assay can be carried out either to attain qualitative results or quantitative results.

Method for obtaining and/or extracting HIV RNA from patient-derived samples are well-known. Also, the step of amplifying a portion of the viral genome containing genetic determinates of coreceptor usage a known in the art, and include, for example reverse transcriptase PCR (RT-PCR). Following RT-PCT, further rounds of PCR can be used to further amplify desired portions of the genome, especially regions containing genetic determinates of coreceptor usage.

The technique of PCR is well known in the art. By "PCR" is meant herein the polymerase chain reaction (PCR) technique, disclosed by Mullis in U.S. Pat. No. 4,683,195 (Mullis et al) and U.S. Pat. No. 4,683,202, incorporated herein by reference. The following U.S. patents may also be referenced for information relating to PCR generally: U.S. Pat. Nos. 6,316,192; 6,309,837; 6,300,073; 6,300,072; 6,284,455; 6,270,977; 6,270,966; 6,268,143; 6,261,431; 6,251,607; 6,232,079; 6,225,093; 6,218,153; 6,207,425; 6,183,963; 6,180,372; 6,146,834; 6,087,097; 6,072,369; 6,068,974; 6,063,563; 6,046,039; 6,031,960; 6,017,699; 6,015,664; 6,015,534; 6,001,612; 5,972,602; 5,909,468; 5,905,732; 5,888,740; 5,883,924; 5,869,318; 5,853,991; 5,837,468; 5,827,657; 5,824,516; 5,824,479; 5,814,489; 5,780,222; 5,776,686; 5,774,497; 5,759,822; 5,716,784; 5,712,125; 5,712,090; 5,691,146; 5,681,741; 5,618,703; 5,618,702; 5,565,340; 5,556,774; 5,556,773; 5,527,510; 5,487,993; 5,426,026; 5,393,657; 5,364,790; 5,364,758; 5,229,297; and 5,187,060; each of which are incorporated herein in their entirety by reference.

It will be appreciated that the heteroduplex tracking assay is based on the observation that when sequences were amplified by nested PCR from peripheral blood mononuclear cells of infected individuals, related DNA products coamplified from divergent templates could randomly reanneal to form heteroduplexes that migrate with reduced mobility in neutral polyacrylamide gels. Using these techniques, one can establish genetic relationships between multiple viral DNA template molecules, such as the different genetic types (i.e. different genotypes) of HIV utilizing the different coreceptors. The HTA of the invention can be described as utilizing a first PCR product as a labeled probe, e.g. radioactive, which is mixed with an excess ("driver") of an unlabeled PCR product from a different source, i.e., the source for which typing or analysis of is desired, e.g. the PCR product defining the portion of the HIV genome with the coreceptor genetic determinates. The probe sequences are then "driven" completely into heteroduplexes with the driver, and are separated, e.g. by gel electrophoresis, on the basis of size. An autoradiogram, for example, of the resulting polyacrylamide gel reveals these heteroduplexes and provides a visual display of the relationship between the two virus populations under study. The fact that heteroduplexes migrate with distinct mobilities indicates that the strand-specific composition of mismatched and unpaired nucleotides affects their mobility.

A "heteroduplex" encompasses a doublestranded DNA molecule having complementary strands at which one strand (the "target strand", i.e. a single strand of DNA from the PCR product of the HIV genome) contains one or more mismatched or an unpaired nucleotide base. For example, a heteroduplex can form by mixing together a labeled probe (e.g. a double-stranded DNA PCR product of a portion of the envgene of CCR5-specific HIV) and a PCR product of a target sequence (e.g. a double-stranded DNA PCR product of the corresponding portion of the env gene of a CXCR4-specific HIV) such that complementary single-stranded DNA of each PCR product are combined together as a new, double-stranded molecule. However, since the PCR product from the CXCR4-specific HIV will contain genetic determinates characteristic of CXCR4 type viruses, its nucleotide sequence will vary at specific locations with respect to the probe PCR product (which is derived from CCR5). These differences in sequence result in a heteroduplex which has reduced mobility during electrophoresis with respect to homoduplexes owing to a reduced level of base-pairing in the molecule. In contrast, the "homoduplex" may be formed between complementary strand pairs derived from a probe PCR product and a target PCR product such that their nucleotide sequences are the same. For example, a homoduplex will form where both the PCR product and the target PCR product are derived from CCR5-specific HIV.

In another embodiment, the heteroduplex tracking assay can comprise the steps of (a) amplifying an individual molecular clone or a portion thereof by PCR to provide amplified DNA comprising the genetic determinates of coreceptor usage or a portion thereof; (b) forming a population of heteroduplex molecules by contacting the amplified DNA with a labeled probe complementary to the amplified DNA under conditions sufficient to form heteroduplexes; (c) separating the population of heteroduplex molecules using a separation means: and (d) detecting the presence or absence of heteroduplex molecules; wherein the presence or absence of heteroduplex molecules reveals coreceptor usage. In one embodiment, the labeled probe may be derived from a known HIV-1 CCR5 clone. In another embodiment, the labeled probe may be derived from a known HIV-1 CXCR4 clone. The labeled probe can comprise a detectable moiety, a radioisotope, biotin, a fluorescent moiety, a fluorophore, a chemiluminescent moiety, or an enzymatic moiety. Appropriate labels and their methods of preparation are well-known.

Another embodiment of the invention relates to kits for carrying out the heteroduplex tracking assay of the invention to analyze the coreceptor usage of patient-derived HIV during the course of disease progression or during, before, and/or after administering an antiviral treatment or therapy, such as, for example, HAART. The kits can include all necessary components to carry out the heteroduplex tracking assay of the invention, including instructions/directions, for example, components for isolating HIV RNA from patients, RT-PCT and PCR primers, labeling components, negative and/or positive controls, e.g. control HIV cDNAs or RNA or PCR products, gel electrophoresis components, enzymes and/or proteins necessary for carrying out the assay, e.g. PCR polymerases. Genotyping kits for genotyping with the heteroduplex tracking assay are described in U.S. Pat. No. 5,851,759 which is incorporated by reference herein in its entirety.

It will be understood that the heteroduplex tracking assay of the invention can be used to provide both qualitative and quantitative information. First, qualitative information can be derived using the HTA of the invention by analyzing the whole HIV population derived from an infected patient to determine whether the isolated population of HIV is CCR5-specific, CXCR5-specific, or mixture of both types. It will be appreciated that qualitative information is based on the whole or substantially the whole HIV population rather than individual clones therefrom. On the contrary, quantitative information can be derived using the HTA of the present invention by analyzing individual HIV clones (e.g. cloned portions of the HIV genome of a plurality of individual HIV viruses from the isolated whole population of HIV from the infected patient) with respect to their coreceptor usage and determining a ratio of CCR5-specific to CXCR4-specific clones. In one embodiment, the invention relates to determining the QXR ratio: the number of HIV clones that are identified as CCR5-specific compared to the total number of clones analyzed. It will be appreciated that the HIV clone can refer to the cloned PCR product or amplified portion of the HIV genome that is analyzed by HTA and which contains genetic determinates of the coreceptor preference.

Figure 5:
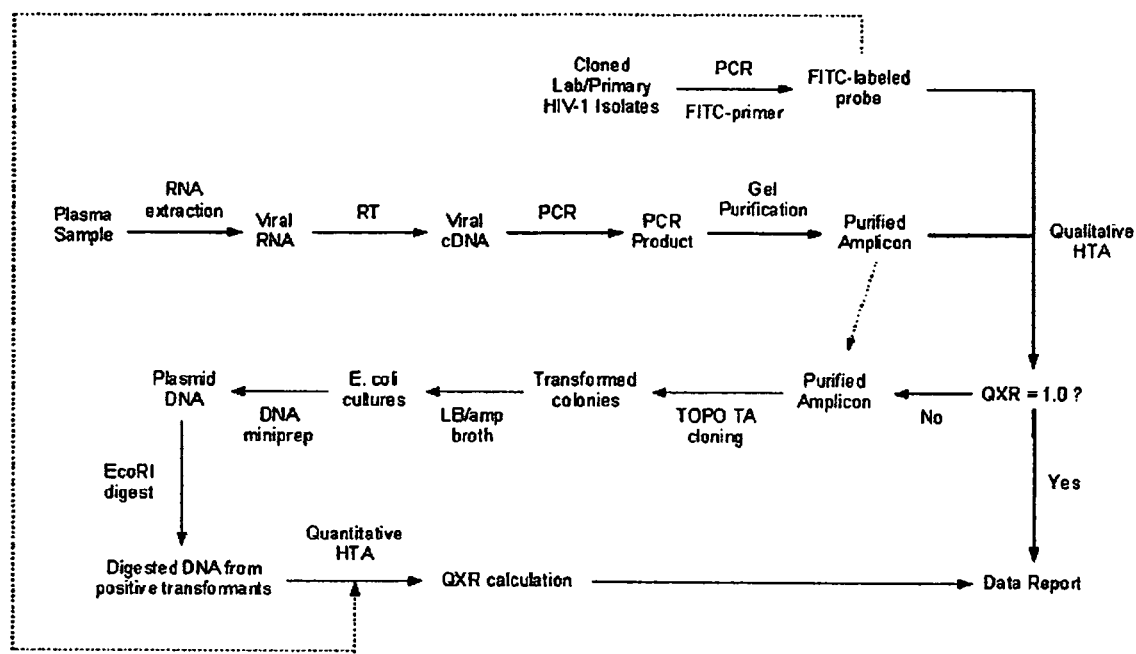
FIG. 5 provides a graphical illustration of the various steps of the heteroduplex tracking assay (HTA) of the invention which provides for both qualitative and quantitative analysis of HIV coreceptor usage.

FIG. 5 depicts a flow chart showing the qualitative and quantitative aspects of the HTA of the present invention. First, HIV RNA is extracted from the infected patient. Next, RT-PCR is carried out to obtain HIV cDNA, from which a PCR product (i.e. PCR amplicon) containing genetic determinates for coreceptor usage is amplied using PCR. The PCR product is then gel purified. Presumably, the PCR product will be a mixed population of molecules—those genotypic for either CCR5 or CXCR4 coreceptors—whenever the isolated HIV sample contains both types of viruses. Next, the PCR product is analyzed by the HTA of the invention, which includes generally the steps of mixing together a labeled probe (e.g. a PCR product corresponding to same region in a known CCR5 strain as the amplified target PCR amplicon to be analyzed) and the amplified target PCR amplicon to form homo- or heteroduplexes. The molecules are then separated by gel electrophoresis, for example, on a 12% polyacrylamide gel. Electrophetic techniques are well known in the art.

Figure 6:
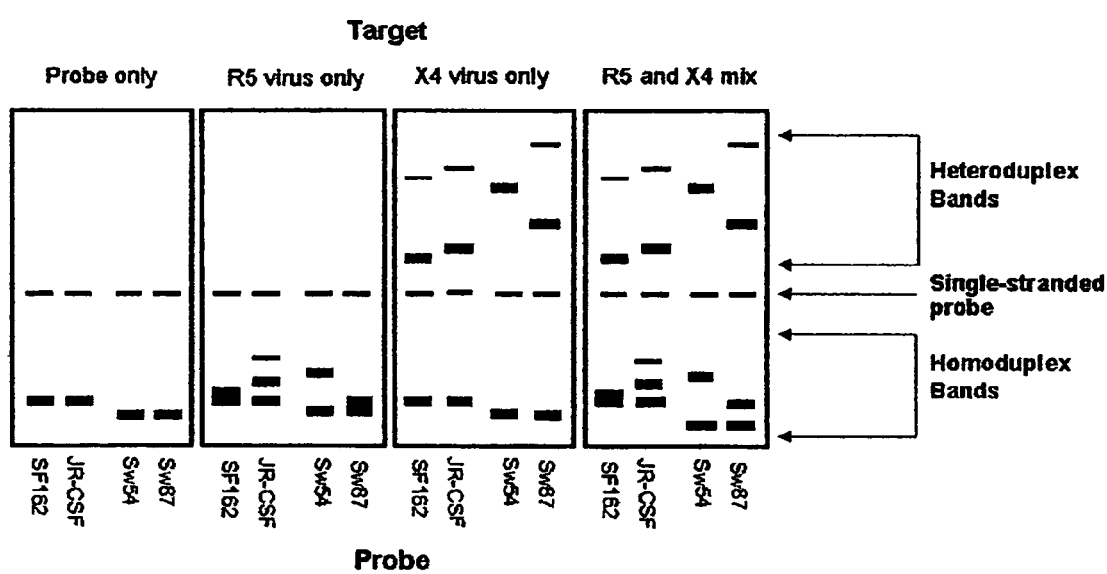
FIG. 6 provides a schematic representation of heteroduplex tracking assay (HTA) analysis of four different targets, including probe only, CCR5-specific HIV only, CXCR4-specific HIV only, and a mixture or "quasispecies" of both CCR5-specific and CXCR4-specific HIV.

Exemplarly results are represented in FIG. 6. The figures shows four panels of schematic electropherograms. The first panel is the negative control, i.e. labeled probe only. The second panel shows the result of HTA of a CCR5 virus. The third panel shows the result of HTA of a CXCR4 virus. And, the fourth panel shows the result of HTA of a mixture of CCR5 and CXCR4 viruses. Four different probes (each based on a CCR5-specific control virus) were used to test each HIV sample. The gels show heteroduplex band patterns only for those HIV samples containing CXCR4-specific viruses.

In another embodiment, the present invention further relates to a method of measuring in a patient-derived biological sample the proportion of HIV using the CCR5 coreceptor compared to the proportion of HIV using the CXCR4 coreceptor comprising using an HTA to screen individual molecular clones of patient-derived HIV to determine the coreceptor usage of each individual clone and then comparing the number of molecular clones using either of each coreceptor to determine the proportion of HIV using the CCR5 coreceptor versus the CXCR4 coreceptor, where the method is used (a) to assess or predict the degree of HIV progression, (b) to determine when to start or change antiretroviral treatment, or (c) to monitor the efficacy of antiretroviral treatment and wherein the HTA produces either a first or second result, and further comprising comparing the number of molecular clones using either of each coreceptor to determine the proportion of HIV using the CCR5 coreceptor versus the CXCR4 coreceptor wherein the first result indicates HIV using the CCR5 coreceptor and the second result indicates HIV using the CXCR4 coreceptor.

The present invention is additionally described by way of the following illustrative, non-limiting Examples, that provide a better understanding of the present invention and of its many advantages.

EXAMPLES

The Examples show that HAART not only reduces the quantity of virus but also affects HIV-1 coreceptor use. Briefly, methods were devised for quantifying the proportion of viruses in patient-derived virus that used each coreceptor and monitoring the effect of combination antiretroviral therapy, particularly HAART, on coreceptor use.

Example 1

Study Population

Coreceptor use was examined in twenty-two women who participated in two prospective studies of HIV-1 infection. Nineteen were enrolled in the Bronx-Manhattan site of Women's Interagency HIV Study (WIHS), a National Institutes of Health (NIH) multicenter study of the natural history of HIV-1 infection in women. Three took part in a study of HIV-1 pathogenesis performed at the Wadsworth Center of the New York State Department of Health in Albany, N.Y. Both studies included individuals with a broad spectrum of HIV-1 disease. The institutional review boards at each clinical site and the New York State Department of Health approved the investigation. Each woman provided informed consent at enrollment.

To examine the effect of combination antiretroviral therapy on HIV-1 coreceptor use, women infected with CXCR4 strains were sought. After screening twenty-two women, most with advanced HIV-1 disease, fifteen participants meeting the following criteria were studied: 1) viral isolates displayed CXCR4 zidovudine monotherapy strains while untreated or taking nucleoside analogues alone; and 2) antiretroviral therapy, when initiated, was documented by the WIHS database, Wadsworth study questionnaires, and records of treating physicians.

Sample Collection Preparation, and Analysis

Once the study population was selected, blood was drawn and separated into plasma and cell components. Anastos et al. (2000) J. AIDS Hum. Retro. (in press); Fang et al. (1995). HIV-1 RNA in plasma was quantitated by using NucliSens (Organon Teknika Corp., Durham, N.C.), with a lower limit of quantitation of ~80 copies/ml. The CCR5 genotype of each patient was determined as described. Samson et al. (1996).

Derivation of Primary Viral Isolates and Biological Clones

Primary isolates of HIV-1 were obtained by co-culture with normal donor PBMCs. Fang et al. (1995). Viral isolates were titrated in PBMCs. Fang et al. (1995). Biological clones were derived from primary isolates by short-term limiting dilution cloning. Connor et al. (1997).

Patient Population and Response to Therapy

Initially, most of the fifteen women displayed high plasma HIV-1 RNA levels and CD4+ cell depletion (means of 5.22 $\log_{10}$ copies/ml and 147 cells/mm$^3$, respectively). At that time, eight women were receiving antiretroviral therapy, primarily zidovudine monotherapy. While under study, however, 12 initiated new combination regimens; 9 received HAART (Group I) and 3 received two or more nucleoside analogues (Group II). Three individuals, by contrast, did not initiate new therapy during the study (Group III) (Table 1). In Table 1, "Before therapy" refers to data obtained at the visit immediately preceding initiation of new two or three drug antiretroviral therapy in Groups I & II. For Group III, data from the first time point are shown (a). "Follow-up" refers to data obtained at the first time point following the initiation of the anti-HIV therapy listed for Groups I & II. For Group III, data from the final time point are displayed (b). Comparisons of QXR before and after initiation of new, combination antiretroviral therapy were statistically significant for Group I, HAART recipients (c), (P=0.023) and Groups I & II combined, consisting of all treated patients (P=0.003).

TABLE 1

Patient Characteristics Before and After Antiretroviral Therapy

| | Status Before Combination Therapy[a] | | | | Follow-up Status[b] | | | |
|---|---|---|---|---|---|---|---|---|
| Pt. | HIV-1 RNA, log copies per ml | CD4+ count, cells per mm3 | Anti-HIV Therapy | QXR, proportion of HIV-1 Using R5 | HIV-1 RNA, log copies per ml | CD4+ count, cells per mm3 | Anti-HIV Therapy | QXR, proportion of HIV-1 Using R5 |
| Group I: HAART Recipients | | | | | | | | |
| 1 | 5.30 | 188 | AZT | 0.36 | 5.08 | 578 | 3TC, d4T, Nel | 1.00 |
| 2 | 5.69 | 3 | None | 0.00 | 3.41 | 90 | 3TC, d4T, Nel | 1.00 |
| 3 | 5.75 | 291 | None | 0.34 | 4.54 | 370 | AZT, 3TC. Saq | 0.45 |
| 4 | 5.28 | 9 | d4T | 0.36 | 3.08 | 15 | 3TC, d4T, Rit | 0.36 |
| 5 | 6.08 | 41 | None | 0.36 | 4.96 | 11 | 3TC, d4T, Saq | 0.90 |
| 6 | 5.11 | 19 | None | 0.45 | 3.70 | 24 | 3TC, d4T, Ind | 1.00 |
| 7 | 4.94 | 42 | AZT | 0.36 | 5.61 | 10 | 3TC, d4T, Ind | 0.36 |
| 8 | 5.65 | 0 | AZT, ddI | 0.44 | 5.29 | 23 | 3TC, d4T, Ind | 1.00 |
| 9 | 5.58 | 259 | AZT | 0.90 | 4.86 | 282 | 3TC, d4T, Ind | 1.00 |
| Group II: Recipients of Combination Antiretroviral Therapy | | | | | | | | |
| 10 | 5.04 | 307 | AZT | 0.00 | 4.58 | 378 | 3TC, ddI | 1.00 |
| 11 | 5.10 | 222 | AZT, ddI | 0.00 | 4.94 | 213 | AZT, 3TC, d4T | 0.36 |
| 12 | 5.04 | 251 | None | 0.36 | 4.23 | 345 | AZT, 3TC | 1.00 |

TABLE 1-continued

Patient Characteristics Before and After Antiretroviral Therapy

| | Status Before Combination Therapy[a] | | | | Follow-up Status[b] | | | |
|---|---|---|---|---|---|---|---|---|
| Pt. | HIV-1 RNA, log copies per ml | CD4+ count, cells per mm3 | Anti-HIV Therapy | QXR, proportion of HIV-1 Using R5 | HIV-1 RNA, log copies per ml | CD4+ count, cells per mm3 | Anti-HIV Therapy | QXR, proportion of HIV-1 Using R5 |
| Group III: Recipients of No Therapy or AZT Monotherapy | | | | | | | | |
| 13 | 4.32 | 191 | None | 0.45 | 4.13 | 184 | None | 0.36 |
| 14 | 4.28 | 670 | None | 0.52 | 3.83 | 429 | None | 0.36 |
| 15 | 5.23 | 43 | AZT | 0.00 | 5.36 | NA | None | 0.00 |
| Mean Values for Treatment Groups | | | | | | | | |
| Group I | 5.49 | 94 | | 0.40 | 4.50 | 155 | | 0.74[c] |
| Group II | 5.06 | 260 | | 0.12 | 4.58 | 312 | | 0.79 |
| Group I & II, Combined | 5.38 | 136 | | 0.33 | 4.52 | 194 | | 0.75[c] |
| Group III | 4.61 | 301 | | 0.32 | 4.44 | 307 | | 0.24 |

For those initiating new therapy, HIV-1 RNA levels dropped by an average of 0.86 $\log_{10}$ copies/ml and CD4+ counts increased by an average of 58 cells/ml by the first study visit after starting the new regimens. The viral levels rebounded by 0.69 $\log_{10}$ copies/ml, however, by the end of the 28.5 month mean follow-up period for treated patients, at which time 11 of the 12 women continued to take antiretroviral therapy (6 HAART, 5 two drug regimens).

Assay for Coreceptor Use

Changes in coreceptor use of primary HIV-1 isolates and biological clones from participants in the study were followed by using a HOS-CD4+ cell system. The parental HOS-CD4+ line is a human osteogenic sarcoma cell line stably expressing high levels of CD4. HOS-CD4+ cells transfected with genes encoding either CCR5 or CXCR4 in addition to CD4 (cell lines HOS-CD4.CCR5 and HOS-CD4.CXCR4 respectively) served as indicator lines for coreceptor use. Deng et al. (1996). To determine coreceptor use, HOS-CD4.CCR5 and HOS-CD4.CXCR4 cells were seeded onto 12-well plates and, after 24 hours, inoculated with a standard quantity of titered virus; $10^2$ TCID$_{50}$ of first passage primary viral isolates or biological clones were assayed in duplicate. HIV JR-FL and LAV/HTLV-IIIB inoculated in parallel as CCR5- and CXCR4-specific positive control viruses, respectively, and uninoculated cells were used as negative controls. To eliminate any artifacts resulting from infection via low levels of endogenous coreceptor expression, parental HOS-CD4+ cells were also inoculated with duplicate primary and control isolates.

Supernatants were harvested at day 10 after infection and analyzed for HIV-1 p24 antigen using a commercially available ELISA assay (NEN Life Science Products, Boston). ELISA values were standardized so that 0 pg/ml was set at the level equal to three times the mean value of the negative controls. A culture was considered positive if the p24 antigen level was equal to or greater than 25 pg/ml. Experimental results were discarded if: 1) any parental HOS-CD4+ culture tested positive; or 2) any JR-FL or LAV/HTLV-IIIB positive control culture tested negative. If the variance in p24 antigen level between duplicate cultures was greater than 25%, the coreceptor use assay for that particular viral isolate was repeated. Results of the coreceptor use assay were then categorized in a semiquantitative manner according to p24 antigen level as follows: negative (p24<25 pg/ml), +/−(25-50 pg/ml), 1+(50-250 pg/ml), 2+(250-500 pg/ml), and 3+($\geq$500 pg/ml).

Phenotypic Characterization

The presence of syncytium-inducing (SI) variants of HIV-1 in patient primary viral isolates was determined by infection of MT-2 cell cultures as previously described. Koot et al. (1993). A pooled stock of HIV LAV/HTLVIII was used as a positive control.

Example 2

Antiretroviral Therapy Preferentially Suppresses CXCR4 Strains

Fourteen women initially displayed viral populations composed of both CCR5 and CXCR4 viruses (FIG. 1) and one displayed virus that exclusively used CXCR4. CXCR4 viruses persisted at subsequent time points in patients who did not initiate new combination therapy, a finding exemplified in FIG. 1 by Patient 13, who remained untreated throughout the study, and Patients 1, 2, and 8, whose virus was sampled on multiple occasions before new therapy commenced. Viruses using CXCR4 appeared to be preferentially suppressed, however, when new regimens were initiated. Not only were CXCR4 strains eliminated by the first time point after starting new therapy in half of the treated women (FIG. 1, Patients 1, 2, 6, 8, and 10), but the proportion of these viruses seemed to be diminished in most of the others. In addition, patients who experienced a rebound in HIV-1 RNA levels and CXCR4 strains while on therapy often achieved suppression of CXCR4 strains a second time when the antiretroviral regimen was changed (FIG. 1, Patients 2 and 8).

Coreceptor Use by Biologically Cloned Viruses

Delineation of the proportion of individual viruses using each coreceptor was prompted by two aspects of the pattern of HIV-1 coreceptor use in these individuals. First, analyses of primary viral isolates by the HOS-CD4+ system indicated coreceptor use by both CCR5 and CXCR4 viruses at many time points (FIG. 1). Because primary isolates comprise a molecular mixture of viral quasispecies, we wished to determine whether use of both coreceptors was due to dual tropic viruses or a mixture of individual viruses with CCR5 and CXCR4 tropisms. In addition, to compare coreceptor use rigorously over time, it is desirable to quantitate the proportion of virus using each coreceptor. For these reasons, biologic clones, which were derived from the patients' primary isolates by performing limiting dilution cultures were isolated. Coreceptor use was then determined for 25 clones from each isolate by employing the HOS-CD4+ cell system. Biologic clones from these patients used either CCR5 or CXCR4; no dual tropic viruses were detected among the 525 clones by using our assay system. In addition, the distribution of coreceptor use by the clones generally confirmed the semiquantitative results obtained for primary isolates; proportions of HIV-1 using each coreceptor appeared roughly similar whether the cloned virus or primary isolates were examined (Table 2A, HIV-1 coreceptor use in primary viral isolates and biologic clones).

TABLE 2A

| Pt | Months After Baseline | Treatment | Co-Receptor Use of Primary Viral Isolates | | Distribution of Co-Receptor Use by Biologic Clones | |
|---|---|---|---|---|---|---|
| | | | CCR5 | CXCR4 | CCR5 | CXCR4 |
| 2 | 16 | AZT, 3TC | +++ | +++ | 8 | 17 |
| | 18 | HAART | + | − | 25 | 0 |
| | 26 | HAART | + | +++ | 4 | 21 |
| 5 | 0 | None | ++ | +++ | 11 | 14 |
| | 6 | HAART | +++ | + | 21 | 4 |
| | 9 | d4T, Ind | +++ | +++ | 10 | 15 |
| | 16 | HAART | +++ | − | 25 | 0 |
| 14 | 0 | None | +++ | ++ | 13 | 12 |
| | 7 | None | +++ | +++ | 9 | 16 |

In Table 2A coreceptor use was determined for the primary viral isolate obtained at each time point and for 25 biologic clones derived from each isolate.

Studies of biologic clones obtained at serial time points also confirmed that the predominant viral population shifted from CXCR4 to the less pathogenic CCR5 after initiation of new combination antiretroviral therapy (Table 2A). For example, analyses of virus obtained from Patient 2 sixteen months after baseline and eight months after initiation of double therapy showed only eight clones that used CCR5 as compared to seventeen that used CXCR4. After a switch to a HAART regime that included two new drugs, however, the viral population in this patient shifted and all 25 biologic clones used CCR5. A similar pattern was exhibited by biologic clones from Patient 5, whose virus shifted dramatically to CCR5 on the two occasions that HAART was initiated. Patient 14, by contrast, remained untreated and her viral population evolved to comprise a larger proportion of clones using CXCR4 over time.

The MT2 assay to detect SI viruses in culture was also performed on primary isolates derived at each time point. These results confirmed the pattern of HIV-1 coreceptor use described here. Thirteen of the fifteen patients were infected initially with SI virus. In all eleven of those who displayed SI virus and received new combination therapy, the phenotype changed at least transiently to non-syncytia inducing (NSI) after treatment (data not shown).

Sequence Analyses of the HIV-1 V3 Loop

HIV-1 virions were isolated from plasma samples as described. (Fang et al. (1996) J. AIDS Hum. Retro. 12:352-7). Reverse transcriptase polymerase chain reaction amplification produced a 920-bp amplicon spanning the V3 region of the env gene. Reaction conditions were controlled rigorously to minimize recombination and other artifacts. Fang et al. (1996). Amplified products were cloned into a TOPO™ TA vector (Invitrogen, Carlsbad, Calif.), verified by restriction digestion, and sequenced. Alignment of the sequences was initially done using the PILEUP program in the GCG Suite (Genetics Computer Group, Madison, Wis.), then checked manually. Envelope sequences were used to predict coreceptor use on the basis of the overall charge of the V3 loop and the presence of basic or acidic residues at positions 275 and 287 of the env gene. Bhattacharyya et al. (1996); and Hung et al. (1999).

Coreceptor Use Determined by Sequence Analysis of HIV-1 RNA Molecular Clones

These sequences predicted a pattern of coreceptor use that essentially paralleled the one obtained by using viral culture (Table 2B, Coreceptor use determined by cocultivation of PBMCs vs. sequence analysis of plasma HIV-1 RNA). Table 2B shows a comparison of coreceptor use over time determined by two methods in representative study patients. At each time point, coreceptor use was assayed by co-cultivating PBMCs and determining the V3 loop sequence of virion-derived HIV-1 RNA.

The sequence data underscored the change in coreceptor use seen after initiation of treatment. These experiments suggest that study of cultivated virus reflects the coreceptor use of currently replicating virus and is likely to reveal the shifts in viral populations that occur as a result of recent antiretroviral therapy.

TABLE 2B

| Pt | Months After Baseline | Treatment | Co-Receptor Use by Cocultivated Virus | | Distribution of Co-Receptor Use Predicted by V3 Loop Sequences | | Total # of Clones |
|---|---|---|---|---|---|---|---|
| | | | CCR5 | CXCR4 | CCR5 | CXCR4 | |
| 1 | 6 | AZT | +++ | +++ | 9 | 4 | 13 |
| | 33 | HAART | +++ | − | 13 | 0 | 13 |
| | 36 | HAART | +++ | + | 8 | 2 | 10 |
| 2 | 16 | AZT, 3TC | +++ | +++ | 1 | 13 | 14 |
| | 22 | HAART | + | ++ | 0 | 13 | 13 |
| | 26 | HAART | + | +++ | 3 | 8 | 11 |
| 5 | 0 | None | ++ | +++ | 2 | 10 | 12 |

TABLE 2B-continued

| | Months After Baseline | | Co-Receptor Use by Cocultivated Virus | | Distribution of Co-Receptor Use Predicted by V3 Loop Sequences | | Total # of Clones |
|---|---|---|---|---|---|---|---|
| Pt | | Treatment | CCR5 | CXCR4 | CCR5 | CXCR4 | |
| | 6 | HAART | +++ | + | 8 | 3 | 11 |
| | 9 | d4T, Ind | +++ | +++ | 2 | 10 | 12 |
| | 16 | HAART | +++ | − | 12 | 0 | 12 |
| 14 | 0 | None | +++ | ++ | 5 | 6 | 11 |

Statistical Methods

The Wilcoxon Rank Sum Test was used to make comparisons between the magnitude of log viral level, CD4+ counts, and QXR values. Data for factors relating to changes in QXR values were analyzed by multivariate Poisson regression. Variables included log HIV-1 RNA levels, changes in viral levels, CD4+ cell counts, changes in CD4+ cell counts, and indicator variables for levels of antiretroviral therapy.

To quantitate HIV-1 coreceptor use, we constructed a variable, λ, as the proportion of strains using CCR5. This variable has since been renamed QXR. QXR=1 represents an isolate in which all strains prefer the CCR5 coreceptor but QXR=0 indicates that all prefer CXCR4. QXR values were assessed by utilizing qualitative assay data derived from primary isolates, biologic clones, and sequences of the V3 portion of the env gene. In determination of the coreceptor use of 525 biologic clones, none was dual tropic, suggesting that true dual tropic viruses are rare when using our assay method. It was therefore assumed for this calculation that the probability of a single virion possessing the phenotypic attributes of both coreceptors is small. Thus, for the vast majority of virions, each virion uses either CCR5 or CXCR4. This relationship can be stated as a mixture $$D = QXR(CCR5) + (1-QXR)(CXCR4); 0 \leq QXR \leq 1,$$

where D is the distribution of viral phenotypes. By design, it is a binomial population.

QXR values were constructed by relating data derived from the same patient sample by using three different analyses: biologic cloning, V3 sequencing of patient-derived molecular clones, and qualitative assays of primary isolates. To construct QXR values, we first calculated the proportion of biologic and, if available, molecular clones using CCR5 at each time point, then linked the proportion to the qualitative coreceptor use score (− to 3+) of primary isolates obtained simultaneously. Data that were not available were interpolated. The data were transformed to approximate a Poisson distribution. Poisson regression analysis was then performed to determine the factors associated with changes in QXR values.

Quantitation of Coreceptor Use by CCR5 and CXCR4

The large number of biologic and molecular clones permitted derivation of a system to quantitate the proportion of virus in a clinical specimen that uses each coreceptor. In this system, QXR is a continuous, nonlinear variable between one and zero derived from the results presented here showing coreceptor use by biologically and molecularly cloned virus; it describes the mixed proportion of viruses using CCR5 and CXCR4. A QXR value near one describes a population of viruses that almost all use CCR5; a value near zero describes a population that almost all use CXCR4. By applying this method, it was determined that the proportion of virus using each coreceptor for each patient over time.

To quantitate the effect of combination therapy on HIV-1 coreceptor use, we compared the QXR values of virus obtained at the visits before and immediately after initiating new combination therapy. This comparison demonstrated a clear, statistically significant shift of the predominant viral population from CXCR4 to CCR5 (Table 1). The mean QXR values for virus from all twelve patients starting combination therapy (Groups I & II) changed from 0.33 to 0.75 (P=0.003 by using the binomial proportion comparison test). For the subset of nine who initiated HAART (Group I), the shift in QXR extended from 0.40 to 0.74 (P=0.023). In addition, we assessed separately the effect of initiating treatment with two or more nucleoside analogues and no protease inhibitor on coreceptor use. Five of the patients who ultimately received HAART had received regimens consisting of two nucleoside analogues previously. The QXR values of virus obtained before or after initiation of two or more nucleoside analogues in a group of eight patients (Group II and Patients 1, 2, 6, 7, and 9) were compared; in this group the QXR values changed from 0.30 to 0.84 (P=0.008). By contrast, in the Group III patients, who did not initiate combination therapy, the mean QXR value decreased from 0.32 to 0.24 during the course of this study. These numerical comparisons of coreceptor use demonstrated a shift in the predominant viral population from CXCR4 to CCR5 following initiation of a variety of combination antiretroviral regimens.

Long-Term Analysis of Antiretroviral Therapy, Viral Level, and CD4+ Cell Count Effects on Coreceptor Use The period of follow-up for treated women in this study averaged 28.5 months, during which their coreceptor use, plasma HIV-1 RNA levels, and CD4+ cell count varied, sometimes in concert (FIG. 1). The mulitvariate regression indicated that antiretroviral therapy with two or more drugs was by far the most significant factor in determining QXR, the numerical expression of the proportion of viruses using CCR5 (P=0.01). Although changes in viral level and CD4+ cell count had a significant effect on QXR in univariate analysis, they lost all significance when considered in a multivariate regression analysis with antiretroviral therapy. The strength of the relationship between initiation of therapy and shift in HIV-1 coreceptor use is reflected in the course of treated individuals like Patient 8, who maintained high plasma HIV-1 RNA levels during treatment but demonstrated a substantial, long-term shift in viral population toward CCR5 (FIG. 1).

Example 3

Dynamics of HIV-1 Coreceptor Utilization Switch

Figure 2:
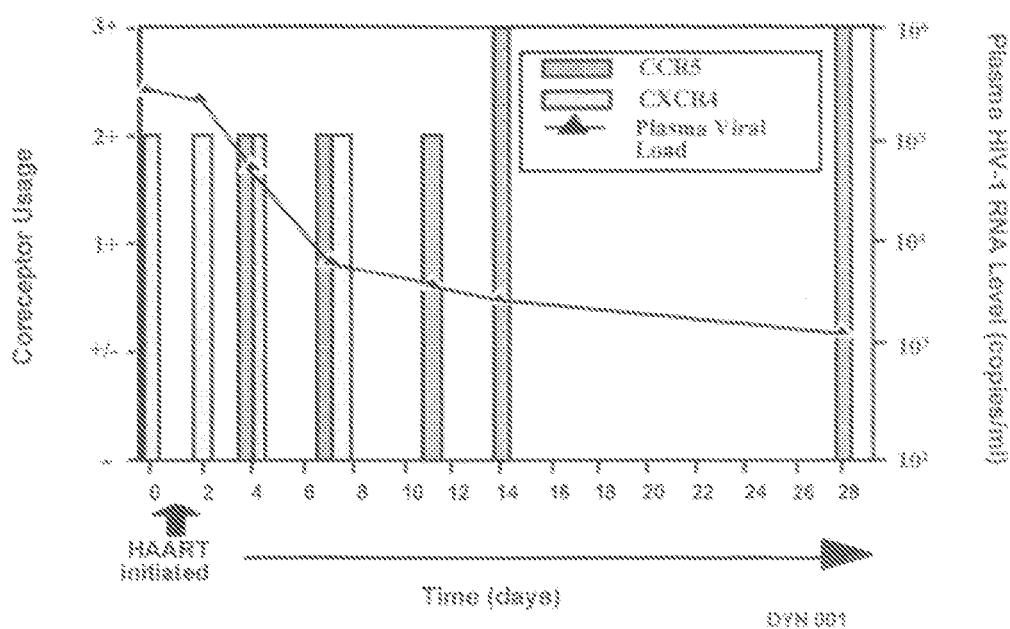
FIG. 2 depicts the dynamics of the shift in coreceptor utilization immediately following initiation of HAART.

The dynamics of the shift in coreceptor utilization immediately following initiation of HAART have been characterized. Coreceptor utilization immediately following the initiation of HAART was determined by studying virus derived from the patient's PBMC's. Results show the following: 1) this patient was unusual in that her initial viral population was composed of X4 viruses only, 2) by the third day after the initiation of HAART, the viral population had switched to equal proportions of X4 and R5 using strains, and 3) by day 11, the population had entirely switched to R5 using virus (FIG. 2).

Comparison of coreceptor usage in this patient was also performed using a recombinant assay that does not require culturable primary isolates. The results of the recombinant assay were identical to the results obtained using virus derived from the patient's PBMC's. These data document a rapid, complete switch in coreceptor utilization by virus in peripheral blood that occurred less than two weeks after initiating HAART. To understand the complexities of HIV-1 pathogenesis, it is necessary to consider the heterogeneity of viral populations and viral reservoirs. This approach will provide insight into the dynamics of suppressing different populations of virus.

Example 4

Rapid Cell Fusion Assay for Coreceptor Utilization

Viral coreceptor usage was separately evaluated through the use of a Rapid Cell Fusion Assay. This assay enables determination of coreceptor usage from cloned HIV env gene sequences obtained directly from patient samples (e.g. blood, mucosal tissue). This method allows for greater efficiency in determination of viral coreceptor usage, by circumventing the need for cultivation of primary isolates. The Rapid Cell Fusion Assay can advantageously produce a result within one week after obtaining a patient sample. In addition, the Rapid Cell Fusion Assay allows study of patient-derived virus obtained from sites other than the peripheral blood, particularly those sites from which cultured virus cannot be obtained. For example, while circulating macrophages and $CD4^+$ T cells are the dominant reservoir of HIV-1, viral populations distinct from those in the peripheral blood exist in many tissue reservoirs, including the genital mucosa. It is important to study these different reservoirs as HIV-1 viral populations in infected individuals demonstrate marked heterogeneity, with virus varying in the same compartment over time and in different compartments contemporaneously. Myers et al. (1995); Meyerhans et al. (1989); Vernazza et al. (1994); Cheng-Mayer et al. (1989); Koyanagi et al. (1987). Even in patients receiving combination anti-HIV-1 therapy, studies of lymphoid tissue reservoirs showed persistent viral replication in lymph nodes, with viral load in tissue exceeding that in plasma by orders of magnitude in most cases. Wong et al. (1997); Cavert et al. (1997); Haase et al. (1996).

Steps of the Rapid Cell Fusion Assay

The HL3T1 cell line was derived by stable transfection of parental HeLa cells with a chloramphenicol acetyltransferse (CAT) reporter construct containing a CAT gene is linked to an HIV-1 LTR promoter. The HL3T1 cells produce CAT protein only upon introduction of an active HIV-1 Tat protein. HL3T1 cells were transfected with a cloned env gene derived from a patient of interest. The cloned env gene product is expressed on the surface of the HL3T1 cells.

Indicator cell lines GHOST.CCR5 and GHOST.CXCR4 (respectively hereinafter "R5-tat" and "X4-tat") cells were transfected with pSV2tat72, a construct expressing high levels of HIV-1 Tat under the control of the SV40 early promoter.

HL3T1 cells containing a cloned patient env gene were fused to R5-tat and X4-tat cells. Cell surface envelope protein variants will selectively interact with either CCR5 or CXCR4. Fusion only occurs when an HL3T1 envelope protein interacts with an indicator cell expressing a compatible coreceptor. Therefore, HL3T1 cells will fuse with either R5-tat and X4-tat, depending on the patient's env gene specificity. To initiate fusion, transfected HL3T1 and R5-tat or X4-tat cells were mixed in 6-well plates at 37° C. and allowed to fuse for 48 hours. To quantitate fusion, the cells were lysed with 0.5% NP-40. Fusion of HL3T1 cells to R5-tat or X4-tat activated CAT gene expression. Aliquots of the cell lysates were monitored for CAT production using a commercially available kit (CAT-ELISA, Boehringer Mannheim).

Twenty-five clones from each sample were analyzed to ensure that the fusion assay reflected the heterogeneous nature of HIV-1 populations. Sample results of the Rapid Cell Fusion Assay for Coreceptor Utilization are presented below. For all env clones assayed in this manner, sequence analysis has revealed a 97% correlation between coreceptor usage and predicted env genotype.

| CLONE | V3 LOOP SEQUENCE | CORECEPTOR | |
|---|---|---|---|
| AF2P12-1 | CIRPNNNTRTSIRIGPGQAFYATGNIIGDIRQAYC | CCR5 | (SEQ ID NO.1) |
| AF2P12-2 | CIRPNNNTRTSIRIGPGQAFYATGNIIGGIRQAYC | CCR5 | (SEQ ID NO.35) |
| AF2P12-3 | CIRPNNNTRTSIRIGPGQAFYATGNIIGDIRQAYC | CCR5 | (SEQ ID NO.1) |
| AF2P12-4 | CIRPNNNTRTSIRIGPGQAFYATGNIIGDIRQAYC | CCR5 | (SEQ ID NO.1) |
| AF2P12-6 | CIRPNNNTRTSIRIGPGQAFYATGNIIGDIRQAYC | CCR5 | (SEQ ID NO.1) |
| AF2P12-8 | CIRPNNNTRTSIRIGPGQAFYATGNIIGDIRQAYC | CCR5 | (SEQ ID NO.1) |
| AF2P12-9 | CIRPNNNTRTSIRIGPGQAFYATGNIIGDIRQAYC | CCR5 | (SEQ ID NO.1) |
| AF2P12-10 | CIRPNNNTRTSIRIGPRQAFYATGNIIGDIRQAYC | CXCR4 | (SEQ ID NO.2) |
| AF2P12-11 | CIRPNNNTRTSIRIGPGQAFYATGNIVGDIRQAYC | CCR5 | (SEQ ID NO.3) |
| AF2P12-12 | CIRPNNNTRTSIRIGPGQAFYATGNIIGDIRQAYC | CCR5 | (SEQ ID NO.1) |
| AF3P-2 | ........RKSVHIGPGQAFYATGDIIGNIRKAHC | negative | (SEQ ID NO.4) |
| AF3P-4 | CTRPNNNTRKSVHIGPGQAFYATGDIIGNIRKAHC | CCR5 | (SEQ ID NO.5) |
| AF3P-5 | CTRPNNNTRKSVHIGPGQAFYATGDIIGNIRKAHC | CCR5 | (SEQ ID NO.5) |
| AF3P-6 | CTRPNNNTRKSVHIGPGQAFYATGDIIGNIRQAHC | CCR5 | (SEQ ID NO.6) |

-continued

```
AF3P-7      CTRPNNNTRKSVHIGPGQAFYATGDIIGNIRKAHC    CCR5      (SEQ ID NO.5)
AF3P-8      CTRPNNNTRKSVHIGPGQAFYATGDIIGNIRKAHC    CCR5      (SEQ ID NO.5)
AF3P-9      CTRPNNNTRKSVHIGLGQAFYATGDIIGNIRKAHC    CCR5      (SEQ ID NO.36)
AF3P-10     CTRPNNNTRKSVHIGPGQAFYATGDIIGNIRKAHC    CCR5      (SEQ ID NO.5)
AF3P-11     CTRPNNNTRKSVHIGPGQAFYATGDILGNIRQAHC    CCR5      (SEQ ID NO.37)
AF3P-12     CTRPNNNTRKSVHIGPGQAFYATGDIIGNMRKAHC    CCR5      (SEQ ID NO.7)

AF5P-5      CTRPNNNTRKSVHIGPGQAFYATGDIIGDIRQAYC    CCR5      (SEQ ID NO.38)
AF5P-6      CTRPNNNTKKSVHIGPGQAFYATGDIIGDIRQAYC    CCR5      (SEQ ID NO.39)
AF5P-8      CTRPNNNTRKSVHIGPGQAFYATGDIIGDIRQAYC    CCR5      (SEQ ID NO.38)

AF6P-1      CTRPINNRRKSIHMGPGQAFYGT.DDIIGDIRKARC   CCR5      (SEQ ID NO.8)
AF6P-3      CTRPINNRRKSIHMGPGQAFYGT.DDIIGDIRKARC   CCR5      (SEQ ID NO.8)
AF6P-7      CTRPSNNRRKSIHKGDQDKHSMEHDDVIGDIRKARC   negative  (SEQ ID NO.9)
AF6P-9      CTRPINNRRKSIHMGPGQAFYGT.DDIIGDIRKARC   CCR5      (SEQ ID NO.8)
AF6P-10     CTRPINNRRKSIHIGPGQAFYGT.DDIIGDIRQAHC   CCR5      (SEQ ID NO.32)
AF6P-11     CTRPSNNRRKSIHMGPGQAFYGT.DDIIGGIRKARC   CCR5      (SEQ ID NO.33)
AF6P-12     CTRPSNNRRKSIHMGPGQAFYGT.DDIIGDIRKARC   CCR5      (SEQ ID NO.34)

AF7P-9      CIRPNNNTRQSVHIGPGQALYTTEIIGDIRKAHC     CCR5      (SEQ ID NO.11)
AF7P-12     CIRPNNNTRQSVHIGPGQALYTTEIIGDIRKAHC     CCR5      (SEQ ID NO.11)

AF9P2-3     CTRPNNNTITSIRIGPGQAFYATGSIIGNIRQAHC    CCR5      (SEQ ID NO.12)
AF9P2-4     CTRPNNNTITSIRIGPGQAFYATGSIIGNTRQAHC    CCR5      (SEQ ID NO.13)
AF9P2-7     CTRPNNNTITSIRIGPGQAFYATGSIIGNIRQAHC    CCR5      (SEQ ID NO.12)
AF9P2-9     CTRPNNNTITSIRIGPGQAFYATGSIIGNIRQAHC    CCR5      (SEQ ID NO.12)
AF9P2-10    CTRPNNNTITSIRIGPGQAFYATGSIIGNIRQAHC    CCR5      (SEQ ID NO.12)
AF9P2-11    CTRPNNNTITSIRIGPGQAFYATGSIIGNIRQAHC    CCR5      (SEQ ID NO.12)
AF9P2-12    CTRPNNNTITSIRIGPGQAFYATGSIIGNIRQAHC    CCR5      (SEQ ID NO.12)

AF10P97-2   CTRPNDNIRKSVHIGPGQAFYATGDIIGDIRRAHC    CCR5      (SEQ ID NO.14)
AF10P97-4   CTRPNDNIRKRVHIGPGQAFYATGDVIGDIRRAHC    CXCR4     (SEQ ID NO.40)
AF10P97-6   CTRPNDNIRKSVHIGPGQAFYATGDIIGDIRRAHC    CCR5      (SEQ ID NO.14)
AF10P97-11  CTRPNDNIRKSVHIGPGQAFYATGDIIGDIRRAHC    CCR5      (SEQ ID NO.14)

Sequence Identifiers (SEQ ID NO: 1)     CIRPNNNTRTSIRIGPGQAFYATGNIIGDIRQAYC
(SEQ ID NO: 2)     CIRPNNNTRTSIRIGPRQAFYATGNIIGDIRQAYC
(SEQ ID NO: 3)     CIRPNNNTRTSIRIGPGQAFYATGNIVGDIRQAYC
(SEQ ID NO: 4)     RKSVHIGPGQAFYATGDIIGNIRKAHC
(SEQ ID NO: 5)     CTRPNNNTRKSVHIGPGQAFYATGDIIGNIRKAHC
(SEQ ID NO: 6)     CTRPNNNTRKSVHIGPGQAFYATGDIIGNIRQAHC
(SEQ ID NO: 7)     CTRPNNNTRKSVHIGPGQAFYATGDIIGNIRKAHC
(SEQ ID NO: 8)     CTRPINNRRKSIHMGPGQAFYGT.DDIIGDIRKARC
(SEQ ID NO: 9)     CTRPSNNRRKSIHKGDQDKHSMEHDDVIGDIRKARC
(SEQ ID NO: 10)    CTRPINNRRKSIHIGPGQAFYGT.DDIIGDIRQAHC
(SEQ ID NO: 11)    CIRPNNNTRQSVHIGPGQALYTTEIIGDIRKAHC
(SEQ ID NO: 12)    CTRPNNNTITSIRIGPGQAFYATGSIIGNIRQAHC
(SEQ ID NO: 13)    CTRPNNNTITSIRIGPGQAFYATGSIIGNTRQAHC
(SEQ ID NO: 14)    CTRPNDNIRKSVHIGPGQAFYATGDIIGDIRRAHC
```

Methods of env Gene Cloning

Figure 3:
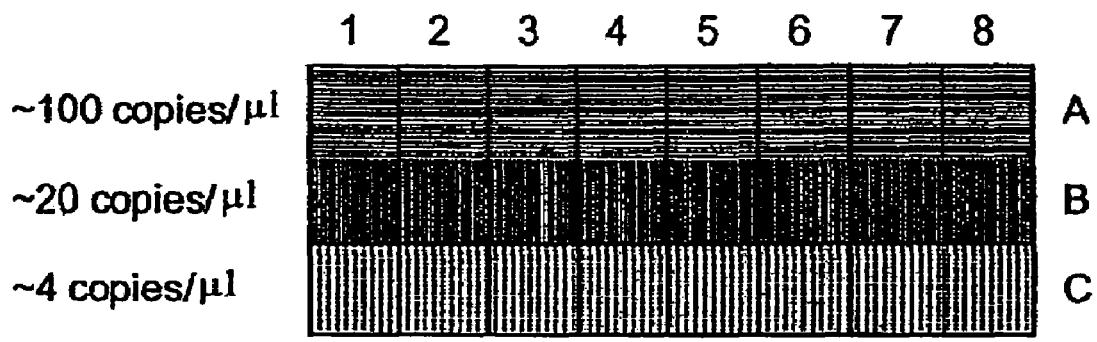
FIG. 3 depicts an example of a template set-up for a PE2400 PCR tray-retainer.

In cloning the env gene from patients by the use of long RT-PCR, two potential problems may result: 1) recombination between molecules; and 2) underestimates of sequence diversity. High fidelity cloning of the samples above was achieved by routine performance of multiple RT reactions on limiting dilutions of RNA, followed by multiple PCR's on cDNAs obtained from each RT reaction. Performance of multiple PCR's on each cDNA preparation increased the likelihood of amplifying a different HIV-1 RNA species. These measures also decrease the chance of recombination. Accordingly, the following protocol was developed:

1. Peripheral blood was collected and separate into plasma and cell components. Other fluids and tissues derived from an HIV-infected individual can also be used, with minor modifications to the RNA extraction protocol outlined below.
2. HIV-1 RNA was quantitated in plasma by using NucliSens (Organon Teknika Corp., Durham, N.C.), with a lower limit of quantitation set at approximately 80 copies/ml.
3. RNA extraction:
    a) HIV-1 RNA was extracted from plasma using Qiagen's Viral RNA Kit and following the manufacturer's standard protocol.
    b) Samples were standardized by extracting a volume of plasma equal to 10000 copies of HIV-1 RNA. For example, if the patient's plasma viral load is 25000 copies/ml, 0.4 ml of plasma in the extraction should be used.
    c) Following extraction, the virus was resuspended in 100 ul of Rnase-free water (to give a final concentration of ≦100 copies of HIV-1 RNA per ul) and optionally treated with Rnase-free Dnase to remove any contaminating DNA.
4. RT-PCR using limiting dilution to ensure minority species amplification:
    a) Samples of serially diluted RNA template were generated in a series of 1:5 dilutions using the following template concentrations:
    ~100 copies/µl
    ~20 copies/µl
    ~4 copies/µl This dilution series is sufficient to ensure minority species amplification. Conditions are adaptable to achieve limiting dilutions.

b) 1 ul aliquots of RNA template were distributed into the wells of a PE2400 or PE9700 PCR tray-retainer and 8-24 tubes containing of each RNA dilution were prepared. An example of the template set-up for a PE2400 is shown in FIG. 3.

c) An RT reaction mix was prepared:

| reagent | per reaction |
|---|---|
| Rnase-free H$_2$O | 2 ul |
| 10x PCRII buffer | 2 ul |
| 25 mM MgCl$_2$ | 4 ul |
| 10 mM dATP | 2 ul |
| 10 mM dCTP | 2 ul |
| 10 mM dGTP | 2 ul |
| 10 mM dTTP | 2 ul |
| Rnase Inhibitor | 1 ul |
| 50 mM Random Hexamers | 1 ul |
| MMLV RT (50 U/ul) | 1 ul |

All reagents are commercially available from Perkin Elmer. Each well received a 19 ul aliquot. Samples were incubated for 60 minutes at 37° C., followed by heat inactivation for 5 minutes at 95° C. Samples were stored at 4° C.

d) The Primary PCR reaction mix was prepared:

| reagent | per reaction |
|---|---|
| sterile H$_2$O | 67.5 ul |
| 10x PCRII buffer | 8 ul |
| 25 mM MgCl$_2$ | 2 ul |
| primer HIVGao1F (20 uM) | 1 ul |
| primer HIVGao1R (20 uM) | 1 ul |
| Taq polymerase (50 U/ul) | 0.5 ul |

Primer sequences for HIVGao1F and HIVGao1R were:

```
(SEQ ID NO: 15)
HIVGao1F: 5'-GGCTTAGGCATCTCCTATGGCAGGAAGAA-3'

(SEQ ID NO: 16)
HIVGao1R: 5'-GGCTTAGGCATCTCCTATGGCAGGAAGAA-3'
```

80 ul aliquots were transferred into each well containing the RT mix. The cycle parameters were:

| Cycle file | Temp. | Time |
|---|---|---|
| 1 hold: | 94° C. | 5 minutes |
| 5 cycles: | 94° C. | 1 minute |
| | 50° C. | 1 minute |
| | 72° C. | 3.5 minute |
| 30 cycles: | 94° C. | 1 minute |
| | 55° C. | 1 minute |
| | 72° C. | 3.5 minute |
| 1 hold: | 72° C. | 10 minutes |
| 1 hold: | 4° C. | until ready for nested reaction | e) A nested PCR reaction mix was prepared:

| reagent | per reaction |
|---|---|
| sterile H$_2$O | 75.5 ul |
| 10x PCRII buffer | 10 ul |
| 25 mM MgCl$_2$ | 6 ul |
| 10 mM dNTP blend | 4 ul |
| primer HIVGao2F (20 uM) | 1 ul |
| primer HIVGao2R (20 uM) | 1 ul |
| Taq polymerase (50 U/ul) | 0.5 ul |

Primer sequences for HIVGao2F and HIVGao2R are:

```
(SEQ ID NO: 17)
HIVGao2F: 5'-AGAAAGAGCAGAAGACAGTGGCAATGA-3'

(SEQ ID NO: 18)
HIVGao2R: 5'-AGCCCTTCCAGTCCCCCCTTTTCTTTTA-3'
```

Each well of a new PE2400 base received a 98 ul aliquot, followed by 2 ul of each primary PCR reaction serving as a as template for the nested PCR reaction. The same cycle parameters as indicated for the primary PCR were applied.

Figure 4:
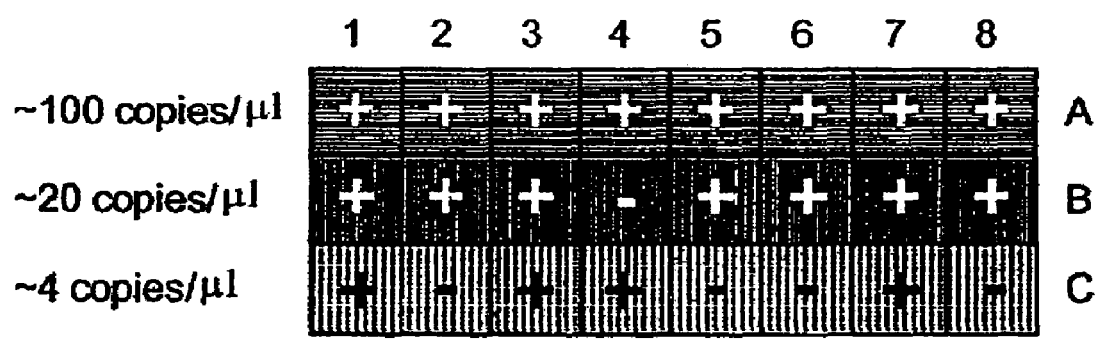
FIG. 4 depicts an example of a pattern produced by gel analysis based on an original RT layout, for use in selecting samples to be cloned/sequenced.

5. Gel analysis of RT-PCR products:

a) 10 ul of each nested PCR product was run on a 1.5% agarose gel.

b) Only the wells of the original RNA template dilution that produced approximately 50% positive wells were cloned/sequenced to ensure cloning/sequencing of an amplicion derived from a single RNA template molecule. For example, if gel analysis produced the following pattern based on the original RT layout, only the 4 positive wells of the last row (the 1:25 or ~4 copies/ul row) would be cloned/sequenced (FIG. 4.). All other positives were discarded.

c) The chosen positives were either cloned or sent directly for sequencing.

6. Cloning of RT-PCR products:

a) PCR reaction products were purified using Qiagen's Gel Extraction Kit according to the manufacturer's standard protocol.

b) Amplicons were cloned into Promega's pTarget Mammalian Expression vector following a standard protocol, such as that which is included with the pTarget Kit. Each selected positive reaction was cloned once. In addition, only one clone from each plate was picked/analyzed to ensure that the minority species were fully represented c) Plasmid DNA was prepared according to standard procedures for ABI sequencing.

7. ABI sequencing of RT-PCR products or clones:

a) Standard automated sequencing on an ABI 370 series sequencing machine was carried out. The following three primers were used to ensure complete redundant sequencing of the V3 loop of the envelope gene:

```
(SEQ ID NO: 19)
NL6942F: 5'-GCACAGTACAATGTACACATG-3'

(SEQ ID NO: 20)
NL7103F: 5'-ACAAGACCCAACAACAATACA-3'

(SEQ ID NO: 21)
NL7356R: 5'-TGTATTGTTGTTGGGTCTTGT-3'
```

8. Sequence analysis:
   a) The DNA sequence of the env V3 loop was determined.
   b) Protein translation of the V3 loop was determined.
   c) CCR5 or CXCR4 predictions were based on the scheme outlined below:

```
              268                              290
Clade B        |                                |
consensus:  N N T R K - I - G P G - A - - - T G - I I  G  (SEQ ID NOS: 22-25)
```

R5 strain if:
1. G/S at residue 273 and D/E at residue 287
2. K, H, R at residue 275 and D/E at residue 287
3. Not K, H, R at residue 275 but D/E/K/H/R at residue 287×

X4 strain if:
1. K, H, R at residue 275 and K/H/R at residue 287 d) The QXR value for the patient was calculated as:

$$QXR = (\# \text{ of } R5 \text{ clones})/(\text{total \# of clones})$$

Example 5

Qualitative HIV-1 Coreceptor Utilization Analysis Using a Heteroduplex Tracking Assay (HTA)

Specimen Accession and Plasma Preparation

The purpose of this procedure is to describe the actions followed when receiving and preparing plasma specimens for HIV-1 coreceptor utilization analysis (QXR). Samples were removed from tubes in a sterile decontaminated hood. If lavender-top tubes of whole blood were sent, it was centrifuged at room temperature for 10 minutes at 1,100×g (2300 rpm). Tubes were removed from the centrifuge and checked for complete separation. The plasma layer was transferred to freezer vials.

If, instead, frozen plasma had been shipped, it was either transferred directly to −80° C. freezer to be aliquoted and/or extracted at a later time, or the plasma was thawed and transferred to appropriately labeled cryogenic tubes in 200 µl aliquots, stored at −80° C. in RNA box, and entered into Sample Storage Log. If RNA was to be isolated on the same day, 140 µl of plasma was transferred into a 1.5 ml screw-top conical base tube labeled with sample ID# and date. After the plasma had been removed, then the blood-draw tubes were discarded in appropriate waste containers for autoclaving.

Extraction of Viral RNA

The purpose of this procedure is to extract HIV-1 viral RNA from plasma. The extracted RNA is subsequently used for analysis of HIV-1 coreceptor utilization.

Plasma samples were thawed and equilibrated to room temperature. HIV-1 RNA was extracted from plasma using Qiagen's Viral RNA Kit and following the manufacturer's standard protocol. All buffers including Lysis Buffer (AVL), Wash Buffer 1 (AW1), and Wash Buffer 2 (AW2) were prepared according to manufacturer's instructions. Any precipitate in buffers was re-dissolved by heat incubation at 80° C. if necessary, but buffer was allowed to re-equilibrate to room temperature before proceeding. To avoid co-purification of cellular DNA, only cell-free body fluids should be used for preparation of viral RNA. Samples that may contain cells (e.g., cerebrospinal fluid, urine, or swabs) should first be centrifuged for 10 minutes at 2,000 rpm, and only the clarified supernatant used.

For patients samples with HIV-1 RNA loads <$1.0 \times 10^5$ copies/ml, the plasma virions were pelleted by centrifuging the tubes for 90 minutes at 10,000×g at 4° C. All tubes to be used were labeled with the correct patient identifiers. 560 µl of Lysis Buffer (AVL) was pipetted into an appropriately labeled 1.5-ml screw-cap tube, then 140 µl plasma was added and mixed by pulse-vortexing for 15 seconds. Samples were lysed for at least 10 minutes at room temperature (although samples may be lysed for up to 24 hours at RT or 7 days at 4° C. without significant effect on the yield or quality of the purified RNA). The 1.5-ml screw-cap tubes were briefly centrifuged (2-3 seconds at 8,000 rpm) to remove drops from the inside of the lid. 560 µl of absolute ethanol was added and mixed by pulse-vortexing for 15 seconds. The 1.5-ml screw-cap tubes were briefly centrifuged (2-3 seconds at 8,000 rpm) to remove drops from the inside of the lid. 630 µl of the solution from step 2.7 was carefully applied to an appropriately labeled QIAamp™ spin column. The sample or solution from the lysis tube was then carefully applied to the column or tube by pipetting the sample into the tube without wetting the rim or outside of the column. Tubes were centrifuged for 60 seconds at 6,000×g. The QIAamp™ spin columns were transferred into clean 2-ml collection tubes. The supernatant-containing collection tubes were discarded into a waste bucket. The remaining 630 µl of the solution from step 2.7 was carefully applied, without wetting the rim or outside of the column, to an appropriately labeled QIAamp™ spin column. The tubes were centrifuged for 60 seconds at 6,000×g, and the QIAamp™ spin columns were transferred into clean 2-ml collection tubes. The supernatant-containing collection tubes were discarded into a waste bucket. The QIAamp™ spin columns were opened carefully and 500 µl of Wash Buffer 1 (AW1) was added. Tubes were centrifuged for 60 seconds at 6,000×g. The QIAamp™ spin columns were transferred into clean 2-ml collection tubes. The supernatant-containing collection tubes were discarded into a waste bucket. The QIAamp™ spin columns were carefully opened and 500 µl of Wash Buffer 2 (AW2) was added. Tubes were centrifuged for 3 minutes at 10,000×g. The supernatant was aspirated from the collection tubes using either a transfer pipettes or vacuum with trap. The pipette or tip was changed after each aspiration. Tubes were centrifuged for 60 seconds at 6,000×g to eliminate any chance of wash buffer carryover. The QIAamp™ spin columns were transferred into clean 1.5 ml microcentrifuge tubes. The supernatant-containing collection tubes were discarded into a waste bucket. 60 µL of Elution Buffer (AVE) was added to each column. The pipette tip was changed for each tube. The columns were incubated for 60 seconds at room temperature, followed by centrifugation for 60 seconds at 6,000×g. 10 µl of eluted ribonucleic acid was transferred into a new 1.5-ml screw-cap tube for coreceptor utilization analysis. The remaining viral RNA (~48-50 µl) was transferred into another 1.5-ml screw-cap tube for long-term storage at ≤−70° C.

Reverse Transcription (RT) and Polymerase Chain Reaction (PCR)

The purpose of this procedure was to amplify a portion of the envelope gene of Human Immunodeficiency Virus type 1 (HIV-1), using viral RNA extracted from plasma as template. The resulting RT-PCR amplicon was subsequently used for analysis of HIV-1 coreceptor utilization.

Two sets of PCR primers were used:

(SEQ ID NO: 26)
HTA6816F: 5'-CCT GAG CCA TTA CAC AGG CCT GTC CAA AG-3'

(SEQ ID NO: 27)
HTA7359R: 5'-TTA CAG TAG AAA AAT TCC CCT C-3'

(SEQ ID NO: 28)
V3-7092F: 5'-GAA TCT GTA GAA ATT AAT TGT ACA AGA C-3'

(SEQ ID NO: 29)
V3-7232R: 5'-TGC TCT ACT AAT GTT ACA ATG TGC TTG TCT TAT-3'

Reverse Transcriptase (RT) Master Mix Preparation:

GeneAmp RNA OCR core Kit reagents were thawed to room temperature, except for enzymes, which were removed from freezer only when needed. Reagents were mixed by vortexing and then microcentrifuged briefly before placing tubes in an ice bucket. A sterile 1.5 ml microcentrifuge tube was placed in the ice bucket. Enough RT master mix was prepared to accommodate the number of planned reactions plus one (to accommodate pipetting eror), based on the following amounts of reagents per reaction: 2 µl 10×RT-PCR Buffer II, 4 µl 25 mM MgCl, 2 µL 10 mM dCTP, 2 µL 10 mM dGTP, 2 µL 10 mM dTTP, 2 µL 10 mM dATP, 1 µL 50 µM Random Hexamers, 1 µL Rnase Inhibitor (20 U/µl), 1 µL MuLV RT (50 U/µl). Master mix and retainer assembly was transferred to a sterile laminar flow hood.

RNA Template Addition:

Patient RNA was thawed on ice followed by brief microcentrifugation to ensure that all liquid is brought to the bottom. MicroAmp reaction tubes were labeled and placed in retainer/tray assembly. RT master mix was mixed by gently pipetting up and down a few times. 17 µl of master mix was pipetted into each of the reaction tubes. 3 µl of viral RNA extracted from patient samples was added. One extraction positive control (HIV-1 LAV) and one extraction negative control (Sera Care Plasma) were included with each RT-PCR run. Tubes were capped with cap strips and retainer/tray assembly was removed from the laminar flow hood and transferred to thermocycler. The RT reaction mixtures were incubated at 42° C. for 60 minutes followed by heat inactivation at 95° C. for 5 minutes. The completed RT reaction can be stored at 4° C. (short-term) or −20° C. (long-term) until ready for cDNA amplification.

Primary PCR Master Mix Preparation:

GeneAmp RNA PCR Core Kit reagenets were thawed at room temperature, except for enzymes, which were removed from freezer only when needed. Reagents were mixed by vortexing and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipetting error), based on the following amounts of reagents per reaction: 8 µL 10×PCR buffer II, 2 µL 25 mM MgCl$_2$, 1 µL primer HTA6816F (25 µM), primer HTA7359R (25 µM), 67.5 µL sterile water, and 0.5 µL Taq polymerise (5 U/µL). Primary PCR master mix and retainer assembly containing completed RT reactions were transferred to sterile laminar flow hood in template addition area.

cDNA Template Addition:

PCR master mix was mixed by gently gently pipetting up and down a few times. 80 µL of master mix was overlayed into each of the RT reaction tubes, giving a total reaction volume of 100 µL. Tubes were capped with cap strips and retainer/tray assembly was removed from laminar flow hood and transferred to a thermocycler, which was programmed for cDNA amplification as follows: PCR mixtures were pre-incubated at 94° C. for 5 minutes, followed by 35 cycles of three-step incubations at 94° C. for 15 seconds, 55° C. for 30 seconds, and 72° C. for 1 minute, followed by a 5 minute incubation at 72° C. The completed primary PCR reaction was stored at 4° C. (short-term) or −20° C. (long-term) until ready for nested amplification.

Secondary/Nested PCR Master Mix Preparation:

GeneAmp RNA PCR Core Kit reagents were thawed at room temperature, except for enzymes, which were removed from freezer only when needed. Reagents were vortexed to mix and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipetting error), based on the following amounts of reagents per reaction: 10 µL 10×PCR Buffer II, 6 µL 25 mM MgCl$_2$, 4 µL 10 mM dNTP blend, 1 µL V37092F (25 µM), 1 µL V37232R (25 µM), 75.5 µL sterile water, 0.5 µL Taq polymerase (5 U/µL). Primary PCR master mix and retainer assembly containing completed RT reactions were transferred to sterile laminar flow hood in the template addition area.

Secondary/Nested PCR Template Addition:

MicroAmp reaction tubes were labeled and placed in retainer/tray assembly. Secondary/nested PCR master mix was mixed by gently pipetting up and down a few times. 98 µL of master mix was added into each of the reaction tubes. 2 µL of the primary PCR reaction was added to corresponding secondary PCR reaction tube for a total volume of 100 µL. Tubes were capped with cap strips and the retainer/tray assembly was removed from the laminar flow hood and transferred to a thermocycler which was programmed for cDNA amplification as follows: re-incubated at 94° C. for 5 minutes, followed by 35 cycles of three-step incubations at 94° C. for 15 seconds, 55° C. for 30 seconds, 72° C. for 1 minute, followed by a 5 minute incubation at 72° C. The completed primary PCR reaction was stored at 4° C. (short-term) or −20° C. (long-term) until ready for nested amplification.

Sample Preparation for Agarose Gel Analysis:

6× gel-loading buffer was prepared as follows: 0.25% bromophenol blue, 0.25% xylene cyanol, 30% glycerol, and water up to desired final volume. A stock solution can be prepared and stored at room temperature. 20 µL of 6× gel-loading buffer was added to each secondary/nested PCR reaction tube. Samples were mixed by pipetting up and down.

Agarose Gel Preparation:

5×-TBE buffer was diluted to 0.5× with distilled water. Ethidium bromide was added to a final concentration of 0.5 µg/ml. A 4% (w/v) GTG NuSieve agarose solution was prepared by adding 6 g agarose to 150 ml 0.5×TBE/EtBr in a 250 ml glass Erlenmeyer flask. The agarose/TBE solution was gently mixed for 10 minutes at room temperature (to allow the agarose to hydrate), followed by heating in the microwave at 40% power for 10 minutes, mixing occasionally, until all agarose is completely dissolved. The dissolved agarose solution was gently cooled under cold running water and then poured into a previously set-up gel tray (with appropriate size gel comb), while making sure to minimize bubbles. The agarose was allowed to completely solidify for approximately 30-60 minutes at room temperature.

Agarose Gel Electrophoresis:

Once the agarose solidified, the comb was gently removed and the gel apparatus was prepared to receive running buffer. 0.5×TBE buffer, containing 0.5 µg/ml ethidium bromide, was slowly poured into the electrophoresis rig until the gel was completely submerged. 10 µl of the 100-bp DNA ladder was loaded into the first well of the agarose gel. Each secondary/nested PCR sample was loaded into subsequent wells of the agarose gel. The lid was placed on the gel apparatus and the voltage was turned on at 100-200V constant current until the bromophenol blue (lower dye front) reached the end of the gel. Care was taken not to run the gel to long so that the samples were not lost. The gel was visualized on the analytical setting of the UV transilluminator and photographed for record-keeping purposes. The desired PCR amplicon was approximately 140-bp in size.

DNA Extraction:

The gel was visualized using the preparative setting on the UV transilluminator. Each sample band was cut out of the gel with a clean razor blade or scalpel and place in a pre-weighed 1.5 ml microcentrifuge tube. The band was cut as close to its edges as possible, in preparation for the QIAquick separation kit which allows for a maximum of 400 µg of agarose. Blades were changed between bands to avoid sample cross-contamination. Amplified DNA was extracted from each agarose slice using Qiagen's QIAquick separation protocol (e.g. Qiagen's QIAquick Gel Extraction Kit Protocol (March 2001 Handbook)).

Purified DNA was analyzed spectrophotometrically and was adjusted to ~250 ng/µL. Approximately 90 µL DNA was used for the subsequent coreceptor analysis procedures. The purified DNA was transferred to sterile 1.5 ml screw-cap tubes and was either stored at 4° C. (short-term) or –20° C. (long-term) until ready for HTA analysis or TOPO TA cloning.

Polymerase Chain Reaction (RT-PCR) Amplication of Cloned HIV-1 Sequences to Generate Fluorescently-Labeled Probes for Qualitative and Quantitative Coreceptor Utilization Analysis The purpose of this procedure was to amplify a portion of the envelope gene of Human Immunodeficiency Virus type 1 (HIV-1), using cloned plasmid DNA. Fluorescent-labeled PCR primers were used to generate fluorescein-conjugated DNA probes. The resulting probes were subsequently used for qualitative and quantitative analysis of HIV-1 coreceptor utilization. Two sets of fluorescently-labeled primers were used to generate fluorescein-conjugated DNA probes, with the forward primer of each pair covalently linked at the 5' end to fluorescein.

(SEQ ID NO: 28)
5'F*V3-7092F:5'-/56-FAM/ GAA TCT GTA GAA ATT AAT TGT ACA AGA C-3'

(SEQ ID NO: 29)
V3-7232R:5'-TGC TCT ACT AAT GTT ACA ATG TGC TTG TCT TAT-3'

(SEQ ID NO: 30)
5'F*V3HTA-EcoRI-F:5'-/56-FAM/ AAT TCG CCC TTG AAT CTG TAG AAA TTA AT-3'

(SEQ ID NO: 31)
V3HTA-EcoRI-R:5'-AAT TCG CCC TTT TTT GCT CTA CTA ATG-3'

PCR Master Mix Preparation to Generate Probe for Qualitative HTA:

GeneAmp RNA PCR Core Kit reagents were thawed at room temperature, except for enzymes, which were removed from freezer only when needed. Reagents were vortexed to mix and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipeting error), based on the amounts of reagents per reaction as follows: 10 µL 10×PCR buffer II, 6 µL 25 mM MgCI$_2$, 4 µL 10 mM dNTP blend, 1 µL 5'F*V3-7092F (at 25 µM), 1 µl V3-7232R (at 25 µM), 76.5 µL sterile water, 0.5 µL Taq polymerase (5 U/µL). At least four reactions were planned (one for each probe). A negative control containing sterile water instead of plasmid DNA was also prepared. This "qualitative" PCR master mix and retainer tray assembly were transferred to a sterile laminar flow hood in the template addition area.

PCR Master Mix Preparation to Generate Probe for Quantitative HTA:

GeneAmp RNA PCR Core Kit reagents were thawed at room temperature, except for enzymes, which were removed from freezer only when needed. Reagents were vortexed to mix and then briefly microcentrifuged and placed in an ice bucket. A sterile 1.5 ml microcentrifuge tube was placed in the ice bucket. Enough cDNA amplification/primary PCR master mix was prepared to accommodate the number of planned reactions plus one (to accommodate pipeting error), based on the amounts of reagents per reaction as follows: 10 µL 10×PCR buffer II, 6 µL 25 mM MgCI$_2$, 4 µL 10 mM dNTP blend, 1 µL 5° F.*V3HTA-EcoRI-F (at 25 µM), 1 µl V3HTA-EcoR1-R (at 25 µM), 76.5 µL sterile water, 0.5 µL Taq polymerase (5 U/µL). At least four reactions were planned (one for each probe). A negative control containing sterile water instead of plasmid DNA was also prepared. This "quantitative" PCR master mix and retainer tray assembly were transferred to a sterile laminar flow hood in the template addition area.

PCR Template Addition:

MicroAmp reaction tubes were labeled and placed in retainer/tray assembly. Each of the "qualitative" and "quantitative" PCR master mixes were mixed by gently pipetting up and down a few times. 99 µL of each master mix were added into reaction tubes. 1 µL of each plasmid DNA template (SF$_{162}$, JR-CSF, Sw54, and Sw87; derived from primary HIV-1 strains of the same name) was added to corresponding PCR reaction tube for a total volume of 100 µL. Tubes were capped with cap strips and retainer/tray assembly was removed from laminar flow hood and transferred to thermocycler, which was programmed for cDNA amplification as follows: pre-incubation at 94° C. for 5 minutes, followed by 35 cycles of three-step incubations at 94° C. for 15 seconds, 55° C. for 30 seconds, 72° C. for 1 minute, followed by a 5 minute incubation at 72° C. The completed PCR reaction can be stored at 4° C. (short-term)

or −20° C. (long-term) until ready for cDNA amplification. PCR products were analyzed and gel-purified on a 4% agarose gel as described above.

Qualitative HIV-1 Coreceptor Utilization Analysis Using a Heteroduplex Tracking Assay (HTA)

This assay uses a heteroduplex tracking (HTA) technique to analyze a portion of the Human Immunodeficiency Virus type I (HIV-1) envelope gene encompassing the key determinates of coreceptor utilization. Sequence difference between CCR5— and CXCR4-using variants result in distinct heteroduplex electrophoretic mobilities that allow the overall number and relative proportion of distinct variants to be estimated, even in samples consisting of heterogeneous CCR5 and CXCR4 pools. Plasma specimens showing heteroduplex patterns indicative of CXCR4 strains are then subjected to further analysis to quantitate the portion of CCR5 and CXCR4 viruses in the patient quasispecies. Interpretation of the gels is based on the banding pattern seen in each gel lane. The absence of clearly distinct heteroduplex bands is indicative of a predominance of CCR5-utilizing strains of HIV-1. A schematic representation of qualitative HTA analysis of four different of targets: probe only, a CCR5 virus, an CXCR4 virus, and a heterogeneous mix of CCR5 and CXCR4 viruses, is shown in FIG. 2.

Preparation of Non-Denaturing Polyacrylamide Gels:

Glass plates were cleaned with Sparkleen, rinsed with water (first tap water and then deionized water), and either allowed to air-dry or were blotted using lint-free wipes. The plates were made to be completely clean and free of grease spots to prevent air bubbles from forming in the gel. Spacers were placed in between glass plates (one on each side and one on bottom) and plates were sealed together according the electrophoresis rig manufacturer's recommendations (i.e., inside a gel bag for an Owl rig). The volume of acrylamide gel solution required was calculated. For example, a single 20×20 cm gel with 1.5 mm spacers required approximately 75 mL of gel solution. Enough 12% acrylamide solution was prepared to accommodate the number of planned gels, based on the following amounts of reagents per 75 mL gel: 22.5 mL 40% (29:1) acrylamide/bis-acrylamide stock solution, 36.9 mL deionized water, 15 mL 5× Tris-Borate-EDTA (TBE) stock buffer, 52.5 µL TEMED, 525 µL10% AMPS, freshly prepared in deionized water. Acrylamide solution was swirled gently to mix or was mixed using a spin bar/magnetic mixer while being careful not to introduce any bubbles into the solution. Using a 25 mL pipette, the acrylamide solution was gently poured into the space between the two glass plates filling the space almost to the top. The appropriate comb was gently inserted, being careful not to trap air bubbles under the teeth. The acrylamide was allowed to polymerize for 60 minutes at room temperature, which was deemed to be complete when schlieren (e.g., distortion) lines were visible just beneath the teeth of the comb. If necessary, polymerized gels were stored for 1-2 days at this point by: 1) surrounding the comb and top of the gel with paper towels soaked in 1×TBE; 2) sealing the entire gel with saran wrap; and 3) placing gel at 4° C. until ready for use. Gels that were ready for use were attached to the electrophoresis tank according to the manufacturer's recommendations. The reservoirs of the electrophoresis tank were filled with 1×TBE (made with 1 part 5×TBE and 4 parts deionized water). A bent Pasteur pipette was used to remove any air bubbles trapped beneath the bottom of the gel, which would have interfered with the uniform running of samples through the polyacrylamide. The comb was removed and the wells were rinsed out with 1×TBE.

Heteroduplex Formation:

If necessary, prepared probe and target DNA were thawed at room temperature. Probe and target DNA were vortexed to mix and then microcentrifuged briefly and placed in an ice bucket. Between two and four sterile 1.5 ml microcentrifuge tubes were placed in the ice bucket (one tube per probe). Enough HTA annealing mix was prepared to accommodate the number of planned reactions plus one (to accommodate pipeting error), based on the following amounts of reagents per reaction: 3 µL 10×HTA annealing buffer, 5 µL FITC-labeled probe, 2 µL sterile water. MicroAmp reaction tubes were labeled and placed in retainer/tray assembly. HTA annealing mix was mixed by gently pipeting up and down a few times. 10 µL of master mix were aliquotted into each of the reaction tubes. 20 µL of viral RNA extracted from patient samples was then added. There were two to four reactions for each patient sample—one for each probe used. One positive control (the purified HIV-1 LAV extraction control) and one negative control (water only) were included in each run. These controls were also used to determine the amount of homoduplex and heteroduplex DNA present in each experiment. Tubes were capped with cap strips and the retainer/tray assembly was removed from the laminar flow hood and transferred to a thermocycler. The HTA annealing reaction was run for 2 minutes at 94° C., followed by quenching to 4° C. (short-term). The resulting reactions were placed on ice and immediately loaded on a 12% non-denaturing polyacrylamide gel.

Polyacrylamide Gel Electrophoresis:

6× gel-loading buffer was prepared by combining: 0.25% bromophenol blue, 0.25% xylene cyanol, 30% glycerol, water up to desired final volume. A stock solution may be prepared and stored at room temperature. 6 µL of 6× gel-loading buffer was added to each HTA annealing reaction tube and was mixed by pipeting up and down. Using a sequencing gel loading tip, the entire HTA annealing reaction was gently loaded into the polyacrylamide gel wells. Care was taken to load the samples as compactly and as neatly as possible, trying to avoid air bubbles that may blow the sample out of the well. Care was also taken to load the gel as quickly as possible in order to prevent the samples from diffusing from the wells. The electrodes were connected to the power supply and the gel was run at a constant voltage until the last of the upper xylene cyanol dye front runs off the bottom of the gel (approximately 6 hours at 250V or overnight at 90V), or until the polyacrylamide gel marker dyes had migrated the desired distance. The gels were water cooled to prevent "smiling". The electric power was turned off and the leads disconnected. The electrophoresis buffer from the reservoirs was discarded and the glass plates detached. Using a thin spatula, a corner of the upper glass plate was gently lifted. The gel remained attached to the lower plate, allowing the upper plate to be smoothly pulled away. The spacers were removed. Using a scalpel or razor blade, the lower right-hand corner of the gel was marked for orientation. The gel was covered with saran wrap to prevent drying out or accumulation of dust until scanning was performed.

Scanning and Gel Analysis:

The FluorImager 595 was warmed up at least 15 minutes prior to use. The imager controls were adjusted to the following settings: 1) single label dye; 2) 488 nm excitation;

3) no emission filter; 4) no calibration; 5) 1000V PMT; 6) high sensitivity; 7) 200 μm pixels; and 8) 16-bit resolution. The user interface was also set to transfer the resulting image into the ImageQuaNT™ software package. The FluorImager scanning tray was gently washed with deionized water, then rinse with 70% ethanol and allow to air dry. The gel was gently lifted from the glass plate and transferred to the FluorImager scanning tray. The analysis window was adjusted using the computer interface, and then the gel was scanned. ImageQuaNT™ software package was used to display the gel image, once the scan was complete. The software was used to adjust the brightness and contrast of the gel, if necessary, and then to save the image as a TIFF file. Images were transferred to a PhotoShop®-enabled desktop computer for further processing and analysis. A hard copy image of each gel was also stored in the appropriate laboratory notebook.

Interpretation of the gels is based on the banding pattern seen in each gel lane. The absence of clearly distinct heteroduplex bands is indicative of a predominance of CCR5-utilizing strains of HIV-1. Patient samples that contain only CCR5 viruses were assigned a QXR value of 1.0 [where QXR=(number of CCR5 clones)/(total number of clones analyzed)]. Specimens with detectible CXCR4 virus, on the other hand, were subjected to further quantitative analysis to quantitate the portion of CCR5 and CXCR4 viruses in the patient quasispecies using the procedures outlined below (Example 2, Quantitative HIV-1 Coreceptor Utilization Analysis Using an HTA).

Example 6

Quantitative Coreceptor Utilization Analysis using a Heteroduplex Tracking Assay (HTA)

Cloning of HIV-1 Envelope Sequences for Quantitative Coreceptor Utilization Analysis:

The purpose of this procedure was to clone HIV-1 envelope sequences for quantitative coreceptor utilization anaylsis. HIV-1 RNA isolated and amplified from patient plasma was cloned into a plasmid vector (pCR® 2.1-TOPO®, Invitrogen), used to transform chemically competent *Escherichia coli*, and plated onto selective bacterial media.

Cloning reagents were thawed at room temperature on ice, except TOPO™ vector, which was removed from the freezer only when needed. Reagents were vortexed and microcentrifuged briefly and placed in an ice bucket. Enough sterile 1.5 ml tubes were placed on ice to accommodate the number of planned cloning reactions, including one positive and one negative control. The following reagents per reaction were gently mixed and incubated for 5 minutes at room temperature and then placed on ice: 4 μL extracted DNA amplicon/sterile water, 1 μL salt solution, and 1 μL TOPO™ vector. Enough OneShot® *E. coli* cells were thawed on ice to accommodate the number of planned cloning reactions. 2 μL of the TOPO® cloning reaction was added to a vial of OneShot® *E. coli* and mixed gently using a pipette tip. *E. Coli* was incubated on ice for 30 minutes and heat-shocked for 30 seconds at 42° C. 250 μL of room temperature SOC medium was added to the cells. Tubes were capped and incubated at 37° C. with gentle shaking for 1 hour. LB/ampicillin/X-gal plates were removed from refrigerator and pre-warmed to 37° C. The entire transformation mixture was spread on the pre-warmed LB/ampicillin/X-gal plates, allowed to absorb to the plate for 5 minutes, and then the plate was inverted, labeled appropriately, and incubated overnight at 37° C. After 16 hours, plates were removed from the incubator and examined for white colonies. The number of blue and white colonies on each plate were counted and recorded. Plates were wrapped in parafilm and stored at 4° C. until ready for use.

Isolation, Preparation, and Screening of Plasmid DNA Encoding Cloned HIV-1 Envelope Sequences for Quantitative Coreceptor Utilization Analysis The purpose of this procedure was to prepare high quality plasmid DNA encoding cloned HIV-1 envelope sequences for quantitative coreceptor utilization analysis. HIV-1 RNA isolated and amplified from patient plasma was cloned into a plasmid vector, grown overnight in 1-3 mL of *Escherichia coli* bacterial culture, and purified using a commercially available plasmid miniprep kit (Perfectprep®, Eppendorf, Westbury, N.Y.). Analysis for the viral specific sequences was carried out by digestion of the recombinant plasmid with restriction enzyme EcoR1 (20 U/μL).

On day 1, transformants were picked for overnight growth as follows. LB/ampicillin broth was warmed to 37° C. and LB agar plates containing *E. coli* transformants were removed from 2-8° C. In a sterile environment using sterile technique, 3 mL of LB/ampicillin broth were added to the appropriate number of 15 mL tubes (20 tubes/plate) by pipette and 20 white or light blue colonies per plate were picked using a P20E pipet tip. Colonies were picked at random, taking a single colony from each of twenty identical regions of the LB agar plate. Each tube of LB/ampicillin broth was inoculated with transformed bacteria using a single P20E tip. Caps were tightened and tubes were placed in a pre-warmed shaking incubator. Cultures were grown overnight (8-16 hours) at 37° C. with gentle shaking (approximately 125-250 rpm).

On day 2, plasmid DNA from each overnight culture was purified using Eppendorf's Perfectprep® Plasmid Prep protocol as follows. 1.5 ml of each overnight culture was transferred to a 1.5 ml microcentrifuge tube and centrifuged for 1 minute at 14K rpm to pellet bacterial cells. Supernatant was carefully aspirated from each microcentrifuge tube using a vacuum trap, leaving the bacterial pellet undisturbed. The pelleted bacteria was resuspended in 100 μl of Solution 1 (whose composition is a trade secret but is likely to contain 25 mM Tris (pH 8.0), 50 mM glucose, 10 mM EDTA, and 5 mg/ml lysozyme) by shaking tubes in a benchtop microcentrifuge tube shaker for 1 minute or until the resuspended mixture was of a smooth and even consistency without clumps (in order to obtain higher yields of plasmid DNA. Subsequently, 100 μl of Solution 2 (whose composition is a trade secret but is likely to contain 0.2 N NaOH and 1% sodium lauryl sulfate) was introduced to resuspended bacteria and mixed several times by repeated gentle inversion of the tube in order to lyse the bacteria, until lysate was relatively clear with no visible clumps of cell material. In order to neutralize the alkaline lysis buffer, 100 μl Solution 3 (whose composition is a trade secret but is likely to contain 3 M sodium acetate) was added to each tube and tubes were mixed several times by repeated gentle inversion until a whitish granular or curd-like precipitate appeared. Bacterial lysates were clarified by centrifugation for 1 minute at 14K rpm, allowing pelleting of the bacterial cell wall debris, precipitated proteins and chromosomal DNA. Using a sterile pipet, each bacterial supernatant was transferred into spin columns placed in collection tubes. The DNA Binding Matrix suspension was thoroughly mixed by vortexing until the resuspended binding matrix had a whitish and somewhat cloudy appearance. Where the guanidinium present in the matrix suspension crystallized, as indicated by the presence of long bright crystals, tubes were heated at 37° C. to re-dissolve. 450 µl DNA Binding Matrix was added to the supernatant in each spin column and tubes were mixed by capping the spin column and vigorously inverting the column/collection tube assembly, allowing plasmid DNA to attach to the DNA Binding Matrix, followed by centrifugation of the column/collection tube for 1 minute at 14K rpm. The filtrate was aspirated using a vacuum trap, and then the spin column was placed back into the collection tube. The Purification Solution was diluted by combining 1 part solution concentrate with 1 part absolute ethanol. Diluted purification solution was freshly prepared before use. 400 µl diluted purification solution was added to each spin column, which was capped and briefly shaken before centrifugation for 1 minute at 14K rpm. Filtrate from the spin column was aspirated using a vacuum trap after which spin columns were placed back into collection tubes and centrifuged for an additional minute at 14K rpm to remove any residual purification solution. Each spin column was next transferred to a fresh collection tube and 50 µL of Rnase-free water (Sigma) was added. Column/collection tube assemblies were capped and briefly vortexed before being centrifuged for 1 minute at 14K rpm. Spin columns were discarded and collection tubes capped and labeled. The eluted plasmid DNA was used for screening, or was stored at 4° C. (short-term) or −20° C. (long-term).

Screening of Plasmids by Restriction Enzyme Digestion:

EcoRI enzyme was removed from the freezer only when needed. 10× EcoRI digestion buffer was thawed at room temperature then vortexed to mix and microcentrifuged briefly before being placed in an ice bucket. A sterile 1.5 ml microcentrifuge tube was also placed in the ice bucket. Digests were performed in duplicate (one digest for agarose gel analysis and one digest for quantitative HTA analysis), therefore enough master mix was prepared to accommodate the number of planned digests (in duplicate) plus one (to accommodate pipeting error) based on the following amounts of reagents per reaction: 2.5 µL 10× EcoRI buffer, 17.5 µL sterile water and 1 µL EcoRI (20 U/µL). MicroAmp reaction tubes were labeled, placed in retainer/tray assembly, and after mixing the digestion master mix by gently pipeting up and down a few times, 21 µL of master mix was added into each of the reaction tubes followed by 4 µL of purified plasmid DNA (to the corresponding reaction tube) for a total volume in each tube of 25 µL. Tubes were capped with strips and transferred to the thermocycler, which was programmed for EcoRI digestions as follows: 37° C. for 37 minutes followed by 95° C. for 1 minute. The completed restriction enzyme digests can be stored at 4° C. (short-term) or −20° C. (long-term) until ready for gel and HTA analysis.

Sample Preparation for Agarose Gel Analysis:

6× gel-loading buffer was prepared as follows: 0.25% bromophenol blue, 0.25% xylene cyanol, 30% glycerol, and water up to desired final volume. A stock solution can be prepared and stored at room temperature. 5 µL of 6× gel-loading buffer was added to each digest for gel analysis and mixed by pipetting up and down. Digests, including duplicates, were stored at either 4° C. (short-term) or −20° C. (long-term) until ready for HTA analysis.

Agarose Gel Preparation:

5×-TBE buffer was diluted to 0.5× with distilled water. Ethidium bromide was added to a final concentration of 0.5 µg/ml. A 4% (w/v) GTG NuSieve agarose solution was prepared by adding 6 g agarose to 150 ml 0.5×TBE/EtBr in a 250 ml glass Erlenmeyer flask. The agarose/TBE solution was gently mixed for 10 minutes at room temperature (to allow the agarose to hydrate), followed by heating in the microwave at 40% power for 10 minutes, mixing occasionally, until all agarose is completely dissolved. The dissolved agarose solution was gently cooled under cold running water and then poured into a previously set-up gel tray (with appropriate size gel comb), while making sure to minimize bubbles. The agarose was allowed to completely solidify for approximately 30-60 minutes at room temperature.

Agarose Gel Electrophoresis:

Once the agarose solidified, the comb was gently removed and the gel apparatus was prepared to receive running buffer. 0.5×TBE buffer, containing 0.5 µg/ml ethidium bromide, was slowly poured into the electrophoresis rig until the gel was completely submerged. 10 µl of the 100-bp DNA ladder was loaded into the first well of the agarose gel. Each secondary/nested PCR sample was loaded into subsequent wells of the agarose gel. The lid was placed on the gel apparatus and the voltage was turned on at 100-200V constant current until the bromophenol blue (lower dye front) reached the end of the gel. Care was taken not to run the gel to long so that the samples were not lost. The gel was visualized on the analytical setting of the UV transilluminator and photographed for record-keeping purposes. The desired band was approximately 160 bp in size. An additional band, representing linearized TOPO TA vector was also seen. The coreceptor utilization profile of positive transformants was then analyzed by HTA.

Quantitative Analysis Using an HTA of HIV-1 Coreceptor Utilization

This assay uses the heteroduplex tracking (HTA) technique described in Example 1 to analyze a portion of the Human Immunodeficiency Virus type 1 (HIV-1) envelope gene encompassing the key determinates of coreceptor utilization. Individual clones from patient plasma specimens which showed heteroduplex patterns indicative of CXCR4 strains were subjected to analysis to accurately quantitate the portion of CCR5 and CXCR4 viruses in the patient quasispecies. DNA heteroduplex tracking analysis was performed with the coreceptor utilization profile of a minimum of twenty positive transformants from each patient sample determined by using two probes to screen each clone. Probes were prepared from one laboratory CCR5 isolate (SF162 or JR-CSF) and one primary CCR5 isolate (Sw54 or Sw87). The QXR value for each patient specimen was then calculated based on the number of CCR5-specific clones obtained from each sample as follows: QXR=(number of CCR5 clones)/(total number of clones analyzed). FIG. 1 is a schematic representation of HTA analysis of four different targets: probe only, a CCR5 virus, a CXCR4 virus, and mixed quasispecies containing both CCR5 and CXCR4 viruses.

Example 7

Validation Experiments

PCR Primer Design

A common problem is low or no target DNA yield following PCR, reflecting either PCR efficiency or sample preparation problems. This problem was alleviated in part by use of a commercially available RNA extraction kit (Qiagen Viral RNA Kit), and in part by use of a small amount of pooled HIV-1 LAV, which is always simultaneously extracted as a positive RNA control. This practice is part of our standard operating procedure.

Primers used herein were designed to match the lade B consensus sequence as posted on the Los Alamos National Laboratories HIV database. Using this primer set, we currently have a success rate of 98.4% in amplifying envelope sequences from patient samples with a viral load of at least 1000 copies per milliliter of plasma.

Variant Sampling

Correct sampling is a recurring and frequently overlooked potential problem in subcloning and sequencing analyses of complex populations. Previously, we circumvented this problem by sequencing subclones derived from multiple independent PCR's or sequencing the dilution end point directly. For genetic differences in quasispecies detected as changes in HTA patterns to be significant, the populations being compared must be appropriately sampled. Any claims of quasispecies changes using HTA or other methods of direct population analyses must be substantiated through reproducibility of the results using the product of duplicate, independent amplifications to document proper sampling. To ensure proper variant sampling using our technique, we have compared the HTA results from independent duplicate PCR's. We ran a series of HTA's using different amounts of input template and multiple parallel amplifications to prove that we can consistently amplify all of the majority and minority variants in a patient sample. Three levels of sequence difference between target DNA mixtures were selected to span the diversity found in the HIV-1 envelope gene. Duplicate 10-fold serial dilutions of viral RNA were then amplified by PCR and analyzed by HTA using our various probes. We saw identical HTA patterns in each independent PCR, indicating reproducible and therefore correct sampling of the target populations. These studies also were repeated using various biological and molecular clones derived from primary isolates from patients previously examined in our treatment study (1). Finally, we repeated these sampling studies using RNA from primary patient isolates of known and unknown coreceptor usage. In each case, analysis of duplicate, independent PCR's demonstrated that our primers and our optimized PCR reaction conditions reproducibly amplify a mixture of HIV-1 variants that adequately reflects the population in the original sample.

Limits of Detection

The main advantage of HTA is its ability to simultaneously analyze multiple genetic variants coamplified by PCR. Using optimized reaction conditions, HTA's can be used to detect variants that represent less than 1% of the total quasispecies population (5). The ability of our coreceptor-specific HTA to detect rare variants has been examined by reconstituting mixtures of virus using laboratory isolates with known coreceptor usage. The sensitivity of the HTA method to detect R5 and X4 isolates was independently ascertained by using reconstituted samples with QXR values at or near 0 and 1, respectively. These experiments have demonstrated that we can routinely and reproducibly detect CCR5 and CXCR4 variants that represent as little as 0.2% of the total viral population.

Assay Validation Using Patient Isolates

Over the last five years we have isolated a large number of biologic and molecular clones of HIV-1, allowing us to compare genotypic predictions of coreceptor usage (either by performing V3 loop sequencing or by using our HTA method) with phenotypically-determined coreceptor preference.

Previously, we used a rapid RT-PCR based genotypic method to measure QXR, the proportion of HIV-1 utilizing CCR5 or CXCR4 as a coreceptor. This method relied on sequence analysis of the V3 region of the HIV-1 envelope gene to determine QXR. A total of 424 phenotypically-characterized biological and molecular clones of HIV-1 were analyzed, yielding the following data:

|  |  | Phenotypic Result | |
|---|---|---|---|
|  |  | CCR5-using | CXCR4-using |
| Genotypic Prediction by V3 Sequencing | CCR5-using | 225 | 8 |
|  | CXCR4-using | 12 | 179 |

For detection of CCR5 strains of HIV-1, this sequencing-based approach thus achieves 94.9% sensitivity and 95.7% specificity.

A subset of clones from this sample set has also been examined using the newer HTA approach. A total of 392 clones have been analyzed:

|  |  | Phenotypic Result | |
|---|---|---|---|
|  |  | CCR5-using | CXCR4-using |
| Genotypic Prediction by HTA | CCR5-using | 232 | 0 |
|  | CXCR4-using | 3 | 157 |

For detection of CCR5 strains of HIV-1, the HTA method achieves ~100% sensitivity and specificity. Conversely, for detection of CXCR4 strains of HIV-1, this method attains ~100% sensitivity and 98.7% specificity. The predictive values for detecting CCR5 and CXCR4 strains are 100% and 98.1%, respectively.

Having thus described in detail preferred embodiments of the present invention, it is to be understood that the invention defined by the appended claims is not to be limited to particular details set forth in the above description as many apparent variations thereof are possible without departing from the spirit or scope of the present invention.

The invention claimed is:

1. A diagnostic method for determining suitability of antiretroviral therapy by measuring HIV using the CCR5 coreceptor and the CXCR4 coreceptor in a patient-derived biological sample, comprising:
Screening patient-derived HIV with a heteroduplex tracking assay to determine the CCR5 coreceptor usage and CXCR4 coreceptor usage;
wherein CXCR4 coreceptor use indicates an unsuitable antiretroviral therapy and exclusive use of CCR5 coreceptor indicates a suitable antiretroviral therapy.

2. The method of claim 1, wherein the biological sample is a bodily fluid.

3. The method of claim 1, wherein the individual molecular clones each comprise a DNA sequence corresponding to a portion of the HIV genome, the DNA sequence comprising at least a portion of the genetic determinants of coreceptor usage.

4. The method of claim 3, wherein the genetic determinants are derived from the env gene.

5. The method of claim 1, wherein the molecular clones each are derived from RNA of the patient-derived HIV and correspond to the HIV genome or a portion thereof and which comprise the genetic determinants of coreceptor usage or a portion thereof.

6. The method of claim 5, wherein the molecular clones are prepared by amplifying viral RNA obtained from the patient-derived biological sample by RT-PCR to obtain viral cDNA, and performing multiple PCR's on the cDNA using at least one set of oligonucleotide primers.

7. The method of claim 6, wherein at least one set of oligonucleotide primers consists of SEQ ID NO: 26 and SEQ ID NO: 27.

8. The method of claim 6, wherein the at least one set of oligonucleotide primers includes a second set of oligonucleotide primers, the second set consisting of SEQ ID NO: 28 and SEQ ID NO: 29.

9. The method of claim 1, wherein the number of individual molecular clones is at least 20.

10. The method of claim 1, wherein the heteroduplex tracking assay comprises the steps of:
(a) amplifying the individual molecular clone or a portion thereof by PCR to provide amplified DNA comprising the genetic determinants of coreceptor usage or a portion thereof;
(b) forming a population of heteroduplex molecules by contacting the amplified DNA with a labeled probe complementary to the amplified DNA under conditions sufficient to form heteroduplexes;
(c) separating the population of heteroduplex molecules using a separation means;
(d) detecting the presence or absence of heteroduplex molecules;
wherein the presence or absence of heteroduplex molecules reveals coreceptor usage.

11. The method of claim 10, wherein the labeled probe is derived from a known HIV-1 CCR5-utilizing clone.

12. The method of claim 10, wherein the labeled probe is derived from a known HIV-1 CXCR4-utilizing clone.

13. The method of claim 10, wherein the labeled probe comprises a detectable moiety, a radioisotope, biotin, a fluorescent moiety, a fluorophore, a chemiluminescent moiety, or an enzymatic moiety.

14. The method of claim 1, wherein the method is used (a) to determine when to start or change antiretroviral treatment or (b) to monitor the efficacy of antiretroviral treatment.

15. A diagnostic method for determining suitable antiretroviral therapy by determining CCR5 and/or CXCR4 coreceptor usage of patient-derived HIV, comprising:
Analyzing a portion of the genome of the patient-derived HIV with a heteroduplex tracking assay to detect coreceptor usage under conditions sufficient to reveal coreceptor usage;
wherein CXCR4 coreceptor use indicates an unsuitable antiretroviral therapy and exclusive use of CCR5 coreceptor indicates a suitable antiretroviral therapy.

16. The method of claim 15, wherein the patient derived HIV is isolated from a bodily fluid.

17. The method of claim 15, wherein the portion of the genome of the HIV comprises the genetic determinants of coreceptor usage or a portion thereof.

18. The method of claim 17, wherein the genetic determinants are derived from the env gene.

19. The method of claim 15, wherein the portion of the genome of the HIV is prepared by PCR using at least one set of oligonucleotide primers.

20. The method of claim 19, wherein the at least one set of oligonucleotide primers includes SEQ ID NO: 26 and SEQ ID NO: 27.

21. The method of claim 19, wherein the at least one set of oligonucleotide primers includes SEQ ID NO: 28 and SEQ ID NO: 29 as second set of oligonucleotide primers.

22. The method of claim 15 wherein the heteroduplex tracking assay comprises the steps of:
(a) Amplifying a portion of the genome of the patient-derived HIV by RT-PCR followed by PCR to provide amplified DNA comprising the genetic determinants of coreceptor usage;
(b) forming a population of heteroduplex molecules by contacting the amplified DNA with a labeled probe complementary to the amplified DNA under conditions sufficient to form heteroduplexes;
(c) separating the population of heteroduplex molecules using a separation means; and
(d) detecting the presence or absence of heteroduplex molecules specific to either CCR5 or CXCR4 or to both CCR5 and CXCR4;
wherein the presence or absence of heteroduplex molecules reveals coreceptor usage.

23. The method of claim 22, wherein the labeled probe is derived from a known HIV-1 CCR5-utilizing clone.

24. The method of claim 22, wherein the labeled probe is derived from a known HIV-1 CXCR4-utilizing clone.

25. The method of claim 22, wherein the labeled probe comprises a detectable moiety, a radioisotope, biotin, a fluorescent moiety, a fluorophore, a chemiluminescent moiety, or an enzymatic moiety.

26. The method of claim 15, wherein the method is used (a) to determine a suitable antiretroviral treatment regimen or (b) to monitor the efficacy of antiretroviral treatment.

27. The method of claim 2 wherein the body fluid is blood, plasma, or spinal fluid.

28. The method of claim 16 wherein the body fluid is blood, plasma, or spinal fluid.

* * * * *

UNITED STATES PATENT AND TRADEMARK OFFICE
CERTIFICATE OF CORRECTION

| | | |
|---|---|---|
| PATENT NO. | : 7,344,830 B2 | Page 1 of 1 |
| APPLICATION NO. | : 11/333073 | |
| DATED | : March 18, 2008 | |
| INVENTOR(S) | : Sean Philpott et al. | |

It is certified that error appears in the above-identified patent and that said Letters Patent is hereby corrected as shown below:

Column 1, line 31, please replace the following paragraph:

"STATEMENT OF RIGHTS TO INVENTIONS MADE UNDER FEDERALLY SPONSORED RESEARCH

This work was supported by the government, in part, by Grant U01AI35004 from the National Institute for Allergy and Infectious Diseases and a National Research Service Award (1F32HD08478-01) from the National Institute of Child Health and Human Development. The government may have certain rights to this invention."

with

--STATEMENT REGARDING FEDERALLY SPONSORED RESEARCH OR DEVELOPMENT

This invention was made with government support under AI0135004 & HD008478 awarded by the National Institutes of Health. The government has certain rights in the invention.--

Signed and Sealed this
Twelfth Day of February, 2013

Teresa Stanek Rea
*Acting Director of the United States Patent and Trademark Office*

SEQUENCE LISTING

<160> NUMBER OF SEQ ID NOS: 40

<210> SEQ ID NO 1
<211> LENGTH: 35
<212> TYPE: PRT
<213> ORGANISM: Human immunodeficiency virus

```
<400> SEQUENCE: 1

Cys Ile Arg Pro Asn Asn Asn Thr Arg Thr Ser Ile Arg Ile Gly Pro
  1               5                  10                  15

Gly Gln Ala Phe Tyr Ala Thr Gly Asn Ile Ile Gly Asp Ile Arg Gln
                 20                  25                  30

Ala Tyr Cys
        35

<210> SEQ ID NO 2
<211> LENGTH: 35
<212> TYPE: PRT
<213> ORGANISM: Human immunodeficiency virus

<400> SEQUENCE: 2

Cys Ile Arg Pro Asn Asn Asn Thr Arg Thr Ser Ile Arg Ile Gly Pro
  1               5                  10                  15

Arg Gln Ala Phe Tyr Ala Thr Gly Asn Ile Ile Gly Asp Ile Arg Gln
                 20                  25                  30

Ala Tyr Cys
        35

<210> SEQ ID NO 3
<211> LENGTH: 35
<212> TYPE: PRT
<213> ORGANISM: Human immunodeficiency virus

<400> SEQUENCE: 3

Cys Ile Arg Pro Asn Asn Asn Thr Arg Thr Ser Ile Arg Ile Gly Pro
  1               5                  10                  15

Gly Gln Ala Phe Tyr Ala Thr Gly Asn Ile Val Gly Asp Ile Arg Gln
                 20                  25                  30

Ala Tyr Cys
        35

<210> SEQ ID NO 4
<211> LENGTH: 27
<212> TYPE: PRT
<213> ORGANISM: Human immunodeficiency virus

<400> SEQUENCE: 4

Arg Lys Ser Val His Ile Gly Pro Gly Gln Ala Phe Tyr Ala Thr Gly
  1               5                  10                  15

Asp Ile Ile Gly Asn Ile Arg Lys Ala His Cys
                 20                  25

<210> SEQ ID NO 5
<211> LENGTH: 35
<212> TYPE: PRT
<213> ORGANISM: Human immunodeficiency virus

<400> SEQUENCE: 5

Cys Thr Arg Pro Asn Asn Asn Thr Arg Lys Ser Val His Ile Gly Pro
  1               5                  10                  15

Gly Gln Ala Phe Tyr Ala Thr Gly Asp Ile Ile Gly Asn Ile Arg Lys
                 20                  25                  30

Ala His Cys
        35

<210> SEQ ID NO 6
```

```
<211> LENGTH: 35
<212> TYPE: PRT
<213> ORGANISM: Human immunodeficiency virus

<400> SEQUENCE: 6

Cys Thr Arg Pro Asn Asn Asn Thr Arg Lys Ser Val His Ile Gly Pro
 1               5                  10                  15

Gly Gln Ala Phe Tyr Ala Thr Gly Asp Ile Ile Gly Asn Ile Arg Gln
            20                  25                  30

Ala His Cys
        35

<210> SEQ ID NO 7
<211> LENGTH: 35
<212> TYPE: PRT
<213> ORGANISM: Human immunodeficiency virus

<400> SEQUENCE: 7

Cys Thr Arg Pro Asn Asn Asn Thr Arg Lys Ser Val His Ile Gly Pro
 1               5                  10                  15

Gly Gln Ala Phe Tyr Ala Thr Gly Asp Ile Ile Gly Asn Met Arg Lys
            20                  25                  30

Ala His Cys
        35

<210> SEQ ID NO 8
<211> LENGTH: 35
<212> TYPE: PRT
<213> ORGANISM: Human immunodeficiency virus

<400> SEQUENCE: 8

Cys Thr Arg Pro Ile Asn Asn Arg Arg Lys Ser Ile His Met Gly Pro
 1               5                  10                  15

Gly Gln Ala Phe Tyr Gly Thr Asp Asp Ile Ile Gly Asp Ile Arg Lys
            20                  25                  30

Ala Arg Cys
        35

<210> SEQ ID NO 9
<211> LENGTH: 36
<212> TYPE: PRT
<213> ORGANISM: Human immunodeficiency virus

<400> SEQUENCE: 9

Cys Thr Arg Pro Ser Asn Asn Arg Arg Lys Ser Ile His Lys Gly Asp
 1               5                  10                  15

Gln Asp Lys His Ser Met Glu His Asp Asp Val Ile Gly Asp Ile Arg
            20                  25                  30

Lys Ala Arg Cys
        35

<210> SEQ ID NO 10
<211> LENGTH: 35
<212> TYPE: PRT
<213> ORGANISM: Human immunodeficiency virus

<400> SEQUENCE: 10

Cys Thr Arg Pro Ile Asn Asn Arg Arg Lys Ser Ile His Ile Gly Pro
 1               5                  10                  15

Gly Gln Ala Phe Tyr Gly Thr Asp Ile Ile Gly Asp Ile Arg Gln
            20                  25                  30
```

Ala His Cys
        35

<210> SEQ ID NO 11
<211> LENGTH: 34
<212> TYPE: PRT
<213> ORGANISM: Human immunodeficiency virus

<400> SEQUENCE: 11

Cys Ile Arg Pro Asn Asn Asn Thr Arg Gln Ser Val His Ile Gly Pro
 1               5                  10                  15

Gly Gln Ala Leu Tyr Thr Thr Glu Ile Ile Gly Asp Ile Arg Lys Ala
            20                  25                  30

His Cys

<210> SEQ ID NO 12
<211> LENGTH: 35
<212> TYPE: PRT
<213> ORGANISM: Human immunodeficiency virus

<400> SEQUENCE: 12

Cys Thr Arg Pro Asn Asn Asn Thr Ile Thr Ser Ile Arg Ile Gly Pro
 1               5                  10                  15

Gly Gln Ala Phe Tyr Ala Thr Gly Ser Ile Ile Gly Asn Ile Arg Gln
            20                  25                  30

Ala His Cys
        35

<210> SEQ ID NO 13
<211> LENGTH: 35
<212> TYPE: PRT
<213> ORGANISM: Human immunodeficiency virus

<400> SEQUENCE: 13

Cys Thr Arg Pro Asn Asn Asn Thr Ile Thr Ser Ile Arg Ile Gly Pro
 1               5                  10                  15

Gly Gln Ala Phe Tyr Ala Thr Gly Ser Ile Ile Gly Asn Thr Arg Gln
            20                  25                  30

Ala His Cys
        35

<210> SEQ ID NO 14
<211> LENGTH: 35
<212> TYPE: PRT
<213> ORGANISM: Human immunodeficiency virus

<400> SEQUENCE: 14

Cys Thr Arg Pro Asn Asp Asn Ile Arg Lys Ser Val His Ile Gly Pro
 1               5                  10                  15

Gly Gln Ala Phe Tyr Ala Thr Gly Asp Ile Ile Gly Asp Ile Arg Arg
            20                  25                  30

Ala His Cys
        35

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 15
ggcttaggca tctcctatgg caggaagaa                                    29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcttaggca tctcctatgg caggaagaa                                    29

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agaaagagca gaagacagtg gcaatga                                      27

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agcccttcca gtccccccctt ttcttta                                     28

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcacagtaca atgtacacat g                                            21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaagaccca acaacaatac a                                            21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 21
tgtattgttg ttgggtcttg t                                          21

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Gly or Ser
<220> FEATURE:
<221> NAME/KEY: MOD_RES
<222> LOCATION: (8)
<223> OTHER INFORMATION: variable amino acid
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Asp or Glu

<400> SEQUENCE: 22

Asn Asn Thr Arg Lys Xaa Ile Xaa Ile Gly Pro Gly Xaa Ala Xaa Xaa
  1               5                  10                  15

Xaa Thr Gly Xaa Ile Ile Gly
             20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid
<220> FEATURE:
<221> NAME/KEY: MOD_RES
<222> LOCATION: (8)
<223> OTHER INFORMATION: Lys, His, or Arg
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Asp or Glu

<400> SEQUENCE: 23

Asn Asn Thr Arg Lys Xaa Ile Xaa Ile Gly Pro Gly Xaa Ala Xaa Xaa
  1               5                  10                  15

Xaa Thr Gly Xaa Ile Ile Gly
             20
```

```
<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid
<220> FEATURE:
<221> NAME/KEY: MOD_RES
<222> LOCATION: (8)
<223> OTHER INFORMATION: any naturally occurring amino acid other than
      Lys, His or Arg
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Asp, Glu, Lys, His or Arg

<400> SEQUENCE: 24

Asn Asn Thr Arg Lys Xaa Ile Xaa Ile Gly Pro Gly Xaa Ala Xaa Xaa
  1               5                  10                  15

Xaa Thr Gly Xaa Ile Ile Gly
             20

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: variable amino acid
<220> FEATURE:
<221> NAME/KEY: MOD_RES
<222> LOCATION: (8)
<223> OTHER INFORMATION: Lys, His or Arg
<220> FEATURE:
<221> NAME/KEY: MOD_RES
<222> LOCATION: (13)
<223> OTHER INFORMATION: variable amino acid
<220> FEATURE:
<221> NAME/KEY: MOD_RES
<222> LOCATION: (15)..(17)
<223> OTHER INFORMATION: variable amino acid
<220> FEATURE:
<221> NAME/KEY: MOD_RES
<222> LOCATION: (20)
<223> OTHER INFORMATION: Lys, His or Arg

<400> SEQUENCE: 25

Asn Asn Thr Arg Lys Xaa Ile Xaa Ile Gly Pro Gly Xaa Ala Xaa Xaa
  1               5                  10                  15

Xaa Thr Gly Xaa Ile Ile Gly
             20

<210> SEQ ID NO 26
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 26
cctcagccat tacacaggcc tgtccaaag                                            29

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttacagtaga aaaattcccc tc                                                   22

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaatctgtag aaattaattg tacaagac                                             28

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgctctacta atgttacaat gtgcttgtct tat                                       33

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aattcgccct tgaatctgta gaaattaat                                            29

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aattcgccct tttttgctct actaatg                                              27

<210> SEQ ID NO 32
<211> LENGTH: 35
<212> TYPE: PRT
<213> ORGANISM: Human immunodeficiency virus
```

```
<400> SEQUENCE: 32

Cys Thr Arg Pro Ile Asn Asn Arg Arg Lys Ser Ile His Ile Gly Pro
 1               5                  10                  15

Gly Gln Ala Phe Tyr Gly Thr Asp Asp Ile Ile Gly Asp Ile Arg Gln
            20                  25                  30

Ala His Cys
        35

<210> SEQ ID NO 33
<211> LENGTH: 35
<212> TYPE: PRT
<213> ORGANISM: Human immunodeficiency virus

<400> SEQUENCE: 33

Cys Thr Arg Pro Ser Asn Asn Arg Arg Lys Ser Ile His Met Gly Pro
 1               5                  10                  15

Gly Gln Ala Phe Tyr Gly Thr Asp Asp Ile Ile Gly Gly Ile Arg Lys
            20                  25                  30

Ala Arg Cys
        35

<210> SEQ ID NO 34
<211> LENGTH: 35
<212> TYPE: PRT
<213> ORGANISM: Human immunodeficiency virus

<400> SEQUENCE: 34

Cys Thr Arg Pro Ser Asn Asn Arg Arg Lys Ser Ile His Met Gly Pro
 1               5                  10                  15

Gly Gln Ala Phe Tyr Gly Thr Asp Asp Ile Ile Gly Asp Ile Arg Lys
            20                  25                  30

Ala Arg Cys
        35

<210> SEQ ID NO 35
<211> LENGTH: 35
<212> TYPE: PRT
<213> ORGANISM: Human immunodeficiency virus

<400> SEQUENCE: 35

Cys Ile Arg Pro Asn Asn Asn Thr Arg Thr Ser Ile Arg Ile Gly Pro
 1               5                  10                  15

Gly Gln Ala Phe Tyr Ala Thr Gly Asn Ile Ile Gly Gly Ile Arg Gln
            20                  25                  30

Ala Tyr Cys
        35

<210> SEQ ID NO 36
<211> LENGTH: 35
<212> TYPE: PRT
<213> ORGANISM: Human immunodeficiency virus

<400> SEQUENCE: 36

Cys Thr Arg Pro Asn Asn Asn Thr Arg Lys Ser Val His Ile Gly Leu
 1               5                  10                  15

Gly Gln Ala Phe Tyr Ala Thr Gly Asp Ile Ile Gly Asn Ile Arg Lys
            20                  25                  30

Ala His Cys
        35
```

```
<210> SEQ ID NO 37
<211> LENGTH: 35
<212> TYPE: PRT
<213> ORGANISM: Human immunodeficiency virus

<400> SEQUENCE: 37

Cys Thr Arg Pro Asn Asn Asn Thr Arg Lys Ser Val His Ile Gly Pro
  1               5                  10                  15

Gly Gln Ala Phe Tyr Ala Thr Gly Asp Ile Leu Gly Asn Ile Arg Gln
             20                  25                  30

Ala His Cys
         35

<210> SEQ ID NO 38
<211> LENGTH: 35
<212> TYPE: PRT
<213> ORGANISM: Human immunodeficiency virus

<400> SEQUENCE: 38

Cys Thr Arg Pro Asn Asn Asn Thr Arg Lys Ser Val His Ile Gly Pro
  1               5                  10                  15

Gly Gln Ala Phe Tyr Ala Thr Gly Asp Ile Ile Gly Asp Ile Arg Gln
             20                  25                  30

Ala Tyr Cys
         35

<210> SEQ ID NO 39
<211> LENGTH: 35
<212> TYPE: PRT
<213> ORGANISM: Human immunodeficiency virus

<400> SEQUENCE: 39

Cys Thr Arg Pro Asn Asn Asn Thr Lys Lys Ser Val His Ile Gly Pro
  1               5                  10                  15

Gly Gln Ala Phe Tyr Ala Thr Gly Asp Ile Ile Gly Asp Ile Arg Gln
             20                  25                  30

Ala Tyr Cys
         35

<210> SEQ ID NO 40
<211> LENGTH: 35
<212> TYPE: PRT
<213> ORGANISM: Human immunodeficiency virus

<400> SEQUENCE: 40

Cys Thr Arg Pro Asn Asp Asn Ile Arg Lys Arg Val His Ile Gly Pro
  1               5                  10                  15

Gly Gln Ala Phe Tyr Ala Thr Gly Asp Val Ile Gly Asp Ile Arg Arg
             20                  25                  30

Ala His Cys
         35
```